United States Patent
Mayo et al.

(10) Patent No.: US 6,188,965 B1
(45) Date of Patent: Feb. 13, 2001

(54) APPARATUS AND METHOD FOR AUTOMATED PROTEIN DESIGN

(75) Inventors: Stephen L. Mayo, Pasadena; Bassil I. Dahiyat, Los Angeles; D. Benjamin Gordon, Pasadena; Arthur Street, Los Angeles, all of CA (US)

(73) Assignee: California Institute of Technology, Pasadena, CA (US)

( * ) Notice: Under 35 U.S.C. 154(b), the term of this patent shall be extended for 0 days.

(21) Appl. No.: 09/058,459

(22) Filed: Apr. 10, 1998

Related U.S. Application Data

(60) Provisional application No. 60/043,464, filed on Apr. 11, 1997, provisional application No. 60/054,678, filed on Aug. 4, 1997, and provisional application No. 60/061,097, filed on Oct. 3, 1997.

(51) Int. Cl.[7] .............................. G01N 31/00; G06F 17/00

(52) U.S. Cl. .................................. 702/27; 706/45; 706/47

(58) Field of Search ..................................... 435/183, 70.1, 435/325; D14/114.1, 100; 530/350; 702/27; 706/45, 47; 712/200

(56) References Cited

PUBLICATIONS

Harbury et al., "High–Resolution Protein Design with Backbone Freedom," *Science*, 282:1462–1467 (1998).
Kortemme et al., "Design of a 20–Amino Acid, Three–Stranded β–Sheet Protein," *Science*, 281:253–256 (1988).
Koehl et al., "De Novo Protein Design. I. In Search of Stability and Specificity," *J. Mol. Biol.*, 293:1161–1181 (1999).
Gordon et al. "Energy functions for protein design," *Curr. Opinion in Struct. Biol.*, 9:509–513 (1999).
Cornell et al., "A Second Generation Force Field for the Simulation of Proteins, Nucleic Acids, and Organic Molecules," *J. Am. Chem. Soc.*, 117:5179–5197 (1995).
Villegas et al., "Stabilization of proteins by rational design of α–helix stability using helix/coil transition theory," *Folding & Design*, 1(1):29–34 (1995).
Hurley et al., "Design and Structural Analysis of Alternative Hydrophobic Core Packing Arrangements in Bacteriophage T4 Lysozyme," *J. Mol. Biol.*, 224:1143–1159(1992).
Tuffery et al., "A New Approach to the Rapid Determination of Protein Side Chain Conformations," *J. of Biomolecular Struct. & Dynamics*, 8(6):1267–1289 (1991).
Brooks et al., "CHARMM: A Program for Macromolecular Energy, Minimization, and Dynamics Calculations," *J. of Computational Chemistry*, 4(2):187–217 (1983).
Rappé et al., "Charge Equilibration for Molecular Dynamics Simulations," *J. Phys. Chem.*, 95:3358–3363 (1991).
Mayo et al., "DREIDING: A Generic Force Field for Molecular Simulations," *J. Phys. Chem.*, 94:8897–8909 (1990).

Harbury et al., "Repacking protein cores with backbone freedom: Structure prediction for coiled coils," *Proc. Natl. Acad. Sci. USA*, 92:8408–8412 (1995).
Kono et al., "Energy Minimization Method Using Automata Network for Sequence and Side–Chain Conformation Prediction from Given Backbone Geometry," *Proteins: Structure, Function, and Genetics*, 19:244–255 (1994).
Lee et al., "Accurate prediction of the stability and activity effects of site–directed mutagenesis on a protein core," *Nature*, 352:448–451 (1991).
van Gunsteren et al., "Prediction of the Activity and Stability Effects of Site–directed Mutagenesis on a Protein Core," *J. Mol. Biol.*, 227:389–395 (1992).
Wesson et al., "Atomic solvation parameters applied to molecular dynamics of proteins in solution," *Protein Science*, 1:227–235 (1992).
Dahiyat et al., "Protein design automation," *Caltech Biology Annual Report*, 172 (1995).
Dahiyat et al., "Probing the Role of Specificity in Protein Design," *Caltech Biology Annual Report*, 160–161 (1996).
DeGrado, W., "Proteins from Scratch," *Science*, 278:80–81 (1997).
Dahiyat et al., "De Novo Protein Design: Fully Automated Sequence Selection," *Science*, 278:82–87 (1997).
Dahiyat et al., "Protein Design Automation," Meeting Abstract; Protein Science vol. 4, Suppl. 2, 83 (1995).
Dahiyat et al., "Protein design Automation," Poster Sessions, Protein Science vol.5, Suppl. 1, 22–23 (1996).
Desjarlais et al., "New strategies in protein design," *Current Opinion in Biotechnology* ^:460–466 (1995).
Lazar et al., "De novo design of the hydrophobic core of ubiquitin," *Protein Science* 6:1167–1178 (1997).
Borman, "Proteins to Order," *Chemical and Engineering Newsletter (C&EN)* Oct. 6, 1997, 9–10 (1997).
Holmes, "First–ever designer protein fits like a glove," *New Scientist*, IPC Magazines Limited, Oct. 11, 1997 (1997).
Dahiyat et al., "Protein design automation," *Protein Science*, 5:895–903 (1996).
Desmet et al., "Theoretical and Algorithmical Optimization of the Dead–End Elimination Theorem," *Proceedings of the Pacific Symposium on Biocomputing '97*, 122–133 (1997).
Wodak, S.J., et al., "Analytical approximation to the accessible surface area of proteins", *Proc. Natl. Acad. Sci. USA* vol.77(4):1736–1740 (Apr. 1980).
Muñoz, V., et al., "Analysis of the effect of local interactions on protein stability", *Folding & Design* 1(3):167–178 (Apr. 1996).

(List continued on next page.)

Primary Examiner—John S. Brusca
Assistant Examiner—Young Kim
(74) Attorney, Agent, or Firm—Flehr Hohbach Test Albritton & Herbert LLP; Richard F. Trecartin, Esq.; Robin M. Silva, Esq.

(57) ABSTRACT

The present invention relates to apparatus and methods for quantitative protein design and optimization.

16 Claims, 10 Drawing Sheets

OTHER PUBLICATIONS

Dunbrack Jr., R.L., et al., "Conformational analysis of the backbone–dependent rotamer preferences of protein sidechains", *Struc. Biol.* vol.1(5):334–340 (May 1994).

Hellinga, H.W., et al., "Construction of New Ligand Binding Site in Proteins of Known Structure", *J. Mol. Biol.* 222:763–785 (1991).

Desmet, J., et al., "The Dead End Elimination Theorem as a New Approach to the Side Chain Packing Protein", from "The Protein Folding Problem and Tertiary Structure Prediction" Ch.10:1–49 (1994).

Lasters, I., et al., "Dead–End Based Modeling Tools to Explore the Sequence Space That is Compatible with a Given Scaffold", *Jour. of Protein Chem.* vol.16(5):449–452 (Jul. 1997).

Sun, S., et al., "Designing amino acid sequences to fold with good hydrophobic cores", *Protein Engg.* vol.8(12):1205–1213 (1995).

Desmet, J., et al., "The dead–end elimination theorem and its use in protein side–chain positioning", *Nature* vol.356:539–542 (Apr. 1992).

Bowie, J.U., et al., "Deciphering the Message in Protein Sequences: Tolerance to Amino Acid Substitutions", *Science* vol.247:1306–1310 (Mar. 1990).

Desjarlais, J.R., et al., "De novo design of the hydrophobic cores of proteins", *Protein Science* 4:2006–2018 (1995).

Pabo, C., "Designing proteins and peptides", *Nature* vol.301:200 (Jan. 1983).

Jones, D.T., "De novo protein design using pairwise potentials and a genetic algorithm", *Protein Science* 3:567–574 (1994).

Goldstein, R.F., "Efficient Rotamer Elimination Applied to Protein Side–Chains and Related Spin Glasses", *Biophys. Jour.* vol.66:1335–1340 (May 1994).

Dahiyat, B.I., et al., "First fully automatic design of a protein achieved by Caltech scientists", new press release (Oct. 1997).

Smith, C.K., et al., "Guidelines for Protein Design: The Energetics of β Sheet Side Chain Interactions", *Science* vol.270:980–982 (Nov. 1995).

Regan, L., "Helix is a helix is a helix?", *Proc. Natl. Acad. Sci. USA* vol.94:2796–2797 (Apr. 1997).

Muñoz, V., et al., "Intrinsic Secondary Structure Propensities of the Amino Acids, Using Statistical φ–ψ Matrices: Comparison with Experimental Scales", *Proteins* 20:301–311 (1994).

Muñoz, V., et al., "Helix design, prediction and stability", *Curr. Opin. in Biotech.* 6:382–386 (Aug. 1995).

Minor Jr., D.L., "Measurement of the β–sheet–forming propensities of amino acids", *Nature* vol.367:660–663 (Feb. 1994).

Hellinga, H.W., et al., "Optimal sequence selection in proteins of known structure by simulated evolution", *Proc. Natl. Acad. Sci., USA* vol.91:5803–5807 (Jun. 1994).

Bowie, J.U., et al., "A Method to Identify Protein Sequences that Fold into a Known Three–Dimensional Structure", *Science* vol.253:164–170 (Jul. 1991).

Dalal, S., et al., "Protein alchemy: Changing β–sheet into α–helix", *Nature Struc. Biol.* vol.4(7):548–552 (Jul. 1997).

Dahiyat, B.I., et al., "Proteins from Scratch", press digest email by *Science* (Sep. 26, 1997).

Berry, A., et al., "A quantitative methodology for the de novo design of proteins", *Protein Sci.* 3:1871–1882 (Oct. 1994).

Hellinga, H.W., "Rational protein design: Combining theory and experiment", *Proc. Natl. Acad. Sci, USA* vol.94:10015–10017 (Sep. 1997).

Padmanabhan, S., et al., "Relative helix–forming tendencies of nonpolar amino acids", *Nature* vol.344:268–270 (Mar. 1990).

Connolly, M.L., "Solvent–Accessible Surfaces of Proteins and Nucleic Acids", *Science* vol.221(4612):709–713 (Aug. 1983).

Eisenberg, D., et al., "Solvation energy in protein folding and binding", *Nature* vol.319:199–203 (Jan. 1986).

Ponder, J.W., et al., "Use of Packing Criteria in the Enumeration of Allowed Sequences for Different Structural Classes", release by Acad. Press Inc. (London) Ltd. pp.775–791(1987).

Dahiyat, B.I., et al., "Automated design of the surface positions of protein helices", *Protein Science* 6:105 (Jun. 1997).

Lasters et al., "Enhanced dead–end elimination in the search for the global minimum energy conformation of a collection of protein side chains," 1995, Protein Engineering, vol. 8, No. 8, pp. 815–822.*

Munoz et al., "Intrinsic Secondary Structure Propensities of the Amino Acids, Using Statistical phi–psi Matrices: Comparison With Experimental Scales," 1994, Proteins: Structures, Function, and Genetics, vol. 20, pp. 301–311.*

Eisenberg et al., "Solvation energy in protein folding and binding," 1986, Nature, vol. 319, pp. 199–203.*

Dunbrack et al., "Conformational analysis of the backbone–dependent rotamer preferences of protein sidechains," 1994, Structural Biology, vol. 1, No. 5, pp. 334–340.*

Bassil et al., "Protein Design Automation," 1996, Protein Science, vol. 5, pp. 895–903, Nov. 30, 1999.*

* cited by examiner

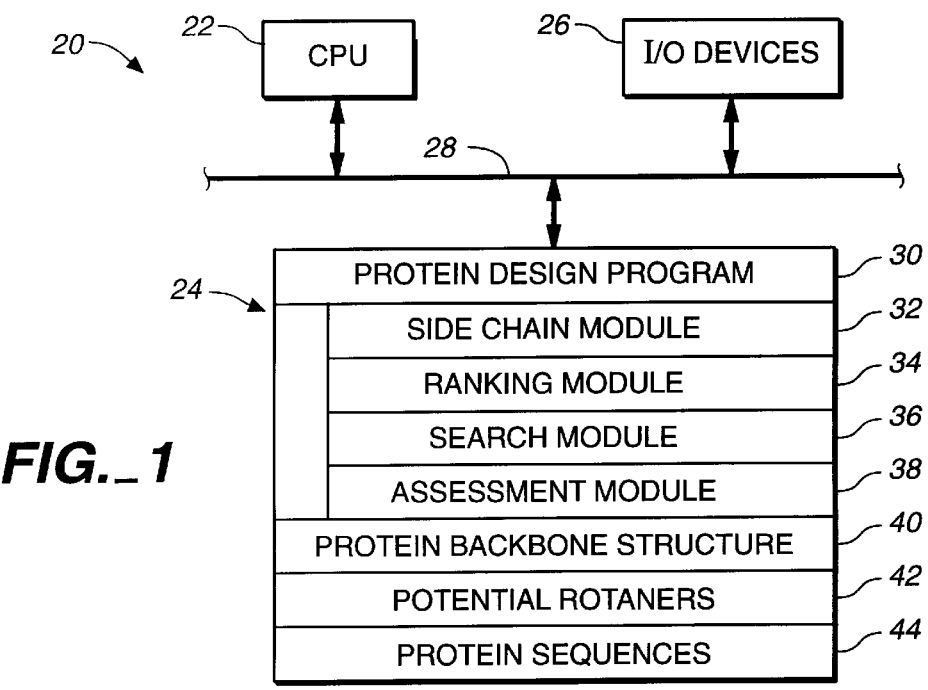
FIG._1
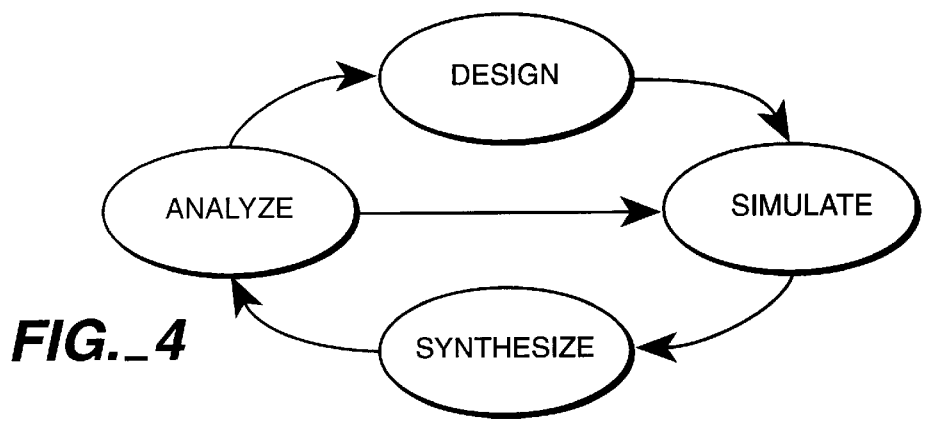
FIG._4
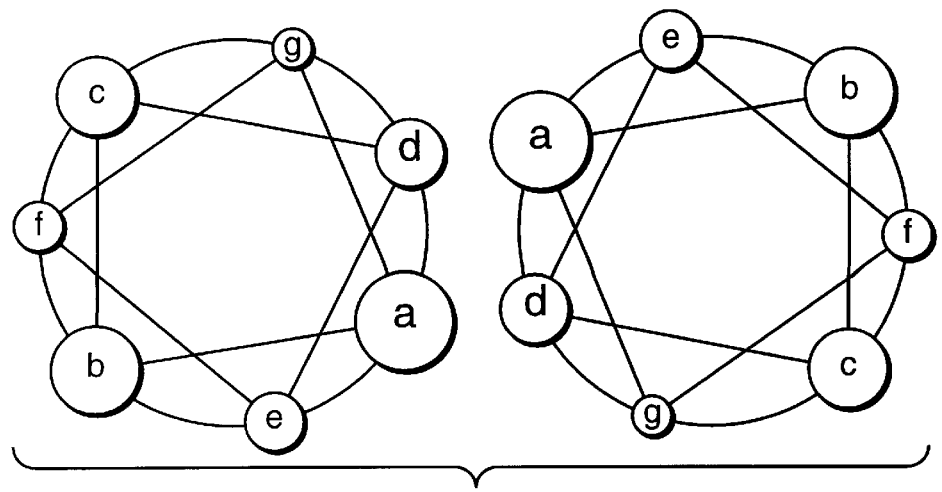
FIG._5

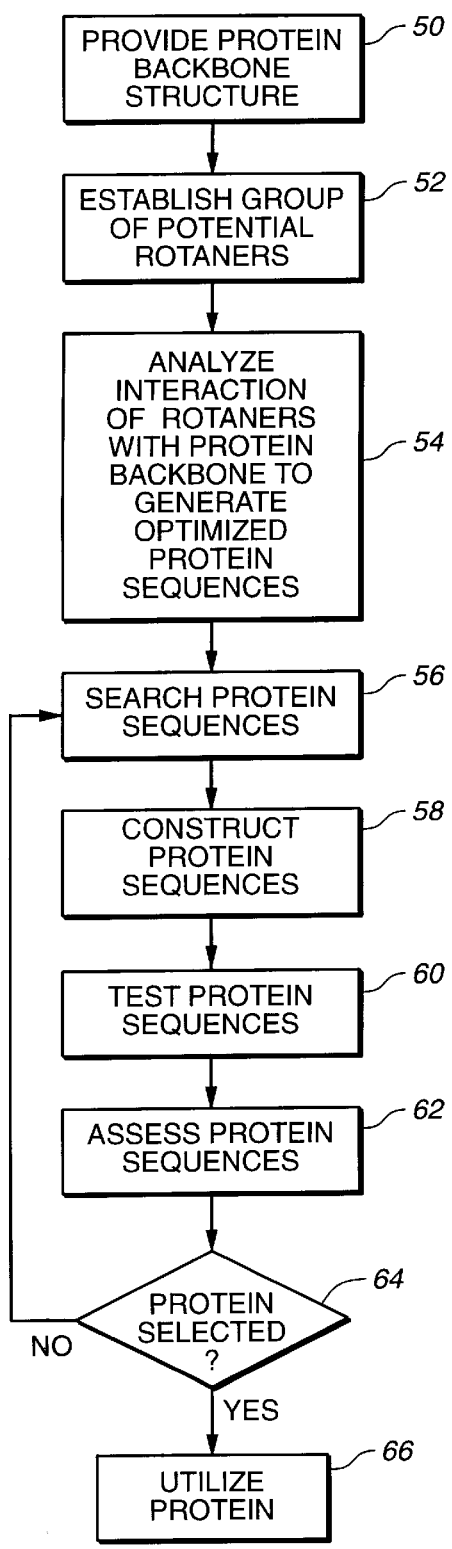
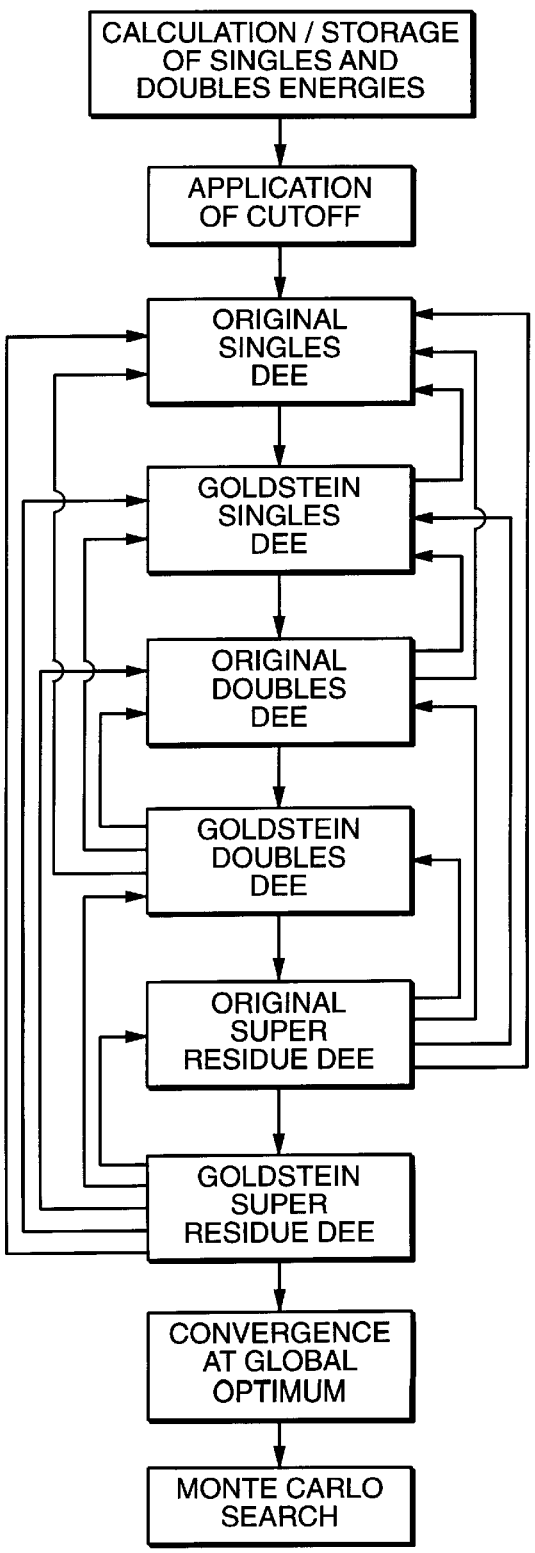
FIG._2                    FIG._3

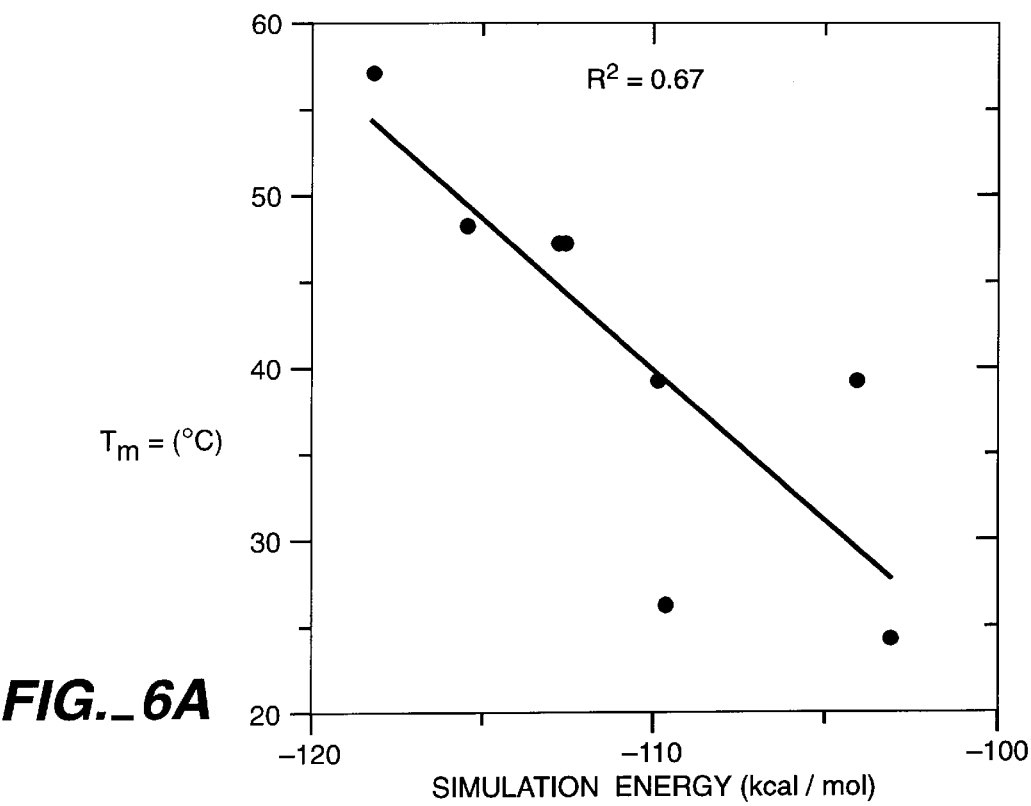
FIG._6A
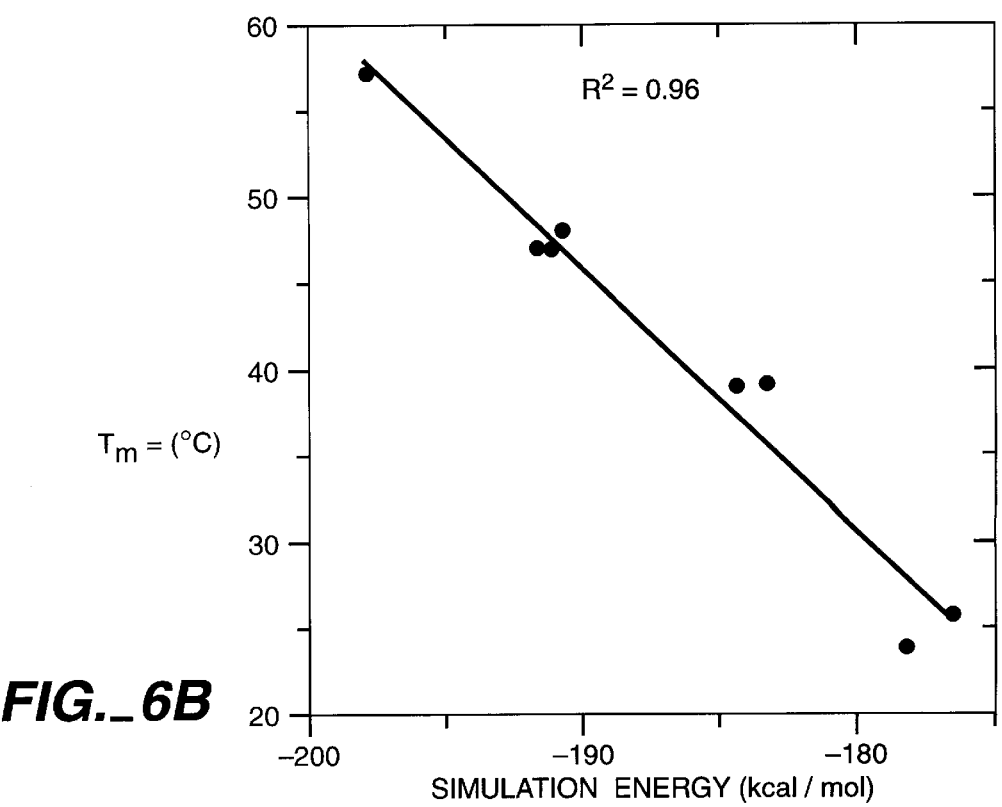
FIG._6B

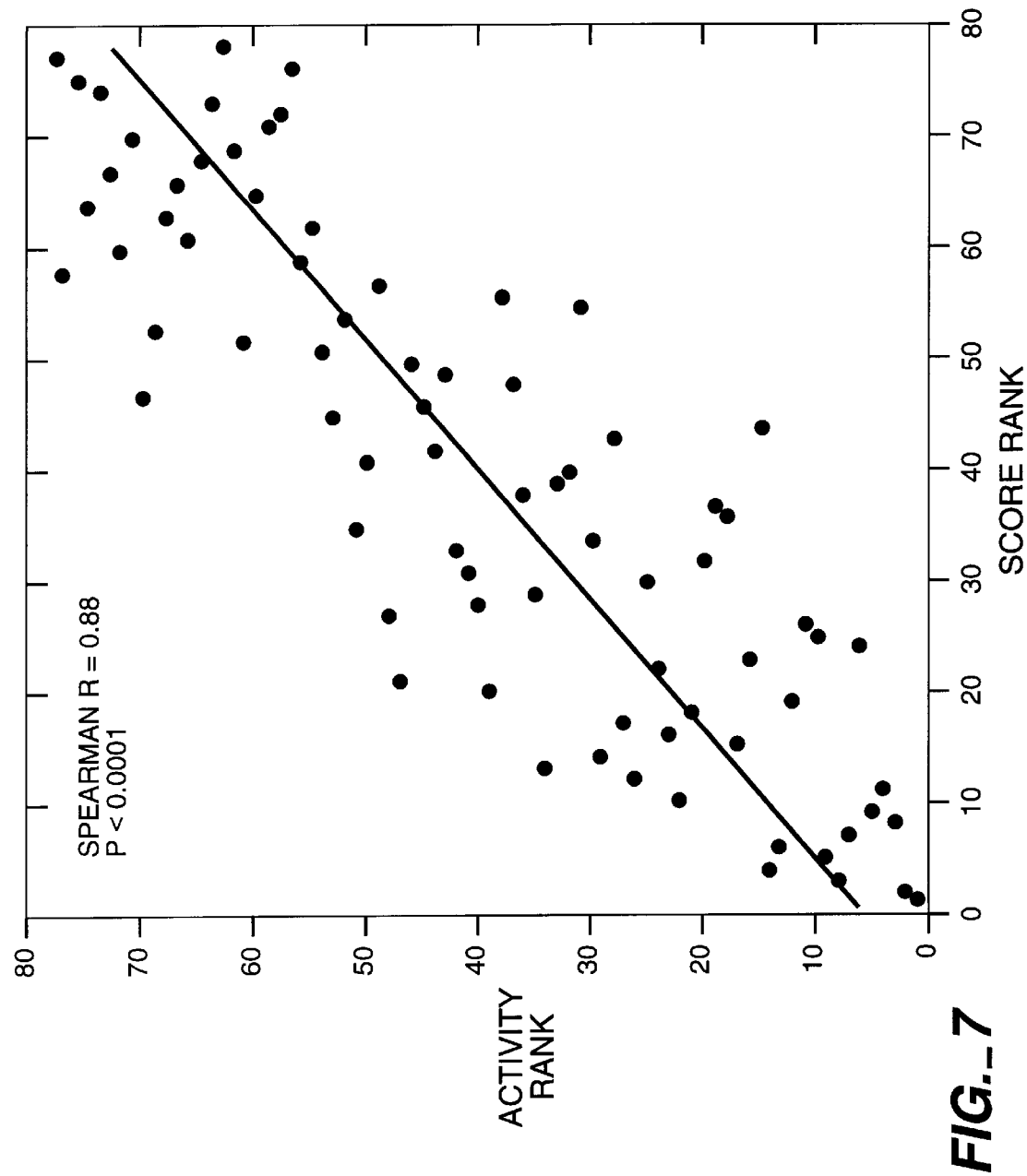
FIG._7

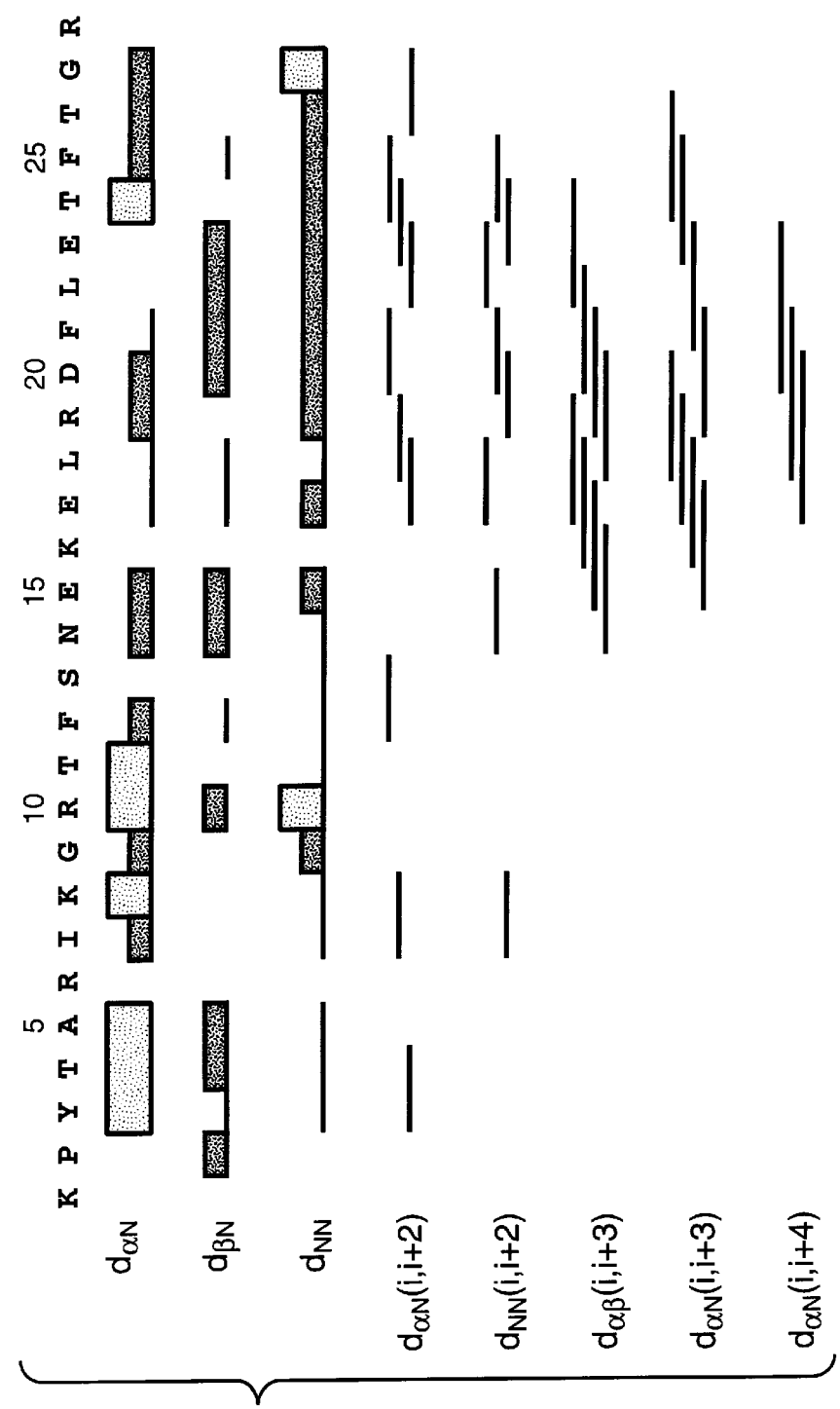
FIG._8
FIG._9B

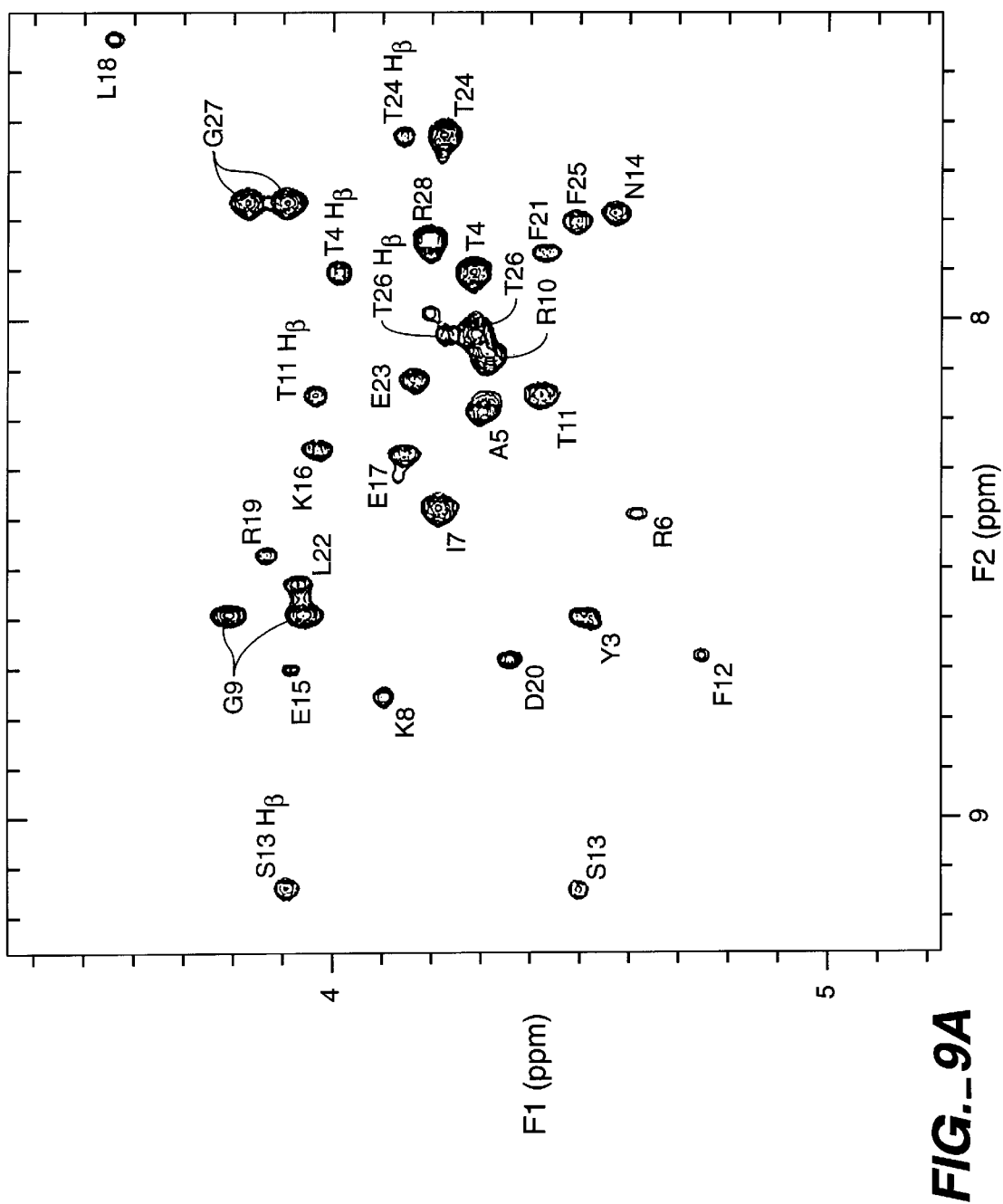
FIG._9A

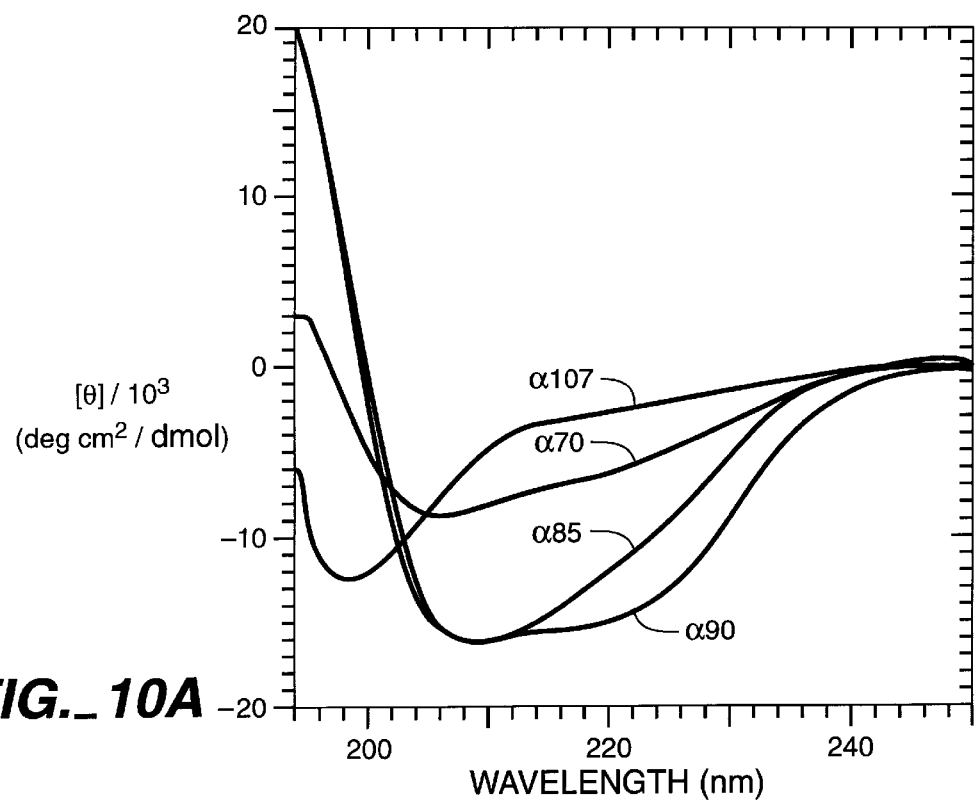
FIG._10A
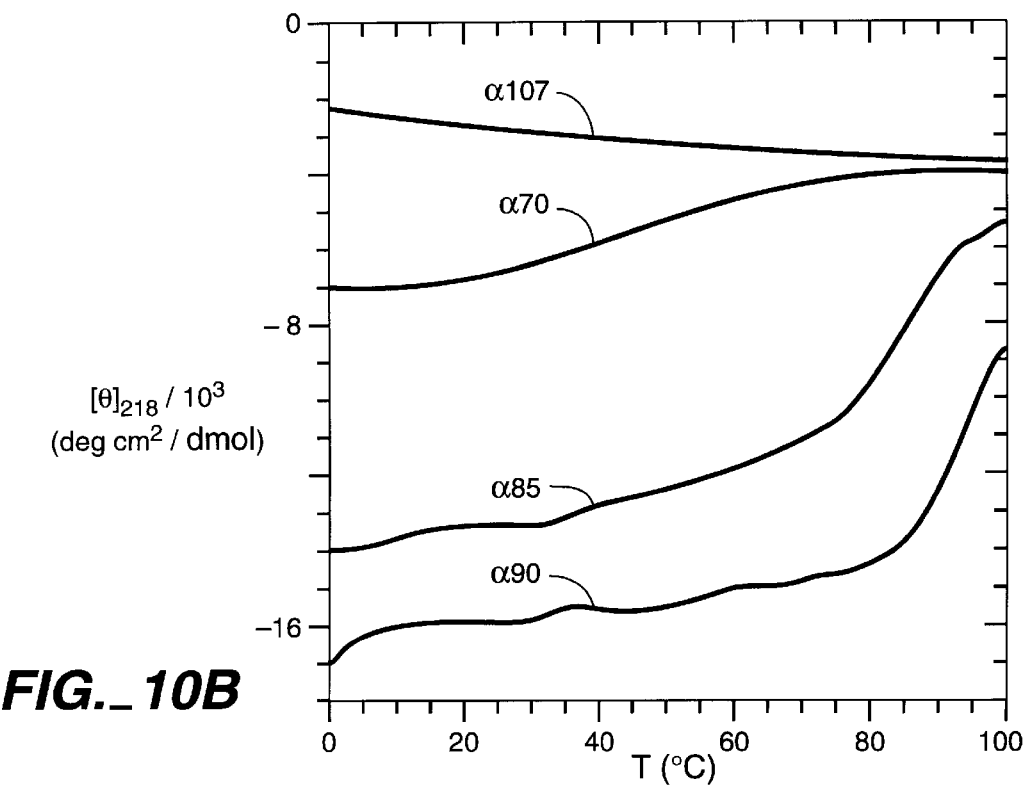
FIG._10B

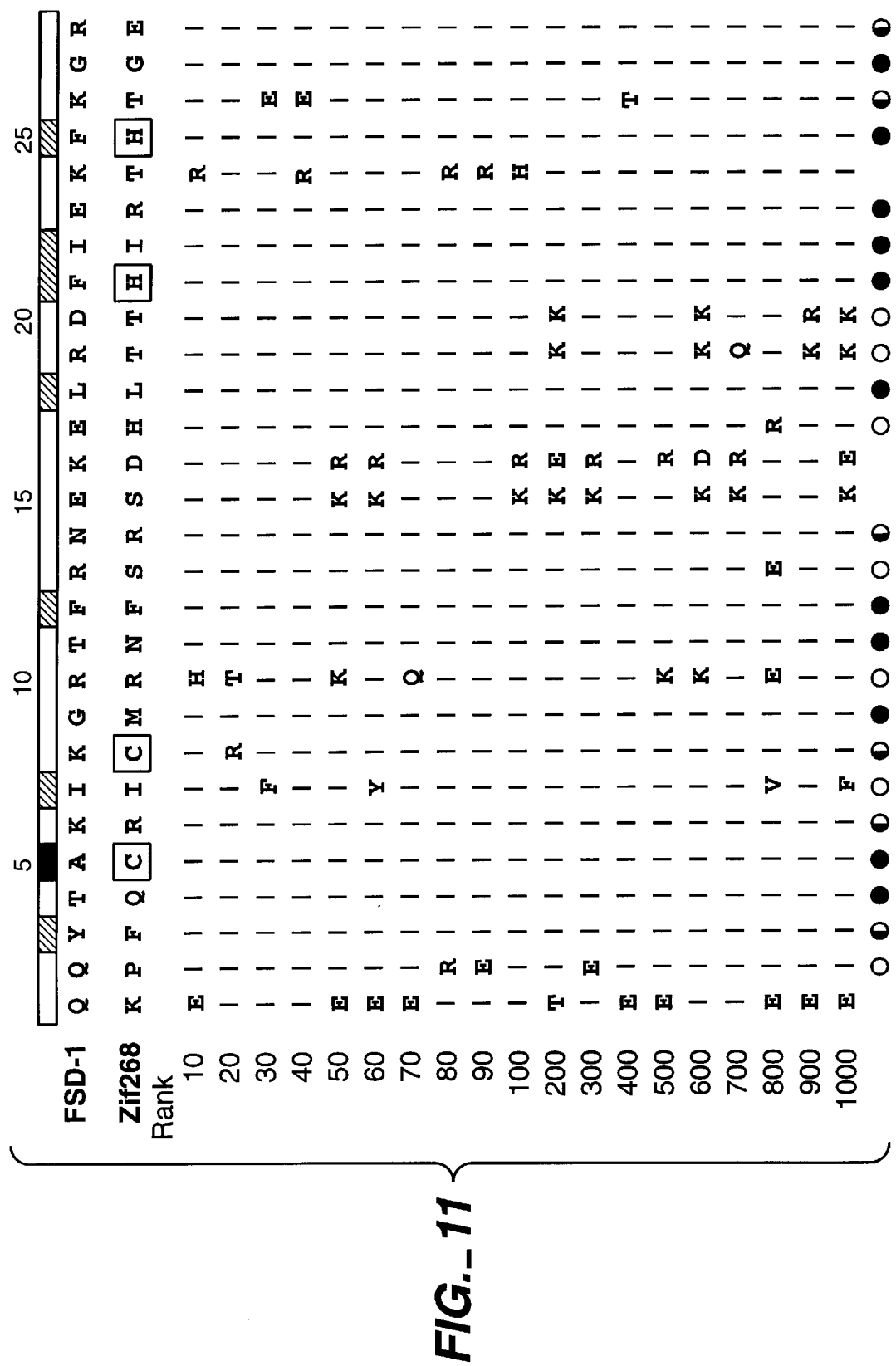
FIG._11

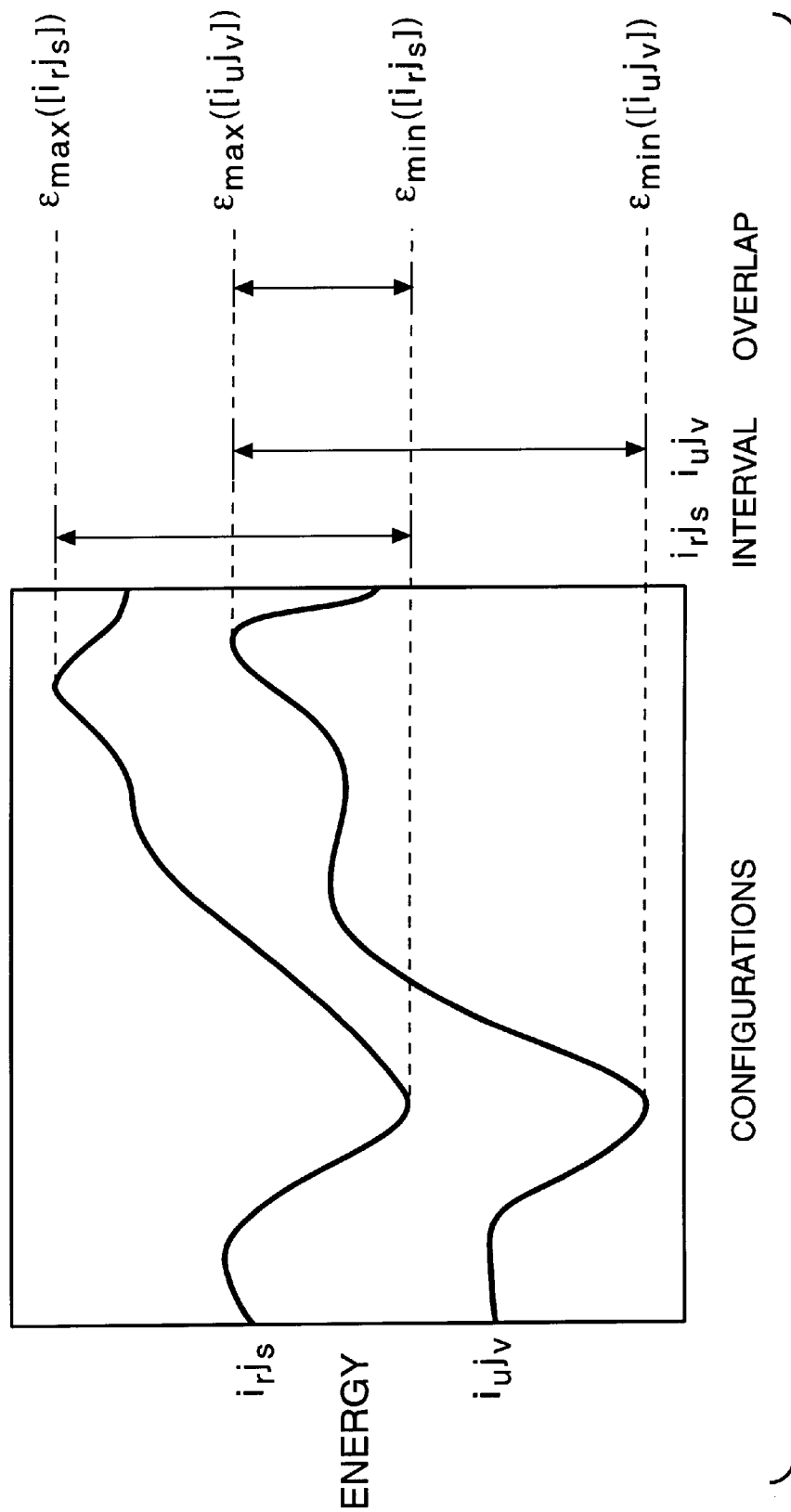
FIG._12

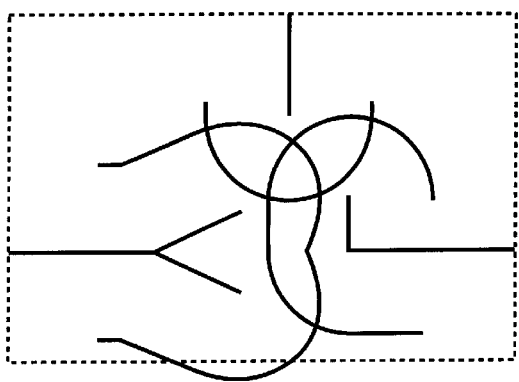
FIG._13A
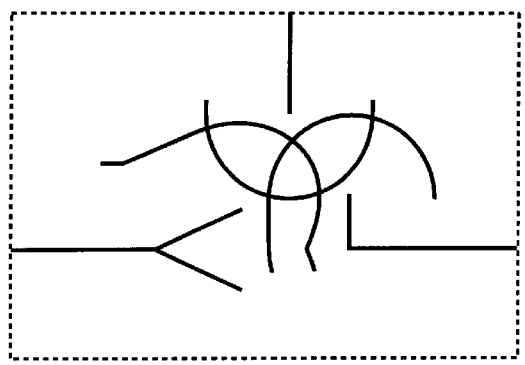
FIG._13B
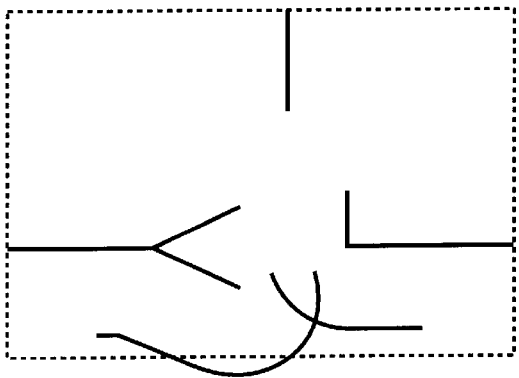
FIG._13C
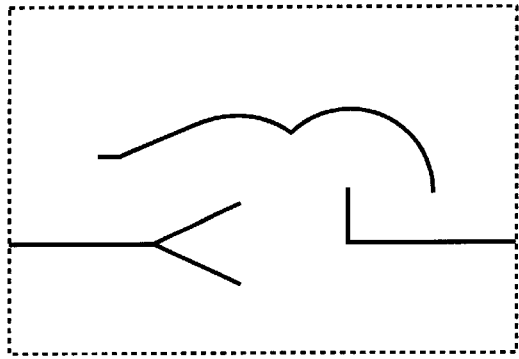
FIG._13D
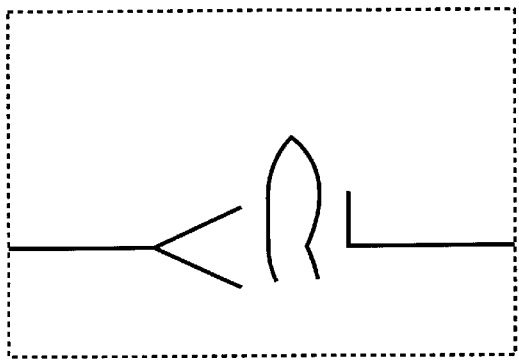
FIG._13E
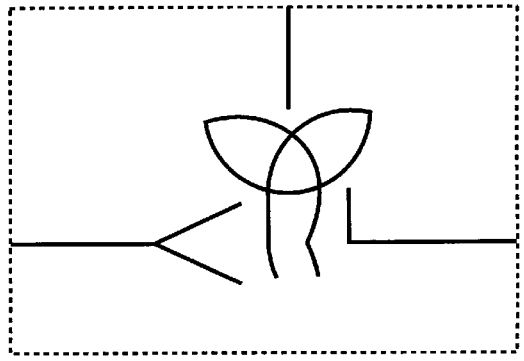
FIG._13F

SEQUENCE LISTING

<160> NUMBER OF SEQ ID NOS: 79

<210> SEQ ID NO 1
<211> LENGTH: 28
<212> TYPE: PRT
<213> ORGANISM: Mouse

<400> SEQUENCE: 1

```
Lys Pro Phe Gln Cys Arg Ile Cys Met Arg Asn Phe Ser Arg Ser Asp
  1               5                  10                  15

His Leu Thr Thr His Ile Arg Thr His Thr Gly Glu
              20                  25

<210> SEQ ID NO 2
<211> LENGTH: 28
<212> TYPE: PRT
<213> ORGANISM: Artificial Sequence
<220> FEATURE:
<223> OTHER INFORMATION: Description of Artificial Sequence: Synthetic

<400> SEQUENCE: 2

Lys Pro Tyr Thr Ala Arg Ile Lys Gly Arg Thr Phe Ser Asn Glu Lys
  1               5                  10                  15

Glu Leu Arg Asp Phe Leu Glu Thr Phe Thr Gly Arg
              20                  25

<210> SEQ ID NO 3
<211> LENGTH: 28
<212> TYPE: PRT
<213> ORGANISM: Artificial Sequence
<220> FEATURE:
<223> OTHER INFORMATION: Description of Artificial Sequence: Synthetic

<400> SEQUENCE: 3

Gln Gln Tyr Thr Ala Lys Ile Lys Gly Arg Thr Phe Arg Asn Glu Lys
  1               5                  10                  15

Glu Leu Arg Asp Phe Ile Glu Lys Phe Lys Gly Arg
              20                  25

<210> SEQ ID NO 4
<211> LENGTH: 28
<212> TYPE: PRT
<213> ORGANISM: Artificial Sequence
<220> FEATURE:
<223> OTHER INFORMATION: Description of Artificial Sequence: Synthetic

<400> SEQUENCE: 4

Glu Gln Tyr Thr Ala Lys Ile Lys Gly His Thr Phe Arg Asn Glu Lys
  1               5                  10                  15

Glu Leu Arg Asp Phe Ile Glu Arg Phe Lys Gly Arg
              20                  25

<210> SEQ ID NO 5
<211> LENGTH: 28
<212> TYPE: PRT
<213> ORGANISM: Artificial Sequence
<220> FEATURE:
<223> OTHER INFORMATION: Description of Artificial Sequence: Synthetic

<400> SEQUENCE: 5

Gln Gln Tyr Thr Ala Lys Ile Arg Gly Thr Thr Phe Arg Asn Glu Lys
  1               5                  10                  15

Glu Leu Arg Asp Phe Ile Glu Lys Phe Lys Gly Arg
              20                  25

<210> SEQ ID NO 6
<211> LENGTH: 28
<212> TYPE: PRT
<213> ORGANISM: Artificial Sequence
<220> FEATURE:
<223> OTHER INFORMATION: Description of Artificial Sequence: Synthetic
```

```
<400> SEQUENCE: 6

Gln Gln Tyr Thr Ala Lys Phe Lys Gly Arg Thr Phe Arg Asn Glu Lys
  1               5                  10                  15

Glu Leu Arg Asp Phe Ile Glu Lys Phe Glu Gly Arg
             20                  25

<210> SEQ ID NO 7
<211> LENGTH: 28
<212> TYPE: PRT
<213> ORGANISM: Artificial Sequence
<220> FEATURE:
<223> OTHER INFORMATION: Description of Artificial Sequence: Synthetic

<400> SEQUENCE: 7

Gln Gln Tyr Thr Ala Lys Ile Lys Gly Arg Thr Phe Arg Asn Glu Lys
  1               5                  10                  15

Glu Leu Arg Asp Phe Ile Glu Arg Phe Glu Gly Arg
             20                  25

<210> SEQ ID NO 8
<211> LENGTH: 28
<212> TYPE: PRT
<213> ORGANISM: Artificial Sequence
<220> FEATURE:
<223> OTHER INFORMATION: Description of Artificial Sequence: Synthetic

<400> SEQUENCE: 8

Glu Gln Tyr Thr Ala Lys Ile Lys Gly Lys Thr Phe Arg Asn Lys Arg
  1               5                  10                  15

Glu Leu Arg Asp Phe Ile Glu Lys Phe Lys Gly Arg
             20                  25

<210> SEQ ID NO 9
<211> LENGTH: 28
<212> TYPE: PRT
<213> ORGANISM: Artificial Sequence
<220> FEATURE:
<223> OTHER INFORMATION: Description of Artificial Sequence: Synthetic

<400> SEQUENCE: 9

Glu Gln Tyr Thr Ala Lys Tyr Lys Gly Arg Thr Phe Arg Asn Lys Arg
  1               5                  10                  15

Glu Leu Arg Asp Phe Ile Glu Lys Phe Lys Gly Arg
             20                  25

<210> SEQ ID NO 10
<211> LENGTH: 28
<212> TYPE: PRT
<213> ORGANISM: Artificial Sequence
<220> FEATURE:
<223> OTHER INFORMATION: Description of Artificial Sequence: Synthetic

<400> SEQUENCE: 10

Glu Gln Tyr Thr Ala Lys Ile Lys Gly Gln Thr Phe Arg Asn Glu Lys
  1               5                  10                  15

Glu Leu Arg Asp Phe Ile Glu Lys Phe Lys Gly Arg
             20                  25

<210> SEQ ID NO 11
<211> LENGTH: 28
<212> TYPE: PRT
<213> ORGANISM: Artificial Sequence
<220> FEATURE:
<223> OTHER INFORMATION: Description of Artificial Sequence: Synthetic
```

```
<400> SEQUENCE: 11

Gln Arg Tyr Thr Ala Lys Ile Lys Gly Arg Thr Phe Arg Asn Glu Lys
 1               5                  10                  15

Glu Leu Arg Asp Phe Ile Glu Arg Phe Lys Gly Arg
            20                  25

<210> SEQ ID NO 12
<211> LENGTH: 28
<212> TYPE: PRT
<213> ORGANISM: Artificial Sequence
<220> FEATURE:
<223> OTHER INFORMATION: Description of Artificial Sequence: Synthetic

<400> SEQUENCE: 12

Gln Glu Tyr Thr Ala Lys Ile Lys Gly Arg Thr Phe Arg Asn Glu Lys
 1               5                  10                  15

Glu Leu Arg Asp Phe Ile Glu Arg Phe Lys Gly Arg
            20                  25

<210> SEQ ID NO 13
<211> LENGTH: 28
<212> TYPE: PRT
<213> ORGANISM: Artificial Sequence
<220> FEATURE:
<223> OTHER INFORMATION: Description of Artificial Sequence: Synthetic

<400> SEQUENCE: 13

Gln Gln Tyr Thr Ala Lys Ile Lys Gly Arg Thr Phe Arg Asn Lys Arg
 1               5                  10                  15

Glu Leu Arg Asp Phe Ile Glu His Phe Lys Gly Arg
            20                  25

<210> SEQ ID NO 14
<211> LENGTH: 28
<212> TYPE: PRT
<213> ORGANISM: Artificial Sequence
<220> FEATURE:
<223> OTHER INFORMATION: Description of Artificial Sequence: Synthetic

<400> SEQUENCE: 14

Thr Gln Tyr Thr Ala Lys Ile Lys Gly Arg Thr Phe Arg Asn Lys Glu
 1               5                  10                  15

Glu Leu Lys Lys Phe Ile Glu Lys Phe Lys Gly Arg
            20                  25

<210> SEQ ID NO 15
<211> LENGTH: 28
<212> TYPE: PRT
<213> ORGANISM: Artificial Sequence
<220> FEATURE:
<223> OTHER INFORMATION: Description of Artificial Sequence: Synthetic

<400> SEQUENCE: 15

Gln Glu Tyr Thr Ala Lys Ile Lys Gly Arg Thr Phe Arg Asn Lys Arg
 1               5                  10                  15

Glu Leu Arg Asp Phe Ile Glu Lys Phe Lys Gly Arg
            20                  25

<210> SEQ ID NO 16
<211> LENGTH: 28
<212> TYPE: PRT
<213> ORGANISM: Artificial Sequence
<220> FEATURE:
```

<223> OTHER INFORMATION: Description of Artificial Sequence: Synthetic

<400> SEQUENCE: 16

Glu Gln Tyr Thr Ala Lys Ile Lys Gly Arg Thr Phe Arg Asn Glu Lys
 1               5                  10                  15

Glu Leu Arg Asp Phe Ile Glu Lys Phe Thr Gly Arg
            20                  25

<210> SEQ ID NO 17
<211> LENGTH: 28
<212> TYPE: PRT
<213> ORGANISM: Artificial Sequence
<220> FEATURE:
<223> OTHER INFORMATION: Description of Artificial Sequence: Synthetic

<400> SEQUENCE: 17

Glu Gln Tyr Thr Ala Lys Ile Lys Gly Lys Thr Phe Arg Asn Glu Arg
 1               5                  10                  15

Glu Leu Arg Asp Phe Ile Glu Lys Phe Lys Gly Arg
            20                  25

<210> SEQ ID NO 18
<211> LENGTH: 28
<212> TYPE: PRT
<213> ORGANISM: Artificial Sequence
<220> FEATURE:
<223> OTHER INFORMATION: Description of Artificial Sequence: Synthetic

<400> SEQUENCE: 18

Gln Gln Tyr Thr Ala Lys Ile Lys Gly Lys Thr Phe Arg Asn Lys Asp
 1               5                  10                  15

Glu Leu Lys Lys Phe Ile Glu Lys Phe Lys Gly Arg
            20                  25

<210> SEQ ID NO 19
<211> LENGTH: 28
<212> TYPE: PRT
<213> ORGANISM: Artificial Sequence
<220> FEATURE:
<223> OTHER INFORMATION: Description of Artificial Sequence: Synthetic

<400> SEQUENCE: 19

Gln Gln Tyr Thr Ala Lys Ile Lys Gly Arg Thr Phe Arg Asn Lys Arg
 1               5                  10                  15

Glu Leu Gln Asp Phe Ile Glu Lys Phe Lys Gly Arg
            20                  25

<210> SEQ ID NO 20
<211> LENGTH: 28
<212> TYPE: PRT
<213> ORGANISM: Artificial Sequence
<220> FEATURE:
<223> OTHER INFORMATION: Description of Artificial Sequence: Synthetic

<400> SEQUENCE: 20

Glu Gln Tyr Thr Ala Lys Val Lys Gly Glu Thr Phe Glu Asn Glu Lys
 1               5                  10                  15

Arg Leu Arg Asp Phe Ile Glu Lys Phe Lys Gly Arg
            20                  25

<210> SEQ ID NO 21
<211> LENGTH: 28
<212> TYPE: PRT
<213> ORGANISM: Artificial Sequence

```
<220> FEATURE:
<223> OTHER INFORMATION: Description of Artificial Sequence: Synthetic

<400> SEQUENCE: 21

Glu Gln Tyr Thr Ala Lys Ile Lys Gly Arg Thr Phe Arg Asn Glu Lys
  1               5                  10                  15

Glu Leu Lys Arg Phe Ile Glu Lys Phe Lys Gly Arg
             20                  25

<210> SEQ ID NO 22
<211> LENGTH: 28
<212> TYPE: PRT
<213> ORGANISM: Artificial Sequence
<220> FEATURE:
<223> OTHER INFORMATION: Description of Artificial Sequence: Synthetic

<400> SEQUENCE: 22

Glu Gln Tyr Thr Ala Lys Phe Lys Gly Arg Thr Phe Arg Asn Lys Glu
  1               5                  10                  15

Glu Leu Lys Lys Phe Ile Glu Lys Phe Lys Gly Arg
             20                  25

<210> SEQ ID NO 23
<211> LENGTH: 33
<212> TYPE: PRT
<213> ORGANISM: yeast

<400> SEQUENCE: 23

Arg Met Lys Gln Leu Glu Asp Lys Val Glu Glu Leu Leu Ser Lys Asn
  1               5                  10                  15

Tyr His Leu Glu Asn Glu Val Ala Arg Leu Lys Lys Leu Val Gly Glu
             20                  25                  30

Arg

<210> SEQ ID NO 24
<211> LENGTH: 33
<212> TYPE: PRT
<213> ORGANISM: yeast

<400> SEQUENCE: 24

Arg Met Lys Gln Leu Glu Asp Lys Val Glu Glu Leu Leu Ser Lys Asn
  1               5                  10                  15

Tyr His Leu Glu Asn Glu Val Ala Arg Leu Lys Lys Leu Ala Gly Glu
             20                  25                  30

Arg

<210> SEQ ID NO 25
<211> LENGTH: 33
<212> TYPE: PRT
<213> ORGANISM: yeast

<400> SEQUENCE: 25

Arg Met Lys Gln Leu Glu Asp Lys Val Glu Glu Leu Leu Ser Lys Asn
  1               5                  10                  15

Tyr His Leu Glu Asn Glu Met Ala Arg Leu Lys Lys Leu Val Gly Glu
             20                  25                  30

Arg

<210> SEQ ID NO 26
<211> LENGTH: 33
<212> TYPE: PRT
```

<213> ORGANISM: yeast

<400> SEQUENCE: 26

Arg Leu Lys Gln Met Glu Asp Lys Val Glu Glu Leu Leu Ser Lys Asn
1               5                   10                  15
Tyr His Leu Glu Asn Glu Val Ala Arg Leu Lys Lys Leu Val Gly Glu
            20                  25                  30
Arg

<210> SEQ ID NO 27
<211> LENGTH: 33
<212> TYPE: PRT
<213> ORGANISM: yeast

<400> SEQUENCE: 27

Arg Leu Lys Gln Met Glu Asp Lys Val Glu Glu Leu Leu Ser Lys Asn
1               5                   10                  15
Tyr His Leu Glu Asn Glu Val Ala Arg Leu Lys Lys Leu Ala Gly Glu
            20                  25                  30
Arg

<210> SEQ ID NO 28
<211> LENGTH: 33
<212> TYPE: PRT
<213> ORGANISM: yeast

<400> SEQUENCE: 28

Arg Met Lys Gln Trp Glu Asp Lys Ala Glu Glu Leu Leu Ser Lys Asn
1               5                   10                  15
Tyr His Leu Glu Asn Glu Val Ala Arg Leu Lys Lys Leu Val Gly Glu
            20                  25                  30
Arg

<210> SEQ ID NO 29
<211> LENGTH: 33
<212> TYPE: PRT
<213> ORGANISM: yeast

<400> SEQUENCE: 29

Arg Met Lys Gln Phe Glu Asp Lys Val Glu Glu Leu Leu Ser Lys Asn
1               5                   10                  15
Tyr His Leu Glu Asn Glu Val Ala Arg Leu Lys Lys Leu Val Gly Glu
            20                  25                  30
    Arg

<210> SEQ ID NO 30
<211> LENGTH: 33
<212> TYPE: PRT
<213> ORGANISM: yeast

<400> SEQUENCE: 30

Arg Met Lys Gln Leu Glu Asp Lys Val Glu Glu Leu Leu Ser Lys Asn
1               5                   10                  15
Tyr His Ala Glu Asn Glu Val Ala Arg Leu Lys Lys Leu Val Gly Glu
            20                  25                  30
    Arg

<210> SEQ ID NO 31
<211> LENGTH: 12

```
<212> TYPE: PRT
<213> ORGANISM: Artificial Sequence
<220> FEATURE:
<223> OTHER INFORMATION: Description of Artificial Sequence: Synthetic

<400> SEQUENCE: 31

Lys Gln Asp Glu Glu Ser Tyr His Asn Ala Arg Lys
 1               5                  10

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 32

Glu Lys Asp Arg Glu Arg Arg Arg Glu Arg Arg Glu
 1               5                  10

<210> SEQ ID NO 33
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 33

Glu Lys Gln Lys Glu Arg Glu Arg Glu Glu Arg Gln
 1               5                  10

<210> SEQ ID NO 34
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 34

Ala Arg Ala Ala Ala Ala Arg Arg Arg Ala Arg Ala
 1               5                  10

<210> SEQ ID NO 35
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 35

Arg Glu Glu Arg Arg Arg Glu Asp Arg Lys Arg Glu
 1               5                  10

<210> SEQ ID NO 36
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 36

Asn Thr Arg Ala Lys Ser Ala Asn His Asn Thr Gln
 1               5                  10

<210> SEQ ID NO 37
<211> LENGTH: 12
<212> TYPE: PRT
```

<213> ORGANISM: Artificial Sequence
<220> FEATURE:
<223> OTHER INFORMATION: Description of Artificial Sequence: Synthetic

<400> SEQUENCE: 37

```
Ala Ala Ala Ala Ala Ala Ala Ala Ala Ala
 1               5                  10
```

<210> SEQ ID NO 38
<211> LENGTH: 56
<212> TYPE: PRT
<213> ORGANISM: Streptococcus sp.

<400> SEQUENCE: 38

```
Met Thr Tyr Lys Leu Ile Leu Asn Gly Lys Thr Leu Lys Gly Glu Thr
 1               5                  10                  15

Thr Thr Glu Ala Val Asp Ala Ala Thr Ala Glu Lys Val Phe Lys Gln
            20                  25                  30

Tyr Ala Asn Asp Asn Gly Val Asp Gly Glu Trp Thr Tyr Asp Asp Ala
        35                  40                  45

Thr Lys Thr Phe Thr Val Thr Glu
    50                  55
```

<210> SEQ ID NO 39
<211> LENGTH: 56
<212> TYPE: PRT
<213> ORGANISM: Streptococcus sp.

<400> SEQUENCE: 39

```
Met Thr Trp Lys Tyr Ile Ile Asn Gly Lys Thr Leu Lys Gly Glu Thr
 1               5                  10                  15

Thr Thr Glu Ile Val Asp Ala Ala Thr Phe Glu Lys Val Trp Lys Gln
            20                  25                  30

Tyr Leu Asn Asp Asn Gly Ile Asp Gly Glu Phe Thr Tyr Asp Asp Ala
        35                  40                  45

Thr Lys Thr Leu Thr Ile Thr Glu
    50                  55
```

<210> SEQ ID NO 40
<211> LENGTH: 56
<212> TYPE: PRT
<213> ORGANISM: Streptococcus sp.

<400> SEQUENCE: 40

```
Met Thr Phe Lys Ile Ile Phe Asn Gly Lys Thr Leu Lys Gly Glu Thr
 1               5                  10                  15

Thr Thr Glu Ile Val Asp Ala Ala Thr Val Glu Lys Val Trp Lys Gln
            20                  25                  30

Tyr Val Asn Asp Asn Gly Leu Asp Gly Glu Trp Thr Tyr Asp Asp Ala
        35                  40                  45

Thr Lys Thr Phe Thr Ile Thr Glu
    50                  55
```

<210> SEQ ID NO 41
<211> LENGTH: 56
<212> TYPE: PRT
<213> ORGANISM: Streptococcus sp.

<400> SEQUENCE: 41

```
Met Thr Phe Lys Leu Ile Ile Asn Gly Lys Thr Leu Lys Gly Glu Thr
 1               5                  10                  15
```

```
Thr Thr Glu Ala Val Asp Ala Ala Thr Ala Glu Lys Val Phe Lys Gln
            20                  25                  30

Tyr Ile Asn Asp Asn Gly Ile Asp Gly Glu Trp Thr Tyr Asp Asp Ala
        35                  40                  45

Thr Lys Thr Trp Thr Ile Thr Glu
    50                  55

<210> SEQ ID NO 42
<211> LENGTH: 56
<212> TYPE: PRT
<213> ORGANISM: Streptococcus sp.

<400> SEQUENCE: 42

Met Thr Phe Lys Leu Ile Ile Asn Gly Lys Thr Leu Lys Gly Glu Thr
  1               5                  10                  15

Thr Thr Glu Ala Val Asp Ala Ala Thr Ala Glu Lys Val Phe Lys Gln
            20                  25                  30

Tyr Leu Asn Asp Asn Gly Ile Asp Gly Glu Trp Thr Tyr Asp Asp Ala
        35                  40                  45

Thr Lys Thr Trp Thr Phe Thr Glu
    50                  55

<210> SEQ ID NO 43
<211> LENGTH: 56
<212> TYPE: PRT
<213> ORGANISM: Streptococcus sp.

<400> SEQUENCE: 43

Met Thr Phe Lys Leu Ile Ile Asn Gly Lys Thr Leu Lys Gly Glu Thr
  1               5                  10                  15

Thr Thr Glu Ala Val Asp Ala Ala Thr Ala Glu Lys Val Phe Lys Gln
            20                  25                  30

Tyr Ala Asn Asp Asn Gly Ile Asp Gly Glu Trp Thr Tyr Asp Asp Ala
        35                  40                  45

Thr Lys Thr Phe Thr Val Thr Glu
    50                  55

<210> SEQ ID NO 44
<211> LENGTH: 56
<212> TYPE: PRT
<213> ORGANISM: Streptococcus sp.

<400> SEQUENCE: 44

Met Thr Phe Lys Leu Ile Ile Asn Gly Lys Thr Leu Lys Gly Glu Thr
  1               5                  10                  15

Thr Thr Glu Ala Val Asp Ala Ala Thr Ala Glu Lys Val Phe Lys Gln
            20                  25                  30

Tyr Ala Asn Asp Asn Gly Ile Asp Gly Glu Trp Thr Tyr Asp Asp Ala
        35                  40                  45

Thr Lys Thr Phe Thr Val Thr Glu
    50                  55

<210> SEQ ID NO 45
<211> LENGTH: 56
<212> TYPE: PRT
<213> ORGANISM: Streptococcus sp.

<400> SEQUENCE: 45

Met Thr Phe Lys Leu Ile Val Asn Gly Lys Thr Leu Lys Gly Glu Thr
```

```
                1               5                      10                         15
         Thr Thr Glu Ala Val Asp Ala Ala Thr Ala Glu Lys Val Phe Lys Gln
                         20                  25                  30

Tyr Ala Asn Asp Asn Gly Ile Asp Gly Glu Trp Thr Tyr Asp Asp Ala
                     35                  40                  45

Thr Lys Thr Phe Thr Val Thr Glu
                     50                  55

<210> SEQ ID NO 46
<211> LENGTH: 56
<212> TYPE: PRT
<213> ORGANISM: Streptococcus sp.

<400> SEQUENCE: 46

Met Thr Phe Lys Leu Ile Ile Asn Gly Lys Thr Leu Lys Gly Glu Thr
          1               5                  10                  15

Thr Thr Glu Ala Val Asp Ala Ala Thr Ala Glu Lys Val Phe Lys Gln
                         20                  25                  30

Tyr Ala Asn Asp Asn Gly Val Asp Gly Glu Trp Thr Tyr Asp Asp Ala
                     35                  40                  45

Thr Lys Thr Phe Thr Val Thr Glu
                     50                  55

<210> SEQ ID NO 47
<211> LENGTH: 56
<212> TYPE: PRT
<213> ORGANISM: Streptococcus sp.

<400> SEQUENCE: 47

Met Thr Ala Lys Ala Ile Ile Asn Gly Lys Thr Leu Lys Gly Glu Thr
          1               5                  10                  15

Thr Thr Glu Ala Val Asp Ala Ala Thr Ala Glu Lys Val Ile Lys Gln
                         20                  25                  30

Tyr Ala Asn Asp Asn Gly Val Asp Gly Glu Trp Thr Tyr Asp Asp Ala
                     35                  40                  45

Thr Lys Thr Ile Thr Ile Thr Glu
                     50                  55

<210> SEQ ID NO 48
<211> LENGTH: 56
<212> TYPE: PRT
<213> ORGANISM: Streptococcus sp.

<400> SEQUENCE: 48

Met Thr Ala Lys Leu Ile Ala Asn Gly Lys Thr Leu Lys Gly Glu Thr
          1               5                  10                  15

Thr Thr Glu Ala Val Asp Ala Ala Thr Ala Glu Lys Val Ala Lys Gln
                         20                  25                  30

Tyr Ala Asn Asp Asn Gly Val Asp Gly Glu Trp Thr Tyr Asp Asp Ala
                     35                  40                  45

Thr Lys Thr Ile Thr Ile Thr Glu
                     50                  55

<210> SEQ ID NO 49
<211> LENGTH: 56
<212> TYPE: PRT
<213> ORGANISM: Streptococcus sp.

<400> SEQUENCE: 49
```

```
Met Thr Ala Lys Ala Ile Ala Asn Gly Lys Thr Leu Lys Gly Glu Thr
 1               5                  10                  15

Thr Thr Glu Ala Val Asp Ala Ala Thr Ala Glu Lys Val Ala Lys Gln
            20                  25                  30

Tyr Ala Asn Asp Asn Gly Val Asp Gly Glu Trp Thr Tyr Asp Asp Ala
            35                  40                  45

Thr Lys Thr Leu Thr Val Thr Glu
        50                  55
```

<210> SEQ ID NO 50
<211> LENGTH: 56
<212> TYPE: PRT
<213> ORGANISM: Streptococcus sp.

<400> SEQUENCE: 50

```
Met Thr Phe Lys Leu Ile Ile Asn Gly Lys Thr Leu Lys Gly Glu Thr
 1               5                  10                  15

Thr Thr Glu Ala Val Asp Ala Ala Thr Ala Glu Lys Val Phe Lys Gln
            20                  25                  30

Tyr Leu Asn Asp Asn Gly Ile Asp Gly Glu Trp Thr Tyr Asp Asp Ala
            35                  40                  45

Thr Lys Thr Trp Thr Phe Thr Glu
        50                  55
```

<210> SEQ ID NO 51
<211> LENGTH: 56
<212> TYPE: PRT
<213> ORGANISM: Streptococcus sp.

<400> SEQUENCE: 51

```
Met Thr Tyr Lys Leu Ile Ile Asn Gly Lys Thr Leu Lys Gly Glu Thr
 1               5                  10                  15

Thr Thr Glu Ala Val Asp Ala Ala Thr Ala Glu Lys Val Phe Lys Gln
            20                  25                  30

Tyr Leu Asn Asp Asn Gly Ile Asp Gly Glu Trp Thr Tyr Asp Asp Ala
            35                  40                  45

Thr Lys Thr Trp Thr Phe Thr Glu
        50                  55
```

<210> SEQ ID NO 52
<211> LENGTH: 56
<212> TYPE: PRT
<213> ORGANISM: Streptococcus sp.

<400> SEQUENCE: 52

```
Met Thr Phe Lys Leu Ile Ile Asn Gly Lys Thr Leu Lys Gly Glu Thr
 1               5                  10                  15

Thr Thr Glu Ala Val Asp Ala Ala Thr Ala Glu Lys Val Phe Lys Gln
            20                  25                  30

Tyr Leu Asn Asp Asn Gly Ile Asp Gly Glu Trp Thr Tyr Asp Asp Ala
            35                  40                  45

Thr Lys Thr Phe Thr Phe Thr Glu
        50                  55
```

<210> SEQ ID NO 53
<211> LENGTH: 56
<212> TYPE: PRT
<213> ORGANISM: Streptococcus sp.

<400> SEQUENCE: 53

```
Met Thr Tyr Lys Leu Ile Ile Asn Gly Lys Thr Leu Lys Gly Glu Thr
 1               5                   10                  15

Thr Thr Glu Ala Val Asp Ala Ala Thr Ala Glu Lys Val Phe Lys Gln
            20                  25                  30

Tyr Leu Asn Asp Asn Gly Ile Asp Gly Glu Trp Thr Tyr Asp Asp Ala
                35                  40                  45

Thr Lys Thr Phe Thr Phe Thr Glu
        50                  55
```

<210> SEQ ID NO 54
<211> LENGTH: 56
<212> TYPE: PRT
<213> ORGANISM: Streptococcus sp.

<400> SEQUENCE: 54

```
Met Thr Phe Lys Leu Ile Ile Asn Gly Lys Thr Leu Lys Gly Glu Thr
 1               5                   10                  15

Thr Thr Glu Ala Val Asp Ala Ala Thr Ala Glu Lys Val Phe Lys Gln
            20                  25                  30

Tyr Leu Asn Asp Asn Gly Val Asp Gly Glu Trp Thr Tyr Asp Asp Ala
                35                  40                  45

Thr Lys Thr Trp Thr Phe Thr Glu
        50                  55
```

<210> SEQ ID NO 55
<211> LENGTH: 56
<212> TYPE: PRT
<213> ORGANISM: Streptococcus sp.

<400> SEQUENCE: 55

```
Met Thr Phe Lys Leu Ile Ile Asn Gly Lys Thr Leu Lys Gly Glu Thr
 1               5                   10                  15

Thr Thr Glu Ala Val Asp Ala Ala Thr Ala Glu Lys Val Phe Lys Gln
            20                  25                  30

Tyr Leu Asn Asp Asn Gly Ile Asp Gly Glu Val Thr Tyr Asp Asp Ala
                35                  40                  45

Thr Lys Thr Trp Thr Phe Thr Glu
        50                  55
```

<210> SEQ ID NO 56
<211> LENGTH: 56
<212> TYPE: PRT
<213> ORGANISM: Streptococcus sp.

<400> SEQUENCE: 56

```
Met Thr Phe Lys Leu Ile Ile Asn Gly Lys Thr Leu Lys Gly Glu Thr
 1               5                   10                  15

Thr Thr Glu Ala Val Asp Ala Ala Thr Ala Glu Lys Val Phe Lys Gln
            20                  25                  30

Tyr Leu Asn Asp Asn Gly Ile Asp Gly Glu Trp Thr Tyr Asp Asp Ala
                35                  40                  45

Thr Lys Thr Tyr Thr Phe Thr Glu
        50                  55
```

<210> SEQ ID NO 57
<211> LENGTH: 56
<212> TYPE: PRT
<213> ORGANISM: Streptococcus sp.

```
<400> SEQUENCE: 57

Met Thr Phe Lys Leu Ile Val Asn Gly Lys Thr Leu Lys Gly Glu Thr
 1               5                  10                  15

Thr Thr Glu Ala Val Asp Ala Ala Thr Ala Glu Lys Val Phe Lys Gln
             20                  25                  30

Tyr Leu Asn Asp Asn Gly Ile Asp Gly Glu Trp Thr Tyr Asp Asp Ala
         35                  40                  45

Thr Lys Thr Trp Thr Phe Thr Glu
     50                  55

<210> SEQ ID NO 58
<211> LENGTH: 56
<212> TYPE: PRT
<213> ORGANISM: Streptococcus sp.

<400> SEQUENCE: 58

Met Thr Phe Lys Leu Ile Ile Asn Gly Lys Thr Leu Lys Gly Glu Thr
 1               5                  10                  15

Thr Thr Glu Ala Val Asp Ala Ala Thr Ala Glu Lys Val Phe Lys Gln
             20                  25                  30

Tyr Ala Asn Asp Asn Gly Ile Asp Gly Glu Trp Thr Tyr Asp Asp Ala
         35                  40                  45

Thr Lys Thr Phe Thr Val Thr Glu
     50                  55

<210> SEQ ID NO 59
<211> LENGTH: 56
<212> TYPE: PRT
<213> ORGANISM: Streptococcus sp.

<400> SEQUENCE: 59

Met Thr Phe Lys Leu Ile Ile Asn Gly Lys Thr Leu Lys Gly Glu Thr
 1               5                  10                  15

Thr Thr Glu Ala Val Asp Ala Ala Thr Ala Glu Lys Val Phe Lys Gln
             20                  25                  30

Tyr Ala Asn Asp Asn Gly Ile Asp Gly Glu Trp Thr Tyr Asp Asp Ala
         35                  40                  45

Thr Lys Thr Trp Thr Val Thr Glu
     50                  55

<210> SEQ ID NO 60
<211> LENGTH: 56
<212> TYPE: PRT
<213> ORGANISM: Streptococcus sp.

<400> SEQUENCE: 60

Met Thr Tyr Lys Leu Ile Ile Asn Gly Lys Thr Leu Lys Gly Glu Thr
 1               5                  10                  15

Thr Thr Glu Ala Val Asp Ala Ala Thr Ala Glu Lys Val Phe Lys Gln
             20                  25                  30

Tyr Leu Asn Asp Asn Gly Val Asp Gly Glu Trp Thr Tyr Asp Asp Ala
         35                  40                  45

Thr Lys Thr Trp Thr Phe Thr Glu
     50                  55

<210> SEQ ID NO 61
<211> LENGTH: 56
<212> TYPE: PRT
<213> ORGANISM: Streptococcus sp.
```

```
<400> SEQUENCE: 61

Met Thr Tyr Lys Leu Ile Ile Asn Gly Lys Thr Leu Lys Gly Glu Thr
 1               5                  10                  15

Thr Thr Glu Ala Val Asp Ala Ala Thr Ala Glu Lys Val Phe Lys Gln
            20                  25                  30

Tyr Leu Asn Asp Asn Gly Ile Asp Gly Glu Val Thr Tyr Asp Asp Ala
        35                  40                  45

Thr Lys Thr Trp Thr Phe Thr Glu
    50                  55

<210> SEQ ID NO 62
<211> LENGTH: 56
<212> TYPE: PRT
<213> ORGANISM: Streptococcus sp.

<400> SEQUENCE: 62

Met Thr Phe Lys Leu Ile Ile Asn Gly Lys Thr Leu Lys Gly Glu Thr
 1               5                  10                  15

Thr Thr Glu Ala Val Asp Ala Ala Thr Ala Glu Lys Val Tyr Lys Gln
            20                  25                  30

Tyr Leu Asn Asp Asn Gly Ile Asp Gly Glu Trp Thr Tyr Asp Asp Ala
        35                  40                  45

Thr Lys Thr Trp Thr Phe Thr Glu
    50                  55

<210> SEQ ID NO 63
<211> LENGTH: 56
<212> TYPE: PRT
<213> ORGANISM: Streptococcus sp.

<400> SEQUENCE: 63

Met Thr Tyr Lys Leu Ile Ile Asn Gly Lys Thr Leu Lys Gly Glu Thr
 1               5                  10                  15

Thr Thr Glu Ala Val Asp Ala Ala Thr Ala Glu Lys Val Phe Lys Gln
            20                  25                  30

Tyr Leu Asn Asp Asn Gly Ile Asp Gly Glu Trp Thr Tyr Asp Asp Ala
        35                  40                  45

Thr Lys Thr Tyr Thr Phe Thr Glu
    50                  55

<210> SEQ ID NO 64
<211> LENGTH: 56
<212> TYPE: PRT
<213> ORGANISM: Streptococcus sp.

<400> SEQUENCE: 64

Met Thr Tyr Lys Leu Ile Ile Asn Gly Lys Thr Leu Lys Gly Glu Thr
 1               5                  10                  15

Thr Thr Glu Ala Val Asp Ala Ala Thr Ala Glu Lys Val Phe Lys Gln
            20                  25                  30

Tyr Leu Asn Asp Asn Gly Ile Asp Gly Glu Trp Thr Tyr Asp Asp Ala
        35                  40                  45

Thr Lys Thr Tyr Thr Phe Thr Glu
    50                  55

<210> SEQ ID NO 65
<211> LENGTH: 56
<212> TYPE: PRT
```

<213> ORGANISM: Streptococcus sp.

<400> SEQUENCE: 65

Met Thr Phe Lys Leu Ile Ile Asn Gly Lys Thr Leu Lys Gly Glu Thr
1               5                   10                  15

Thr Thr Glu Ala Val Asp Ala Ala Thr Ala Glu Lys Val Phe Lys Gln
                20                  25                  30

Tyr Ala Asn Asp Asn Gly Ile Asp Gly Glu Trp Thr Tyr Asp Asp Ala
            35                  40                  45

Thr Lys Thr Phe Thr Ile Thr Glu
    50                  55

<210> SEQ ID NO 66
<211> LENGTH: 56
<212> TYPE: PRT
<213> ORGANISM: Streptococcus sp.

<400> SEQUENCE: 66

Met Thr Phe Lys Leu Ile Ile Asn Gly Lys Thr Leu Lys Gly Glu Thr
1               5                   10                  15

Thr Thr Glu Ala Val Asp Ala Ala Thr Ala Glu Lys Val Phe Lys Gln
                20                  25                  30

Tyr Ile Asn Asp Asn Gly Ile Asp Gly Glu Trp Thr Tyr Asp Asp Ala
            35                  40                  45

Thr Lys Thr Phe Thr Val Thr Glu
    50                  55

<210> SEQ ID NO 67
<211> LENGTH: 56
<212> TYPE: PRT
<213> ORGANISM: Streptococcus sp.

<400> SEQUENCE: 67

Met Thr Phe Lys Ile Ile Phe Asn Gly Lys Thr Leu Lys Gly Glu Thr
1               5                   10                  15

Thr Thr Glu Ala Val Asp Ala Ala Thr Ala Glu Lys Val Phe Lys Gln
                20                  25                  30

Tyr Ala Asn Asp Asn Gly Ile Asp Gly Glu Trp Thr Tyr Asp Asp Ala
            35                  40                  45

Thr Lys Thr Phe Thr Val Thr Glu
    50                  55

<210> SEQ ID NO 68
<211> LENGTH: 56
<212> TYPE: PRT
<213> ORGANISM: Streptococcus sp.

<400> SEQUENCE: 68

Met Thr Tyr Lys Leu Ile Ile Asn Gly Lys Thr Leu Lys Gly Glu Thr
1               5                   10                  15

Thr Thr Glu Ala Val Asp Ala Ala Thr Ala Glu Lys Val Phe Lys Gln
                20                  25                  30

Tyr Ala Asn Asp Asn Gly Ile Asp Gly Glu Trp Thr Tyr Asp Asp Ala
            35                  40                  45

Thr Lys Thr Phe Thr Ile Thr Glu
    50                  55

<210> SEQ ID NO 69
<211> LENGTH: 56

```
<212> TYPE: PRT
<213> ORGANISM: Streptococcus sp.

<400> SEQUENCE: 69

Met Thr Tyr Lys Leu Ile Ile Asn Gly Lys Thr Leu Lys Gly Glu Thr
 1               5                  10                  15

Thr Thr Glu Ala Val Asp Ala Ala Thr Ala Glu Lys Val Phe Lys Gln
            20                  25                  30

Tyr Ile Asn Asp Asn Gly Ile Asp Gly Glu Trp Thr Tyr Asp Asp Ala
        35                  40                  45

Thr Lys Thr Phe Thr Val Thr Glu
    50                  55

<210> SEQ ID NO 70
<211> LENGTH: 56
<212> TYPE: PRT
<213> ORGANISM: Streptococcus sp.

<400> SEQUENCE: 70

Met Thr Tyr Lys Ile Ile Phe Asn Gly Lys Thr Leu Lys Gly Glu Thr
 1               5                  10                  15

Thr Thr Glu Ala Val Asp Ala Ala Thr Ala Glu Lys Val Phe Lys Gln
            20                  25                  30

Tyr Ala Asn Asp Asn Gly Ile Asp Gly Glu Trp Thr Tyr Asp Asp Ala
        35                  40                  45

Thr Lys Thr Phe Thr Val Thr Glu
    50                  55

<210> SEQ ID NO 71
<211> LENGTH: 56
<212> TYPE: PRT
<213> ORGANISM: Streptococcus sp.

<400> SEQUENCE: 71

Met Thr Phe Lys Leu Ile Ile Asn Gly Lys Thr Leu Lys Gly Glu Thr
 1               5                  10                  15

Thr Thr Glu Ala Val Asp Ala Ala Thr Ala Glu Lys Val Phe Lys Gln
            20                  25                  30

Tyr Leu Asn Asp Asn Gly Ile Asp Gly Glu Trp Thr Tyr Asp Asp Ala
        35                  40                  45

Thr Lys Thr Trp Thr Phe Thr Glu
    50                  55

<210> SEQ ID NO 72
<211> LENGTH: 56
<212> TYPE: PRT
<213> ORGANISM: Streptococcus sp.

<400> SEQUENCE: 72

Met Thr Phe Lys Leu Ile Ile Asn Gly Lys Thr Leu Lys Gly Glu Thr
 1               5                  10                  15

Thr Thr Glu Ala Val Asp Ala Ala Thr Ala Glu Lys Val Phe Lys Gln
            20                  25                  30

Tyr Leu Asn Asp Asn Gly Ile Asp Gly Glu Ile Thr Tyr Asp Asp Ala
        35                  40                  45

Thr Lys Thr Phe Thr Phe Thr Glu
    50                  55

<210> SEQ ID NO 73
```

<211> LENGTH: 56
<212> TYPE: PRT
<213> ORGANISM: Streptococcus sp.

<400> SEQUENCE: 73

Met Thr Tyr Lys Leu Ile Ile Asn Gly Lys Thr Leu Lys Gly Glu Thr
 1               5                  10                  15

Thr Thr Glu Ala Val Asp Ala Ala Thr Ala Glu Lys Val Phe Lys Gln
            20                  25                  30

Tyr Ala Asn Asp Asn Gly Val Asp Gly Glu Ile Thr Tyr Asp Asp Ala
        35                  40                  45

Thr Lys Thr Phe Thr Val Thr Glu
    50                  55

<210> SEQ ID NO 74
<211> LENGTH: 56
<212> TYPE: PRT
<213> ORGANISM: Streptococcus sp.

<400> SEQUENCE: 74

Met Thr Phe Lys Leu Ile Ile Asn Gly Lys Thr Leu Lys Gly Glu Thr
 1               5                  10                  15

Thr Thr Glu Ala Val Asp Ala Ala Thr Ala Glu Lys Val Phe Lys Gln
            20                  25                  30

Tyr Ala Asn Asp Asn Gly Ile Asp Gly Glu Trp Thr Tyr Asp Asp Ala
        35                  40                  45

Thr Lys Thr Phe Thr Val Thr Glu
    50                  55

<210> SEQ ID NO 75
<211> LENGTH: 56
<212> TYPE: PRT
<213> ORGANISM: Streptococcus sp.

<400> SEQUENCE: 75

Met Thr Tyr Lys Leu Ile Ile Asn Gly Lys Thr Leu Lys Gly Glu Thr
 1               5                  10                  15

Thr Thr Glu Ala Val Asp Ala Ala Thr Ala Glu Lys Val Phe Lys Gln
            20                  25                  30

Tyr Leu Asn Asp Asn Gly Ile Asp Gly Glu Trp Thr Tyr Asp Asp Ala
        35                  40                  45

Thr Lys Thr Trp Thr Phe Thr Glu
    50                  55

<210> SEQ ID NO 76
<211> LENGTH: 56
<212> TYPE: PRT
<213> ORGANISM: Streptococcus sp.

<400> SEQUENCE: 76

Met Thr Tyr Lys Leu Ile Ile Asn Gly Lys Thr Leu Lys Gly Glu Thr
 1               5                  10                  15

Thr Thr Glu Ala Val Asp Ala Ala Thr Ala Glu Lys Val Phe Lys Gln
            20                  25                  30

Tyr Leu Asn Asp Asn Gly Ile Asp Gly Glu Trp Thr Tyr Asp Asp Ala
        35                  40                  45

Thr Lys Thr Trp Thr Phe Thr Glu
    50                  55

-continued

```
<210> SEQ ID NO 77
<211> LENGTH: 56
<212> TYPE: PRT
<213> ORGANISM: Streptococcus sp.

<400> SEQUENCE: 77

Met Thr Phe Lys Leu Ile Ile Asn Gly Lys Thr Leu Lys Gly Glu Thr
 1               5                  10                  15

Thr Thr Glu Ala Val Asp Ala Ala Thr Ala Glu Lys Val Phe Lys Gln
             20                  25                  30

Tyr Leu Asn Asp Asn Gly Ile Asp Gly Glu Val Thr Tyr Asp Asp Ala
         35                  40                  45

Thr Lys Thr Trp Thr Phe Thr Glu
     50                  55

<210> SEQ ID NO 78
<211> LENGTH: 56
<212> TYPE: PRT
<213> ORGANISM: Streptococcus sp.

<400> SEQUENCE: 78

Met Thr Tyr Lys Leu Ile Ile Asn Gly Lys Thr Leu Lys Gly Glu Thr
 1               5                  10                  15

Thr Thr Glu Ala Val Asp Ala Ala Thr Ala Glu Lys Val Phe Lys Gln
             20                  25                  30

Tyr Leu Asn Asp Asn Gly Ile Asp Gly Glu Ile Thr Tyr Asp Asp Ala
         35                  40                  45

Thr Lys Thr Phe Thr Phe Thr Glu
     50                  55

<210> SEQ ID NO 79
<211> LENGTH: 56
<212> TYPE: PRT
<213> ORGANISM: Streptococcus sp.

<400> SEQUENCE: 79

Met Thr Phe Lys Leu Ile Ile Asn Gly Lys Thr Leu Lys Gly Glu Thr
 1               5                  10                  15

Thr Thr Glu Ala Val Asp Ala Ala Thr Ala Glu Lys Val Phe Lys Gln
             20                  25                  30

Tyr Ala Asn Asp Asn Gly Ile Asp Gly Glu Trp Thr Tyr Asp Asp Ala
         35                  40                  45

Thr Lys Thr Tyr Thr Ile Thr Glu
     50                  55
```

APPARATUS AND METHOD FOR AUTOMATED PROTEIN DESIGN

This application claims the benefit of U.S. provisional applications U.S. Ser. No. 60/043,464, filed Apr. 11, 1997, 60/054,678, filed Aug. 4, 1997, and 60/061,097, filed Oct. 3, 1997.

FIELD OF THE INVENTION

The present invention relates to an apparatus and method for quantitative protein design and optimization.

BACKGROUND OF THE INVENTION

De novo protein design has received considerable attention recently, and significant advances have been made toward the goal of producing stable, well-folded proteins with novel sequences. Efforts to design proteins rely on knowledge of the physical properties that determine protein structure, such as the patterns of hydrophobic and hydrophilic residues in the sequence, salt bridges and hydrogen bonds, and secondary structural preferences of amino acids. Various approaches to apply these principles have been attempted. For example, the construction of α-helical and β-sheet proteins with native-like sequences was attempted by individually selecting the residue required at every position in the target fold (Hecht, et al., *Science* 249:884–891 (1990); Quinn, et al., *Proc. Nati. Acad. Sci USA* 91:8747–8751 (1994)). Alternatively, a minimalist approach was used to design helical proteins, where the simplest possible sequence believed to be consistent with the folded structure was generated (Regan, et al., *Science* 241:976–978 (1988); DeGrado, et al., *Science* 243:622–628 (1989); Handel, et al., *Science* 261:879–885 (1993)), with varying degrees of success. An experimental method that relies on the hydrophobic and polar (HP) pattern of a sequence was developed where a library of sequences with the correct pattern for a four helix bundle was generated by random mutagenesis (Kamtekar, et al., *Science* 262:1680–1685 (1993)). Among non de novo approaches, domains of naturally occurring proteins have been modified or coupled together to achieve a desired tertiary organization (Pessi, et al., *Nature* 362:367–369 (1993); Pomerantz, et al., *Science* 267:93–96 (1995)).

Though the correct secondary structure and overall tertiary organization seem to have been attained by several of the above techniques, many designed proteins appear to lack the structural specificity of native proteins. The complementary geometric arrangement of amino acids in the folded protein is the root of this specificity and is encoded in the sequence.

Several groups have applied and experimentally tested systematic, quantitative methods to protein design with the goal of developing general design algorithms (Hellinga, et al., *J. Mol. Biol.* 222: 763–785 (1991); Hurley, et al., *J. Mol. Biol.* 224:1143–1154 (1992); Desjarlaisl, et al., *Protein Science* 4:2006–2018 (1995); Harbury, et al., *Proc. Natl. Acad. Sci. USA* 92:8408–8412 (1995); Klemba, et al., *Nat. Struc. Biol.* 2:368–373 (1995); Nautiyal, et al., *Biochemistry* 34:11645–11651 (1995); Betzo, et al., *Biochemistry* 35:6955–6962 (1996); Dahiyat, et al., *Protein Science* 5:895–903 (1996); Jones, *Protein Science* 3:567–574 (1994); Konoi, et al., *Proteins: Structure, Function and Genetics* 19:244–255 (1994)). These algorithms consider the spatial positioning and steric complementarity of side chains by explicitly modeling the atoms of sequences under consideration. To date, such techniques have typically focused on designing the cores of proteins and have scored sequences with van der Waals and sometimes hydrophobic solvation potentials.

In addition, the qualitative nature of many design approaches has hampered the development of improved, second generation, proteins because there are no objective methods for learning from past design successes and failures.

Thus, it is an object of the invention to provide computational protein design and optimization via an objective, quantitative design technique implemented in connection with a general purpose computer.

SUMMARY OF THE INVENTION

In accordance with the objects outlined above, the present invention provides methods executed by a computer under the control of a program, the computer including a memory for storing the program. The method comprising the steps of receiving a protein backbone structure with variable residue positions, establishing a group of potential rotamers for each of the variable residue positions, wherein at least one variable residue position has rotamers from at least two different amino acid side chains, and analyzing the interaction of each of the rotamers with all or part of the remainder of the protein backbone structure to generate a set of optimized protein sequences. The methods further comprise classifying each variable residue position as either a core, surface or boundary residue. The analyzing step may include a Dead-End Elimination (DEE) computation. Generally, the analyzing step includes the use of at least one scoring function selected from the group consisting of a Van der Waals potential scoring function, a hydrogen bond potential scoring function, an atomic solvation scoring function, a secondary structure propensity scoring function and an electrostatic scoring function. The methods may further comprise generating a rank ordered list of additional optimal sequences from the globally optimal protein sequence. Some or all of the protein sequences from the ordered list may be tested to produce potential energy test results.

In an additional aspect, the invention provides nucleic acid sequences encoding a protein sequence generated by the present methods, and expression vectors and host cells containing the nucleic acids.

In a further aspect, the invention provides a computer readable memory to direct a computer to function in a specified manner, comprising a side chain module to correlate a group of potential rotamers for residue positions of a protein backbone model, and a ranking module to analyze the interaction of each of said rotamers with all or part of the remainder of said protein to generate a set of optimized protein sequences. The memory may further comprise an assessment module to assess the correspondence between potential energy test results and theoretical potential energy data.

BRIEF DESCRIPTION OF THE DRAWINGS

FIG. 1 illustrates a general purpose computer configured in accordance with an embodiment of the invention.

FIG. 2 illustrates processing steps associated with an embodiment of the invention.

FIG. 3 illustrates processing steps associated with a ranking module used in accordance with an embodiment of the invention. After any DEE step, any one of the previous DEE steps may be repeated. In addition, any one of the DEE steps may be eliminated; for example, original singles DEE (step 74) need not be run.

FIG. 4 depicts the protein design automation cycle.

FIG. 5 depicts the helical wheel diagram of a coiled coil. One heptad repeat is shown viewed down the major axes of the helices. The a and d positions define the solvent-inaccessible core of the molecule (Cohen & Parry, 1990, Proteins, Structure, Function and Genetics 7:1–15).

FIGS. 6A and 6B depict the comparison of simulation cost functions to experimental Tm's. FIG. 6A depicts the initial cost function, which contains only a van der Waals term for the eight PDA peptides. FIG. 6B depicts the improved cost function containing polar and nonpolar surface area terms weighted by atomic solvation parameters derived from QSAR analysis; 16 cal/mol/Å² favors hydrophobic surface burial.

FIG. 7 shows the rank correlation of energy predicted by the simulation module versus the combined activity score of λ repressor mutants (Lim , et al., *J. Mol. Biol.* 219:359–376 (1991); Hellinga, et al., *Proc. Natl. Acad. Sci. USA* 91:5803–5807 (1994)).

FIG. 8 shows the sequence of pda8d (SEQ ID NO:2) aligned with the second zinc finger of Zif268 (SEQ ID NO:1). The boxed positions were designed using the sequence selection algorithm. The coordinates of PDB record 1zaa (Paveletch, et al., *Science* 252:809–817 (1991)) from residues 33–60 were used as the structure template. In our numbering, position 1 corresponds to 1 zaa position 33.

FIGS. 9A and 9B shows the NMR spectra and solution secondary structure of pda8d from Example 3. FIG. 9A is the TOCSY Hα-HN fingerprint region of pda8d. FIG. 9B is the NMR NOE connectivities of pda8d. Bars represent unambiguous connectivities and the bar thickness of the sequential connections is indexed to the intensity of the resonance.

FIGS. 10A and 10B depict the secondary structure content and thermal stability of α90, α85, α70 and α107. FIG. 10A depicts the far UV spectra (circular dichroism). FIG. 10B depicts the thermal denaturation monitored by CD.

FIG. 11 depicts the sequence of FSD-1 (SEQ ID NO:3) of Example 5 aligned with the second zinc finger of Zif268 (SEQ ID NO:1). The bar at the top of the figure shows the residue position classifications: solid bars indicate core positions, hatched bars indicate boundary positions and open bars indicate surface positions. The alignment matches positions of FSD-1 (SEQ ID NO:3) to the corresponding backbone template positions of Zif268 (SEQ ID NO:1). Of the six identical positions (21%) between FSD-1 (SEQ ID NO:3) and Zif268 (SEQ ID NO:1), four are buried (Ile7, Phe12, Leu18 and Ile22). The zinc binding residues of Zif268 (SEQ ID NO:1) are boxed. Representative non-optimal sequence solutions determined using a Monte Carlo simulated annealing protocol are shown with their rank (SEQ ID NOS:4 to 22). Vertical lines indicate identity with FSD-1 (SEQ ID NO:3). The symbols at the bottom the figure show the degee of sequence conservation for each residue position computed across the top 1000 sequences: filled circles indicate greater than 99% conservation, half-filled circles indicate conservation between 90 and 99%, open circles indicate conservation between 50 and 90%, and the absence of symbol indicates less than 50% conservation. The consensus sequence determined by choosing the amino acid with the highest occurrence at each position is identical to the sequence of FSD-1 (SEQ ID NO: 3).

FIG. 12 is a schematic representation of the minimum and maximum quantities (defined in Eq. 24 to 27) that are used to construct speed enhancements. The minima and maxima are utilized directly to find the $|i_u j_v|_{mb}$ pair and for the comparison of extrema. The differences between the quantities, denoted with arrows, are used to construct the $q_{rs}$ and $q_{uv}$ metrics.

FIGS. 13A, 13B, 13C, 13D, 13E and 13F depicts the areas involved in calculating the buried and exposed areas of Equations 18 and 19. The dashed box is the protein template, the heavy solid lines correspond to three rotamers at three different residue positions, and the lighter solid lines correspond to surface areas. a) $A^O_{i,t3}$ for each rotamer. b) $A_{i,t}$ for each rotamer. c) $(A^O_{i,t3}-A_{i,t})$ summed over the three residues. The upper residue does not bury any area against the template except that buried in the tri-peptide state $A^O_{i,t3}$.d) $A_{i,j,t}$ for one pair of rotamers. e) The area buried between rotamers, $(A_{i,t}+A_{j,t}-A_{i,j,t})$, for the same pair of rotamers as in (d). f) The area buried between rotamers, $(A_{i,t}+A_{j,t}-A_{i,j,t})$, summed over the three pairs of rotamers. The area b intersected by all three rotamers is counted twice and is indicated by the double lines. The buried area calculated by Equation 18 is the area buried by the template, represented in (c), plus s times the area buried between rotamers, represented in (f). The scaling factor s accounts for the over-counting shown by the double lines in (f). The exposed area calculated by Equation 19 is the exposed are in the presence of the template, represented in (b), minus s times the area buried between rotamers, represented in (f).

DETAILED DESCRIPTION OF THE INVENTION

The present invention is directed to the quantitative design and optimization of amino acid sequences, using an "inverse protein folding" approach, which seeks the optimal sequence for a desired structure. Inverse folding is similar to protein design, which seeks to find a sequence or set of sequences that will fold into a desired structure. These approaches can be contrasted with a "protein folding" approach which attempts to predict a structure taken by a given sequence.

The general preferred approach of the present invention is as follows, although alternate embodiments are discussed below. A known protein structure is used as the starting point. The residues to be optimized are then identified, which may be the entire sequence or subset(s) thereof. The side chains of any positions to be varied are then removed. The resulting structure consisting of the protein backbone and the remaining sidechains is called the template. Each variable residue position is then preferably classified as a core residue, a surface residue, or a boundary residue; each classification defines a subset of possible amino acid residues for the position (for example, core residues generally will be selected from the set of hydrophobic residues, surface residues generally will be selected from the hydrophilic residues, and boundary residues may be either). Each amino acid can be represented by a discrete set of all allowed conformers of each side chain, called rotamers. Thus, to arrive at an optimal sequence for a backbone, all possible sequences of rotamers must be screened, where each backbone position can be occupied either by each amino acid in all its possible rotameric states, or a subset of amino acids, and thus a subset of rotamers.

Two sets of interactions are then calculated for each rotamer at every position: the interaction of the rotamer side chain with all or part of the backbone (the "singles" energy, also called the rotamer/template or rotamer/backbone energy), and the interaction of the rotamer side chain with all other possible rotamers at every other position or a subset of the other positions (the "doubles" energy, also called the rotamer/rotamer energy). The energy of each of these interactions is calculated through the use of a variety of scoring functions, which include the energy of van der Waal's forces, the energy of hydrogen bonding, the energy of secondary structure propensity, the energy of surface area solvation and the electrostatics. Thus, the total energy of each rotamer interaction, both with the backbone and other rotamers, is calculated, and stored in a matrix form.

The discrete nature of rotamer sets allows a simple calculation of the number of rotamer sequences to be tested. A backbone of length n with m possible rotamers per position will have $m^n$ possible rotamer sequences, a number which grows exponentially with sequence length and renders the calculations either unwieldy or impossible in real time. Accordingly, to solve this combinatorial search problem, a "Dead End Elimination" (DEE) calculation is performed. The DEE calculation is based on the fact that if the worst total interaction of a first rotamer is still better than the best total interaction of a second rotamer, then the second rotamer cannot be part of the global optimum solution. Since the energies of all rotamers have already been calculated, the DEE approach only requires sums over the sequence length to test and eliminate rotamers, which speeds up the calculations considerably. DEE can be rerun comparing pairs of rotamers, or combinations of rotamers, which will eventually result in the determination of a single sequence which represents the global optimum energy.

Once the global solution has been found, a Monte Carlo search may be done to generate a rank-ordered list of sequences in the neighborhood of the DEE solution. Starting at the DEE solution, random positions are changed to other rotamers, and the new sequence energy is calculated. If the new sequence meets the criteria for acceptance, it is used as a starting point for another jump. After a predetermined number of jumps, a rank-ordered list of sequences is generated.

The results may then be experimentally verified by physically generating one or more of the protein sequences followed by experimental testing. The information obtained from the testing can then be fed back into the analysis, to modify the procedure if necessary.

Thus, the present invention provides a computer-assisted method of designing a protein. The method comprises providing a protein backbone structure with variable residue positions, and then establishing a group of potential rotamers for each of the residue positions. As used herein, the backbone, or template, includes the backbone atoms and any fixed side chains. The interactions between the protein backbone and the potential rotamers, and between pairs of the potential rotamers, are then processed to generate a set of optimized protein sequences, preferably a single global optimum, which then may be used to generate other related sequences.

FIG. 1 illustrates an automated protein design apparatus 20 in accordance with an embodiment of the invention. The apparatus 20 includes a central processing unit 22 which communicates with a memory 24 and a set of input/output devices (e.g., keyboard, mouse, monitor, printer, etc.) 26 through a bus 28. The general interaction between a central processing unit 22, a memory 24, input/output devices 26, and a bus 28 is known in the art. The present invention is directed toward the automated protein design program 30 stored in the memory 24.

The automated protein design program 30 may be implemented with a side chain module 32. As discussed in detail below, the side chain module establishes a group of potential rotamers for a selected protein backbone structure. The protein design program 30 may also be implemented with a ranking module 34. As discussed in detail below, the ranking module 34 analyzes the interaction of rotamers with the protein backbone structure to generate optimized protein sequences. The protein design program 30 may also include a search module 36 to execute a search, for example a Monte Carlo search as described below, in relation to the optimized protein sequences. Finally, an assessment module 38 may also be used to assess physical parameters associated with the derived proteins, as discussed further below.

The memory 24 also stores a protein backbone structure 40, which is downloaded by a user through the input/output devices 26. The memory 24 also stores information on potential rotamers derived by the side chain module 32. In addition, the memory 24 stores protein sequences 44 generated by the ranking module 34. The protein sequences 44 may be passed as output to the input/output devices 26.

The operation of the automated protein design apparatus 20 is more fully appreciated with reference to FIG. 2. FIG. 2 illustrates processing steps executed in accordance with the method of the invention. As described below, many of the processing steps are executed by the protein design program 30. The first processing step illustrated in FIG. 2 is to provide a protein backbone structure (step 50). As previously indicated, the protein backbone structure is downloaded through the input/output devices 26 using standard techniques.

The protein backbone structure corresponds to a selected protein. By "protein" herein is meant at least two amino acids linked together by a peptide bond. As used herein, protein includes proteins, oligopeptides and peptides. The peptidyl group may comprise naturally occurring amino acids and peptide bonds, or synthetic peptidomimetic structures, i.e. "analogs", such as peptoids (see Simon et al., *PNAS USA* 89(20):9367 (1992)). The amino acids may either be naturally occuring or non-naturally occuring; as will be appreciated by those in the art, any structure for which a set of rotamers is known or can be generated can be used as an amino acid. The side chains may be in either the (R) or the (S) configuration. In a preferred embodiment, the amino acids are in the (S) or L-configuration.

The chosen protein may be any protein for which a three dimensional structure is known or can be generated; that is, for which there are three dimensional coordinates for each atom of the protein. Generally this can be determined using X-ray crystallographic techniques, NMR techniques, de novo modelling, homology modelling, etc. In general, if X-ray structures are used, structures at 2 Å resolution or better are preferred, but not required.

The proteins may be from any organism, including prokaryotes and eukaryotes, with enzymes from bacteria, fungi, extremeophiles such as the archebacteria, insects, fish, animals (particularly mammals and particularly human) and birds all possible.

Suitable proteins include, but are not limited to, industrial and pharmaceutical proteins, including ligands, cell surface receptors, antigens, antibodies, cytokines, hormones, and enzymes. Suitable classes of enzymes include, but are not limited to, hydrolases such as proteases, carbohydrases, lipases; isomerases such as racemases, epimerases, tautomerases, or mutases; transferases, kinases, oxidoreductases, and phophatases. Suitable enzymes are listed in the Swiss-Prot enzyme database.

Suitable protein backbones include, but are not limited to, all of those found in the protein data base compiled and serviced by the Brookhaven National Lab.

Specifically included within "protein" are fragments and domains of known proteins, including functional domains such as enzymatic domains, binding domains, etc., and smaller fragments, such as turns, loops, etc. That is, portions of proteins may be used as well.

Once the protein is chosen, the protein backbone structure is input into the computer. By "protein backbone structure" or grammatical equivalents herein is meant the three dimensional coordinates that define the three dimensional structure of a particular protein. The structures which comprise a protein backbone structure (of a naturally occuring protein) are the nitrogen, the carbonyl carbon, the α-carbon, and the carbonyl oxygen, along with the direction of the vector from the α-carbon to the β-carbon.

The protein backbone structure which is input into the computer can either include the coordinates for both the backbone and the amino acid side chains, or just the backbone, i.e. with the coordinates for the amino acid side chains removed. If the former is done, the side chain atoms of each amino acid of the protein structure may be "stripped" or removed from the structure of a protein, as is known in the art, leaving only the coordinates for the "backbone" atoms (the nitrogen, carbonyl carbon and oxygen, and the α-carbon, and the hydrogens attached to the nitrogen and α-carbon).

After inputing the protein structure backbone, explicit hydrogens are added if not included within the structure (for example, if the structure was generated by X-ray crystallography, hydrogens must be added). After hydrogen addition, energy minimization of the structure is run, to relax the hydrogens as well as the other atoms, bond angles and bond lengths. In a preferred embodiment, this is done by doing a number of steps of conjugate gradient minimization (Mayo et al., *J. Phys. Chem.* 94:8897 (1990)) of atomic coordinate positions to minimize the Dreiding force field with no electrostatics. Generally from about 10 to about 250 steps is preferred, with about 50 being most preferred.

The protein backbone structure contains at least one variable residue position. As is known in the art, the residues, or amino acids, of proteins are generally sequentially numbered starting with the N-terminus of the protein. Thus a protein having a methionine at it's N-terminus is said to have a methionine at residue or amino acid position 1, with the next residues as 2, 3, 4, etc. At each position, the wild type (i.e. naturally occuring) protein may have one of at least 20 amino acids, in any number of rotamers. By "variable residue position" herein is meant an amino acid position of the protein to be designed that is not fixed in the design method as a specific residue or rotamer, generally the wild-type residue or rotamer.

In a preferred embodiment, all of the residue positions of the protein are variable. That is, every amino acid side chain may be altered in the methods of the present invention. This is particularly desirable for smaller proteins, although the present methods allow the design of larger proteins as well. While there is no theoretical limit to the length of the protein which may be designed this way, there is a practical computational limit.

In an alternate preferred embodiment, only some of the residue positions of the protein are variable, and the remainder are "fixed", that is, they are identified in the three dimensional structure as being in a set conformation. In some embodiments, a fixed position is left in its original conformation (which may or may not correlate to a specific rotamer of the rotamer library being used). Alternatively, residues may be fixed as a non-wild type residue; for example, when known site-directed mutagenesis techniques have shown that a particular residue is desirable (for example, to eliminate a proteolytic site or alter the substrate specificity of an enzyme), the residue may be fixed as a particular amino acid. Alternatively, the methods of the present invention may be used to evaluate mutations de novo, as is discussed below. In an alternate preferred embodiment, a fixed position may be "floated"; the amino acid at that position is fixed, but different rotamers of that amino acid are tested. In this embodiment, the variable residues may be at least one, or anywhere from 0.1% to 99.9% of the total number of residues. Thus, for example, it may be possible to change only a few (or one) residues, or most of the residues, with all possibilities in between.

In a preferred embodiment, residues which can be fixed include, but are not limited to, structurally or biologically functional residues. For example, residues which are known to be important for biological activity, such as the residues which form the active site of an enzyme, the substrate binding site of an enzyme, the binding site for a binding partner (ligand/receptor, antigen/antibody, etc.), phosphorylation or glycosylation sites which are crucial to biological function, or structurally important residues, such as disulfide bridges, met al binding sites, critical hydrogen bonding residues, residues critical for backbone conformation such as proline or glycine, residues critical for packing interactions, etc. may all be fixed in a conformation or as a single rotamer, or "floated".

Similarly, residues which may be chosen as variable residues may be those that confer undesirable biological attributes, such as susceptibility to proteolytic degradation, dimerization or aggregation sites, glycosylation sites which may lead to immune responses, unwanted binding activity, unwanted allostery, undesirable enzyme activity but with a preservation of binding, etc.

As will be appreciated by those in the art, the methods of the present invention allow computational testing of "site-directed mutagenesis" targets without actually making the mutants, or prior to making the mutants. That is, quick analysis of sequences in which a small number of residues are changed can be done to evaluate whether a proposed change is desirable. In addition, this may be done on a known protein, or on an protein optimized as described herein.

As will be appreciated by those in the art, a domain of a larger protein may essentially be treated as a small independent protein; that is, a structural or functional domain of a large protein may have minimal interactions with the remainder of the protein and may essentially be treated as if it were autonomous. In this embodiment, all or part of the residues of the domain may be variable.

It should be noted that even if a position is chosen as a variable position, it is possible that the methods of the invention will optimize the sequence in such a way as to select the wild type residue at the variable position. This generally occurs more frequently for core residues, and less regularly for surface residues. In addition, it is possible to fix residues as non-wild type amino acids as well.

Once the protein backbone structure has been selected and input, and the variable residue positions chosen, a group of potential rotamers for each of the variable residue positions is established. This operation is shown as step 52 in FIG. 2. This step may be implemented using the side chain module 32. In one embodiment of the invention, the side chain module 32 includes at least one rotamer library, as described below, and program code that correlates the selected protein backbone structure with corresponding information in the rotamer library. Alternatively, the side chain module 32 may be omitted and the potential rotamers 42 for the selected protein backbone structure may be downloaded through the input/output devices 26.

As is known in the art, each amino acid side chain has a set of possible conformers, called rotamers. See Ponder, et al., Acad. Press Inc. (London) Ltd. pp. 775–791 (1987); Dunbrack, et al., Struc. Biol. 1(5):334–340 (1994); Desmet, et al., Nature 356:539–542 (1992), all of which are hereby expressly incorporated by reference in their entireity. Thus, a set of discrete rotamers for every amino acid side chain is used. There are two general types of rotamer libraries: backbone dependent and backbone independent. A backbone dependent rotamer library allows different rotamers depending on the position of the residue in the backbone; thus for example, certain leucine rotamers are allowed if the position is within an a helix, and different leucine rotamers are allowed if the position is not in a α-helix. A backbone independent rotamer library utilizes all rotamers of an amino acid at every position. In general, a backbone independent library is preferred in the consideration of core residues, since flexibility in the core is important. However, backbone independent libraries are computationally more expensive, and thus for surface and boundary positions, a backbone dependent library is preferred. However, either type of library can be used at any position.

In addition, a preferred embodiment does a type of "fine tuning" of the rotamer library by expanding the possible X (chi) angle values of the rotamers by plus and minus one standard deviation (or more) about the mean value, in order to minimize possible errors that might arise from the discreteness of the library. This is particularly important for aromatic residues, and fairly important for hydrophobic residues, due to the increased requirements for flexibility in the core and the rigidity of aromatic rings; it is not as important for the other residues. Thus a preferred embodiment expands the $X_1$ and $X_2$ angles for all amino acids except Met, Arg and Lys.

To roughly illustrate the numbers of rotamers, in one version of the Dunbrack & Karplus backbone-dependent rotamer library, alanine has 1 rotamer, glycine has 1 rotamer, arginine has 55 rotamers, threonine has 9 rotamers, lysine has 57 rotamers, glutamic acid has 69 rotamers, asparagine has 54 rotamers, aspartic acid has 27 rotamers, tryptophan has 54 rotamers, tyrosine has 36 rotamers, cysteine has 9 rotamers, glutamine has 69 rotamers, histidine has 54 rotamers, valine has 9 rotamers, isoleucine has 45 rotamers, leucine has 36 rotamers, methionine has 21 rotamers, serine has 9 rotamers, and phenylalanine has 36 rotamers.

In general, proline is not generally used, since it will rarely be chosen for any position, although it can be included if desired. Similarly, a preferred embodiment omits cysteine as a consideration, only to avoid potential disulfide problems, although it can be included if desired.

As will be appreciated by those in the art, other rotamer libraries with all dihedral angles staggered can be used or generated.

In a preferred embodiment, at a minimum, at least one variable position has rotamers from at least two different amino acid side chains; that is, a sequence is being optimized, rather than a structure.

In a preferred embodiment, rotamers from all of the amino acids (or all of them except cysteine, glycine and proline) are used for each variable residue position; that is, the group or set of potential rotamers at each variable position is every possible rotamer of each amino acid. This is especially preferred when the number of variable positions is not high as this type of analysis can be computationally expensive.

In a preferred embodiment, each variable position is classified as either a core, surface or boundary residue position, although in some cases, as explained below, the variable position may be set to glycine to minimize backbone strain.

It should be understood that quantitative protein design or optimization studies prior to the present invention focused almost exclusively on core residues. The present invention, however, provides methods for designing proteins containing core, surface and boundary positions. Alternate embodiments utilize methods for designing proteins containing core and surface residues, core and boundary residues, and surface and boundary residues, as well as core residues alone (using the scoring functions of the present invention), surface residues alone, or boundary residues alone.

The classification of residue positions as core, surface or boundary may be done in several ways, as will be appreciated by those in the art. In a preferred embodiment, the classification is done via a visual scan of the original protein backbone structure, including the side chains, and assigning a classification based on a subjective evaluation of one skilled in the art of protein modelling. Alternatively, a preferred embodiment utilizes an assessment of the orientation of the Cα–Cβ vectors relative to a solvent accessible surface computed using only the template Cα atoms. In a preferred embodiment, the solvent accessible surface for only the Cα atoms of the target fold is generated using the Connolly algorithm with a probe radius ranging from about 4 to about 12 Å, with from about 6 to about 10 Å being preferred, and 8 Å being particularly preferred. The Cα radius used ranges from about 1.6 Å to about 2.3 Å, with from about 1.8 to about 2.1 Å being preferred, and 1.95 Å being especially preferred. A residue is classified as a core position if a) the distance for its Cα, along its Cα–Cβ vector, to the solvent accessible surface is greater than about 4–6 Å, with greater than about 5.0 Å being especially preferred, and b) the distance for its Cβ to the nearest surface point is greater than about 1.5–3 Å, with greater than about 2.0 Å being especially preferred. The remaining residues are classified as surface positions if the sum of the distances from their Cα, along their Cα–Cβ vector, to the solvent accessible surface, plus the distance from their Cβ to the closest surface point was less than about 2.5–4 Å, with less than about 2.7 Å being especially preferred. All remaining residues are classified as boundary positions.

Once each variable position is classified as either core, surface or boundary, a set of amino acid side chains, and thus a set of rotamers, is assigned to each position. That is, the set of possible amino acid side chains that the program will allow to be considered at any particular position is chosen. Subsequently, once the possible amino acid side chains are chosen, the set of rotamers that will be evaluated at a particular position can be determined. Thus, a core residue will generally be selected from the group of hydrophobic residues consisting of alanine, valine, isoleucine, leucine, phenylalanine, tyrosine, tryptophan, and methionine (in some embodiments, when the a scaling factor of the van der Waals scoring function, described below, is low, methionine is removed from the set), and the rotamer set for each core position potentially includes rotamers for these eight amino acid side chains (all the rotamers if a backbone independent library is used, and subsets if a rotamer dependent backbone is used). Similarly, surface positions are generally selected from the group of hydrophilic residues consisting of alanine, serine, threonine, aspartic acid, asparagine, glutamine, glutamic acid, arginine, lysine and histidine. The rotamer set for each surface position thus includes rotamers for these ten residues. Finally, boundary positions are generally chosen from alanine, serine, threonine, aspartic acid, asparagine, glutamine, glutamic acid, arginine, lysine histidine, valine, isoleucine, leucine, phenylalanine, tyrosine, tryptophan, and methionine. The rotamer set for each boundary position thus potentially includes every rotamer for these seventeen residues (assuming cysteine, glycine and proline are not used, although they can be).

Thus, as will be appreciated by those in the art, there is a computational benefit to classifying the residue positions, as it decreases the number of calculations. It should also be noted that there may be situations where the sets of core, boundary and surface residues are altered from those described above; for example, under some circumstances, one or more amino acids is either added or subtracted from the set of allowed amino acids. For example, some proteins which dimerize or multimerize, or have ligand binding sites, may contain hydrophobic surface residues, etc. In addition, residues that do not allow helix "capping" or the favorable interaction with an α-helix dipole may be subtracted from a set of allowed residues. This modification of amino acid groups is done on a residue by residue basis.

In a preferred embodiment, proline, cysteine and glycine are not included in the list of possible amino acid side chains, and thus the rotamers for these side chains are not used. However, in a preferred embodiment, when the variable residue position has a φ angle (that is, the dihedral angle defined by 1) the carbonyl carbon of the preceding amino acid; 2) the nitrogen atom of the current residue; 3) the α-carbon of the current residue; and 4) the carbonyl carbon of the current residue) greater than 0°, the position is set to glycine to minimize backbone strain.

Once the group of potential rotamers is assigned for each variable residue position, processing proceeds to step 54 of FIG. 2. This processing step entails analyzing interactions of the rotamers with each other and with the protein backbone to generate optimized protein sequences. The ranking module 34 may be used to perform these operations. That is, computer code is written to implement the following functions. Simplistically, as is generally outlined above, the processing initially comprises the use of a number of scoring functions, described below, to calculate energies of interactions of the rotamers, either to the backbone itself or other rotamers.

The scoring functions include a Van der Waals potential scoring function, a hydrogen bond potential scoring function, an atomic solvation scoring function, a secondary structure propensity scoring function and an electrostatic scoring function. As is further described below, at least one scoring function is used to score each position, although the scoring functions may differ depending on the position classification or other considerations, like favorable interaction with an α-helix dipole. As outlined below, the total energy which is used in the calculations is the sum of the energy of each scoring function used at a particular position, as is generally shown in Equation 1:

$$E_{total} = nE_{vdw} + nE_{as} + nE_{h\text{-}bonding} + nE_{ss} + nE_{elec} \quad \text{Equation 1}$$

In Equation 1, the total energy is the sum of the energy of the van der Waals potential ($E_{vdw}$), the energy of atomic solvation ($E_{as}$), the energy of hydrogen bonding ($E_{h\text{-}bonding}$), the energy of secondary structure ($E_{ss}$) and the energy of electrostatic interaction ($E_{elec}$). The term n is either 0 or 1, depending on whether the term is to be considered for the particular residue position, as is more fully outlined below.

In a preferred embodiment, a van der Waals' scoring function is used. As is known in the art, van der Waals' forces are the weak, non-covalent and non-ionic forces between atoms and molecules, that is, the induced dipole and electron repulsion (Pauli principle) forces.

The van der Waals scoring function is based on a van der Waals potential energy. There are a number of van der Waals potential energy calculations, including a Lennard-Jones 12/6 potential with radii and well depth parameters from the Dreiding force field, Mayo et al., *J. Prot. Chem.*, 1990, expressly incorporated herein by reference, or the exponential 6 potential. Equation 2, shown below, is the preferred Lennard-Jones potential:

$$E_{vdw} = D_0 \left\{ \left( \frac{R_0}{R} \right)^{12} - 2 \left( \frac{R_0}{R} \right)^6 \right\} \quad \text{Equation 2}$$

$R_0$ is the geometric mean of the van der Waals radii of the two atoms under consideration, and $D_0$ is the geometric mean of the well depth of the two atoms under consideration. $E_{vdw}$ and R are the energy and interatomic distance between the two atoms under consideration, as is more fully described below.

In a preferred embodiment, the van der Waals forces are scaled using a scaling factor, a, as is generally discussed in Example 4. Equation 3 shows the use of α in the van der Waals Lennard-Jones potential equation:

$$E_{vdw} = D_0 \left\{ \left( \frac{\alpha R_0}{R} \right)^{12} - 2 \left( \frac{\alpha R_0}{R} \right)^6 \right\} \quad \text{Equation 3}$$

The role of the α scaling factor is to change the importance of packing effects in the optimization and design of any particular protein. As discussed in the Examples, different values for a result in different sequences being generated by the present methods. Specifically, a reduced van der Waals steric constraint can compensate for the restrictive effect of a fixed backbone and discrete side-chain rotamers in the simulation and can allow a broader sampling of sequences compatible with a desired fold. In a preferred embodiment, α values ranging from about 0.70 to about 1.10 can be used, with α values from about 0.8 to about 1.05 being preferred, and from about 0.85 to about 1.0 being especially preferred. Specific α values which are preferred are 0.80, 0.85, 0.90, 0.95, 1.00, and 1.05.

Generally speaking, variation of the van der Waals scale factor a results in four regimes of packing specificity: regime 1 where $0.9 \leq \alpha \leq 1.05$ and packing constraints dominate the sequence selection; regime 2 where $0.8 \leq \alpha \leq 0.9$ and the hydrophobic solvation potential begins to compete with packing forces; regime 3 where α <0.8 and hydrophobic solvation dominates the design; and, regime 4 where α>1.05 and van der Waals repulsions appear to be too severe to allow meaningful sequence selection. In particular, different α values may be used for core, surface and boundary positions, with regimes 1 and 2 being preferred for core residues, regime 1 being preferred for surface residues, and regime 1 and 2 being preferred for boundary residues.

In a preferred embodiment, the van der Waals scaling factor is used in the total energy calculations for each variable residue position, including core, surface and boundary positions.

In a preferred embodiment, an atomic solvation potential scoring function is used. As is appreciated by those in the art, solvent interactions of a protein are a significant factor in protein stability, and residue/protein hydrophobicity has been shown to be the major driving force in protein folding. Thus, there is an entropic cost to solvating hydrophobic surfaces, in addition to the potential for misfolding or aggregation. Accordingly, the burial of hydrophobic surfaces within a protein structure is beneficial to both folding and stability. Similarly, there can be a disadvantage for burying hydrophilic residues. The accessible surface area of a protein atom is generally defined as the area of the surface over which a water molecule can be placed while making van der Waals contact with this atom and not penetrating any other protein atom. Thus, in a preferred embodiment, the solvation potential is generally scored by taking the total possible exposed surface area of the moiety or two independent moieties (either a rotamer or the first rotamer and the second rotamer), which is the reference, and subtracting out the "buried" area, i.e. the area which is not solvent exposed due to interactions either with the backbone or with other rotamers. This thus gives the exposed surface area.

Alternatively, a preferred embodiment calculates the scoring function on the basis of the "buried" portion; i.e. the total possible exposed surface area is calculated, and then the calculated surface area after the interaction of the moieties is subtracted, leaving the buried surface area. A particularly preferred method does both of these calculations.

As is more fully described below, both of these methods can be done in a variety of ways. See Eisenberg et al., *Nature* 319:199–203 (1986); Connolly, *Science* 221:709–713 (1983); and Wodak, et al., *Proc. Natl. Acad. Sci. USA* 77(4):1736–1740 (1980), all of which are expressly incorporated herein by reference. As will be appreciated by those in the art, this solvation potential scoring function is conformation dependent, rather than conformation independent.

In a preferred embodiment, the pairwise salvation potential is implemented in two components, "singles" (rotamer/template) and "doubles" (rotamer/rotamer), as is more fully described below. For the rotamer/template buried area, the reference state is defined as the rotamer in question at residue position i with the backbone atoms only of residues i−1, i and i+1, although in some instances just i may be used. Thus, in a preferred embodiment, the solvation potential is not calculated for the interaction of each backbone atom with a particular rotamer, although more may be done as required. The area of the side chain is calculated with the backbone atoms excluding solvent but not counted in the area. The folded state is defined as the area of the rotamer in question at residue i, but now in the context of the entire template structure including non-optimized side chains, i.e. every other foxed position residue. The rotamer/template buried area is the difference between the reference and the folded states. The rotamer/rotamer reference area can be done in two ways; one by using simply the sum of the areas of the isolated rotamers; the second includes the full backbone. The folded state is the area of the two rotamers placed in their relative positions on the protein scaffold but with no template atoms present. In a preferred embodiment, the Richards definition of solvent accessible surface area (Lee and Richards, J. Mol. Biol. 55:379–400, 1971, hereby incorporated by reference) is used, with a probe radius ranging from 0.8 to 1.6 Å, with 1.4 Å being preferred, and Drieding van der Waals radii, scaled from 0.8 to 1.0. Carbon and sulfur, and all attached hydrogens, are considered nonpolar. Nitrogen and oxygen, and all attached hydrogens, are considered polar. Surface areas are calculated with the Connolly algorithm using a dot density of 10 Å-2 (Connolly, (1983) (supra), hereby incorporated by reference).

In a preferred embodiment, there is a correction for a possible overestimation of buried surface area which may exist in the calculation of the energy of interaction between two rotamers (but not the interaction of a rotamer with the backbone). Since, as is generally outlined below, rotamers are only considered in pairs, that is, a first rotamer is only compared to a second rotamer during the "doubles" calculations, this may overestimate the amount of buried surface area in locations where more than two rotamers interact, that is, where rotamers from three or more residue positions come together. Thus, a correction or scaling factor is used as outlined below.

The general energy of solvation is shown in Equation 4:

$$E_{sa}=f(SA) \qquad \text{Equation 4}$$

where $E_{sa}$ is the energy of solvation, f is a constant used to correlate surface area and energy, and SA is the surface area. This equation can be broken down, depending on which parameter is being evaluated. Thus, when the hydrophobic buried surface area is used, Equation 5 is appropriate:

$$E_{sa}=f_1(SA_{buried\ hydrophobic}) \qquad \text{Equation 5}$$

where $f_1$ is a constant which ranges from about 10 to about 50 cal/mol/Å$^2$, with 23 or 26 cal/mol/Å$^2$ being preferred. When a penalty for hydrophilic burial is being considered, the equation is shown in Equation 6:

$$E_{sa}=f_1(SA_{buried\ hydrophobic})+f_2(SA\text{buried hydrophilic}) \qquad \text{Equation 6}$$

where $f_2$ is a constant which ranges from −50 to −250 cal/mol/Å$^2$, with −86 or −100 cal/mol/Å$^2$ being preferred. Similarly, if a penalty for hydrophobic exposure is used, equation 7 or 8 may be used:

$$E_{sa}=f_1(SA_{buried\ hydrophobic})+f_3(SA_{exposed\ hydrophobic}) \qquad \text{Equation 7}$$

$$E_{sa}=f_1(SA_{buried\ hydrophobic})+f_3(SA_{exposed\ hydrophilic})+f_4(SA_{exposed\ hydrophilic}) \qquad \text{Equation 8}$$

In a preferred embodiment, $f_3=-f_1$.

In one embodiment, backbone atoms are not included in the calculation of surface areas, and values of 23 cal/mol/Å$^2$ ($f_1$) and −86 cal/mol/Å$^2$ ($f_2$) are determined.

In a preferred embodiment, this overcounting problem is addressed using a scaling factor that compensates for only the portion of the expression for pairwise area that is subject to over-counting. In this embodiment, values of −26 cal/mol/Å$^2$ ($f_1$) and 100 cal/mol/Å$^2$ ($f_2$) are determined.

Atomic solvation energy is expensive, in terms of computational time and resources. Accordingly, in a preferred embodiment, the solvation energy is calculated for core and/or boundary residues, but not surface residues, with both a calculation for core and boundary residues being preferred, although any combination of the three is possible.

In a preferred embodiment, a hydrogen bond potential scoring function is used. A hydrogen bond potential is used as predicted hydrogen bonds do contribute to designed protein stability (see Stickle et al., J. Mol. Biol. 226:1143 (1992); Huyghues-Despointes et al., Biochem. 34:13267 (1995), both of which are expressly incorporated herein by reference). As outlined previously, explicit hydrogens are generated on the protein backbone structure.

In a preferred embodiment, the hydrogen bond potential consists of a distance-dependent term and an angle-dependent term, as shown in Equation 9:

$$E_{H-Bonding} = D_0\left\{5\left(\frac{R_0}{R}\right)^{12} - 6\left(\frac{R_0}{R}\right)^{10}\right\}F(\theta, \varnothing, \varphi) \quad \text{Equation 9}$$

where $R_0$ (2.8 Å) and $D_0$ (8 kcal/mol) are the hydrogen-bond equilibrium distance and well-depth, respectively, and R is the donor to acceptor distance. This hydrogen bond potential is based on the potential used in DREIDING with more restrictive angle-dependent terms to limit the occurrence of unfavorable hydrogen bond geometries. The angle term varies depending on the hybridization state of the donor and acceptor, as shown in Equations 10, 11, 12 and 13. Equation 10 is used for $sp^3$ donor to $sp^3$ acceptor; Equation 11 is used for $sp^3$ donor to $sp^2$ acceptor, Equation 12 is used for $sp^2$ donor to $sp^3$ acceptor, and Equation 13 is used for $sp^2$ donor to $sp^2$ acceptor:

$F = \cos^2\theta \cos^2(\varnothing - 109.5)$     Equation 10

$F = \cos^2\theta \cos^2\varnothing$     Equation 11

$F = \cos^4\theta$     Equation 12

$F = \cos^2\theta \cos^2(\max[\phi, \varnothing,])$     Equation 13

In Equations 10–13, $\theta$ is the donor-hydrogen-acceptor angle, $\phi$ is the hydrogen-acceptor-base angle (the base is the atom attached to the acceptor, for example the carbonyl carbon is the base for a carbonyl oxygen acceptor), and $\varphi$ is the angle between the normals of the planes defined by the six atoms attached to the $sp^2$ centers (the supplement of $\phi$ is used when $\phi$ is less than 90°). The hydrogen-bond function is only evaluated when 2.6 Å $\leq R \leq$ 3.2 Å, $\theta > 90°$, $\phi - 109.5° < 90°$ for the $sp_3$ donor –$sp^3$ acceptor case, and, $\phi > 90°$ for the $sp^3$ donor –$sp_2$ acceptor case; preferably, no switching functions are used. Template donors and acceptors that are involved in template-template hydrogen bonds are preferably not included in the donor and acceptor lists. For the purpose of exclusion, a template-template hydrogen bond is considered to exist when 2.5 Å $\leq R \leq$ 3.3 Å and $\theta > 135°$.

The hydrogen-bond potential may also be combined or used with a weak coulombic term that includes a distance-dependent dielectric constant of 40R, where R is the interatomic distance. Partial atomic charges are preferably only applied to polar functional groups. A net formal charge of +1 is used for Arg and Lys and a net formal charge of –1 is used for Asp and Glu; see Gasteiger, et al., *Tetrahedron* 36:3219–3288 (1980); Rappe, et al., *J. Phys. Chem.* 95:3358–3363 (1991).

In a preferred embodiment, an explicit penalty is given for buried polar hydrogen atoms which are not hydrogen bonded to another atom. See Eisenberg, et al., (1986) (supra), hereby expressly incorporated by reference. In a preferred embodiment, this penalty for polar hydrogen burial, is from about 0 to about 3 kcal/mol, with from about 1 to about 3 being preferred and 2 kcal/mol being particularly preferred. This penalty is only applied to buried polar hydrogens not involved in hydrogen bonds. A hydrogen bond is considered to exist when $E_{HB}$ ranges from about 1 to about 4 kcal/mol, with $E_{HB}$ of less than –2 kcal/mol being preferred. In addition, in a preferred embodiment, the penalty is not applied to template hydrogens, i.e. unpaired buried hydrogens of the backbone.

In a preferred embodiment, only hydrogen bonds between a first rotamer and the backbone are scored, and rotamer—rotamer hydrogen bonds are not scored. In an alternative embodiment, hydrogen bonds between a first rotamer and the backbone are scored, and rotamer-rotamer hydrogen bonds are scaled by 0.5.

In a preferred embodiment, the hydrogen bonding scoring function is used for all positions, including core, surface and boundary positions. In alternate embodiments, the hydrogen bonding scoring function may be used on only one or two of these.

In a preferred embodiment, a secondary structure propensity scoring function is used. This is based on the specific amino acid side chain, and is conformation independent. That is, each amino acid has a certain propensity to take on a secondary structure, either α-helix or β-sheet, based on its $\phi$ and $\psi$ angles. See Muñoz et al., *Current Op. in Biotech.* 6:382 (1995); Minor, et al., *Nature* 367:660–663 (1994); Padmanabhan, et al., *Nature* 344:268–270 (1990); Muñoz, et al., *Folding & Design* 1(3):167–178 (1996); and Chakrabartty, et al., Protein Sci. 3:843 (1994), all of which are expressly incorporated herein by reference. Thus, for variable residue positions that are in recognizable secondary structure in the backbone, a secondary structure propensity scoring function is preferably used. That is, when a variable residue position is in an α-helical area of the backbone, the α-helical propensity scoring function described below is calculated. Whether or not a position is in a α-helical area of the backbone is determined as will be appreciated by those in the art, generally on the basis of $\phi$ and $\psi$ angles; for α-helix, $\phi$ angles from –2 to –70 and $\psi$ angles from –30 to –100 generally describe an α-helical area of the backbone.

Similarly, when a variable residue position is in a β-sheet backbone conformation, the β-sheet propensity scoring function is used. β-sheet backbone conformation is generally described by $\phi$ angles from –30 to –100 and X angles from +40 to +180. In alternate preferred embodiments, variable residue positions which are within areas of the backbone which are not assignable to either β-sheet or α-helix structure may also be subjected to secondary structure propensity calculations.

In a preferred embodiment, energies associated with secondary propensities are calculated using Equation 14:

$$E = 10^{N_{ss}(\Delta G°_{aa} - \Delta G°_{ala})} - 1 \quad \text{Equation 14}$$

In Equation 14, $E_\alpha$ (or $E\beta$) is the energy of α-helical propensity, $\Delta G°_{aa}$ is the standard free energy of helix propagation of the amino acid, and $\Delta G°_{ala}$ is the standard free energy of helix propagation of alanine used as a standard, or standard free energy of β-sheet formation of the amino acid, both of which are available in the literature (see Chakrabartty, et al., (1994) (supra), and Munoz, et al., *Folding & Design* 1(3):167–178 (1996)), both of which are expressly incorporated herein by reference), and $N_{ss}$ is the propensity scale factor which is set to range from 1 to 4, with 3.0 being preferred. This potential is preferably selected in order to scale the propensity energies to a similar range as the other terms in the scoring function.

In a preferred embodiment, β-sheet propensities are preferably calculated only where the i–1 and i+1 residues are also in β-sheet conformation.

In a preferred embodiment, the secondary structure propensity scoring function is used only in the energy calculations for surface variable residue positions. In alternate embodiments, the secondary structure propensity scoring function is used in the calculations for core and boundary regions as well.

In a preferred embodiment, an electrostatic scoring function is used, as shown below in Equation 15:

$$E_{elec} = \frac{qq'}{\epsilon r^2}$$ Equation 15

In this Equation, q is the charge on atom 1, q' is charge on atom 2, and r is the interaction distance.

In a preferred embodiment, at least one scoring function is used for each variable residue position; in preferred embodiments, two, three or four scoring functions are used for each variable residue position.

Once the scoring functions to be used are identified for each variable position, the preferred first step in the computational analysis comprises the determination of the interaction of each possible rotamer with all or part of the remainder of the protein. That is, the energy of interaction, as measured by one or more of the scoring functions, of each possible rotamer at each variable residue position with either the backbone or other rotamers, is calculated. In a preferred embodiment, the interaction of each rotamer with the entire remainder of the protein, i.e. both the entire template and all other rotamers, is done. However, as outlined above, it is possible to only model a portion of a protein, for example a domain of a larger protein, and thus in some cases, not all of the protein need be considered.

In a preferred embodiment, the first step of the computational processing is done by calculating two sets of interactions for each rotamer at every position (step 70 of FIG. 3): the interaction of the rotamer side chain with the template or backbone (the "singles" energy), and the interaction of the rotamer side chain with all other possible rotamers at every other position (the "doubles" energy), whether that position is varied or floated. It should be understood that the backbone in this case includes both the atoms of the protein structure backbone, as well as the atoms of any fixed residues, wherein the fixed residues are defined as a particular conformation of an amino acid.

Thus, "singles" (rotamer/template) energies are calculated for the interaction of every possible rotamer at every variable residue position with the backbone, using some or all of the scoring functions. Thus, for the hydrogen bonding scoring function, every hydrogen bonding atom of the rotamer and every hydrogen bonding atom of the backbone is evaluated, and the $E_{HB}$ is calculated for each possible rotamer at every variable position. Similarly, for the van der Waals scoring function, every atom of the rotamer is compared to every atom of the template (generally excluding the backbone atoms of its own residue), and the $E_{vdW}$ is calculated for each possible rotamer at every variable residue position. In addition, generally no van der Waals energy is calculated if the atoms are connected by three bonds or less. For the atomic solvation scoring function, the surface of the rotamer is measured against the surface of the template, and the $E_{as}$ for each possible rotamer at every variable residue position is calculated. The secondary structure propensity scoring function is also considered as a singles energy, and thus the total singles energy may contain an $E_{ss}$ term. As will be appreciated by those in the art, many of these energy terms will be close to zero, depending on the physical distance between the rotamer and the template position; that is, the farther apart the two moieties, the lower the energy.

Accordingly, as outlined above, the total singles energy is the sum of the energy of each scoring function used at a particular position, as shown in Equation 1, wherein n is either 1 or zero, depending on whether that particular scoring function was used at the rotamer position:

$$E_{total} = nE_{vdW} + nE_{as} + nE_{h\text{-}bonding} + nE_{ss} + nE_{elec}$$ Equation 1

Once calculated, each singles $E_{total}$ for each possible rotamer is stored in the memory 24 within the computer, such that it may be used in subsequent calculations, as outlined below.

For the calculation of "doubles" energy (rotamer/rotamer), the interaction energy of each possible rotamer is compared with every possible rotamer at all other variable residue positions. Thus, "doubles" energies are calculated for the interaction of every possible rotamer at every variable residue position with every possible rotamer at every other variable residue position, using some or all of the scoring functions. Thus, for the hydrogen bonding scoring function, every hydrogen bonding atom of the first rotamer and every hydrogen bonding atom of every possible second rotamer is evaluated, and the $E_{HB}$ is calculated for each possible rotamer pair for any two variable positions. Similarly, for the van der Waals scoring function, every atom of the first rotamer is compared to every atom of every possible second rotamer, and the $E_{vdW}$ is calculated for each possible rotamer pair at every two variable residue positions. For the atomic solvation scoring function, the surface of the first rotamer is measured against the surface of every possible second rotamer, and the $E_{as}$ for each possible rotamer pair at every two variable residue positions is calculated. The secondary structure propensity scoring function need not be run as a "doubles" energy, as it is considered as a component of the "singles" energy. As will be appreciated by those in the art, many of these double energy terms will be close to zero, depending on the physical distance between the first rotamer and the second rotamer; that is, the farther apart the two moieties, the lower the energy.

Accordingly, as outlined above, the total doubles energy is the sum of the energy of each scoring function used to evaluate every possible pair of rotamers, as shown in Equation 16, wherein n is either 1 or zero, depending on whether that particular scoring function was used at the rotamer position:

$$E_{total} = nE_{vdW} + nE_{as} + nE_{h\text{-}bonding} + E_{elec}$$ Equation 16

An example is illuminating. A first variable position, i, has three (an unrealistically low number) possible rotamers (which may be either from a single amino acid or different amino acids) which are labelled ia, ib, and ic. A second variable position, j, also has three possible rotamers, labelled jd, je, and jf. Thus, nine doubles energies ($E_{total}$) are calculated in all: $E_{total}$(ia, jd), $E_{total}$(ia, je), $E_{total}$(ia, jf), $E_{total}$(ib, jd), $E_{total}$(ib, je), $E_{total}$(ib, jf), $E_{total}$(ic, jd), $E_{total}$(ic, je), and $E_{total}$(ic, jf).

Once calculated, each doubles $E_{total}$ for each possible rotamer pair is stored in memory 24 within the computer, such that it may be used in subsequent calculations, as outlined below.

Once the singles and doubles energies are calculated and stored, the next step of the computational processing may occur. Generally speaking, the goal of the computational processing is to determine a set of optimized protein sequences. By "optimized protein sequence" herein is meant a sequence that best fits the mathematical equations herein. As will be appreciated by those in the art, a global optimized sequence is the one sequence that best fits Equation 1, i.e. the sequence that has the lowest energy of any possible sequence. However, there are any number of sequences that are not the global minimum but that have low energies.

In a preferred embodiment, the set comprises the globally optimal sequence in its optimal conformation, i.e. the optimum rotamer at each variable position. That is, computational processing is run until the simulation program converges on a single sequence which is the global optimum.

In a preferred embodiment, the set comprises at least two optimized protein sequences. Thus for example, the computational proces sing step may eliminate a number of disfavored combinations but be stopped prior to convergence, providing a set of sequences of which the global optimum is one. In addition, further computational analysis, for example using a different method, may be run on the set, to further eliminate sequences or rank them differently. Alternatively, as is more fully described below, the global optimum may be reached, and then further computational processing may occur, which generates additional optimized sequences in the neighborhood of the global optimum.

If a set comprising more than one optimized protein sequences is generated, they may be rank ordered in terms of theoretical quantitative stability, as is more fully described below.

In a preferred embodiment, the computational processing step first comprises an elimination step, sometimes referred to as "applying a cutoff", either a singles elimination or a doubles elimination. Singles elimination comprises the elimination of all rotamers with template interaction energies of greater than about 10 kcal/mol prior to any computation, with elimination energies of greater than about 15 kcal/mol being preferred and greater than about 25 kcal/mol being especially preferred. Similarly, doubles elimination is done when a rotamer has interaction energies greater than about 10 kcal/mol with all rotamers at a second residue position, with energies greater than about 15 being preferred and greater than about 25 kcal/mol being especially preferred.

In a preferred embodiment, the computational processing comprises direct determination of total sequence energies, followed by comparison of the total sequence energies to ascertain the global optimum and rank order the other possible sequences, if desired. The energy of a total sequence is shown below in Equation 17:

$$E_{total\ protein} = E_{(b-b)} + \sum_{all\ i} E_{(ia)} + \sum_{all\ i} + \sum_{all\ j\ pairs} E_{(ia,ja)} \quad \text{Equation 17}$$

Thus every possible combination of rotamers may be directly evaluated by adding the backbone-backbone (sometimes referred to herein as template-template) energy ($E_{(b-b)}$ which is constant over all sequences herein since the backbone is kept constant), the singles energy for each rotamer (which has already been calculated and stored), and the doubles energy for each rotamer pair (which has already been calculated and stored). Each total sequence energy of each possible rotamer sequence can then be ranked, either from best to worst or worst to best. This is obviously computationally expensive and becomes unwieldy as the length of the protein increases.

In a preferred embodiment, the computational processing includes one or more Dead-End Elimination (DEE) computational steps. The DEE theorem is the basis for a very fast discrete search program that was designed to pack protein side chains on a fixed backbone with a known sequence. See Desmet, et al., Nature 356:539–542 (1992); Desmet, et al., The Protein Folding Problem and Tertiary Structure Prediction, Ch. 10:1–49 (1994); Goldstein, Biophys. Jour. 66:1335–1340 (1994), all of which are incorporated herein by reference. DEE is based on the observation that if a rotamer can be eliminated from consideration at a particular position, i.e. make a determination that a particular rotamer is definitely not part of the global optimal conformation, the size of the search is reduced. This is done by comparing the worst interaction (i.e. energy or $E_{total}$) of a first rotamer at a single variable position with the best interaction of a second rotamer at the same variable position. If the worst interaction of the first rotamer is still better than the best interaction of the second rotamer, then the second rotamer cannot possibly be in the optimal conformation of the sequence. The original DEE theorem is shown in Equation 18:

$$E(ia) + \sum_j [\text{min over } t\{E(ia, jt)\}] > \quad \text{Equation 18}$$

$$E(ib) + \sum_j [\text{max over } t\{E(ib, jt)\}]$$

In Equation 18, rotamer ia is being compared to rotamer ib. The left side of the inequality is the best possible interaction energy ($E_{total}$) of ia with the rest of the protein; that is, "min over t" means find the rotamer t on position j that has the best interaction with rotamer ia. Similarly, the right side of the inequality is the worst possible (max) interaction energy of rotamer ib with the rest of the protein. If this inequality is true, then rotamer ia is Dead-Ending and can be Eliminated. The speed of DEE comes from the fact that the theorem only requires sums over the sequence length to test and eliminate rotamers.

In a preferred embodiment, a variation of DEE is performed. Goldstein DEE, based on Goldstein, (1994) (supra), hereby expressly incorporated by reference, is a variation of the DEE computation, as shown in Equation 19:

$$E(ia) - E(ib) + \sum [\text{min over } t\{E(ia, jt) - E(ib, jt)\}] > 0 \quad \text{Equation 19}$$

In essence, the Goldstein Equation 19 says that a first rotamer a of a particular position i (rotamer ia) will not contribute to a local energy minimum if the energy of conformation with ia can always be lowered by just changing the rotamer at that position to ib, keeping the other residues equal. If this inequality is true, then rotamer ia is Dead-Ending and can be Eliminated.

Thus, in a preferred embodiment, a first DEE computation is done where rotamers at a single variable position are compared, ("singles" DEE) to eliminate rotamers at a single position. This analysis is repeated for every variable position, to eliminate as many single rotamers as possible. In addition, every time a rotamer is eliminated from consideration through DEE, the minimum and maximum calculations of Equation 18 or 19 change, depending on which DEE variation is used, thus conceivably allowing the elimination of further rotamers. Accordingly, the singles DEE computation can be repeated until no more rotamers can be eliminated; that is, when the inequality is not longer true such that all of them could conceivably be found on the global optimum.

In a preferred embodiment, "doubles" DEE is additionally done. In doubles DEE, pairs of rotamers are evaluated; that is, a first rotamer at a first position and a second rotamer at a second position are compared to a third rotamer at the first position and a fourth rotamer at the second position, either using original or Goldstein DEE. Pairs are then flagged as nonallowable, although single rotamers cannot be eliminated, only the pair. Again, as for singles DEE, every time a rotamer pair is flagged as nonallowable, the minimum calculations of Equation 18 or 19 change (depending on which DEE variation is used) thus conceivably allowing the flagging of further rotamer pairs. Accordingly, the doubles DEE computation can be repeated until no more rotamer pairs can be flagged; that is, where the energy of rotamer pairs overlap such that all of them could conceivably be found on the global optimum.

In addition, in a preferred embodiment, rotamer pairs are initially prescreened to eliminate rotamer pairs prior to DEE. This is done by doing relatively computationally inexpensive calculations to eliminate certain pairs up front. This may be done in several ways, as is outlined below.

In a preferred embodiment, the rotamer pair with the lowest interaction energy with the rest of the system is found. Inspection of the energy distributions in sample matrices has revealed that an $i_u j_v$ pair that dead-end eliminates a particular $i_r j_s$ pair can also eliminate other $i_r j_s$ pairs. In fact, there are often a few $i_u j_v$ pairs, which we call "magic bullets," that eliminate a significant number of $i_r j_s$ pairs. We have found that one of the most potent magic bullets is the pair for which maximum interaction energy, $t_{max}([i_u j_v])k_t$, is least. This pair is referred to as $[i_u j_v]_{mb}$. If this rotamer pair is used in the first round of doubles DEE, it tends to eliminate pairs faster.

Our first speed enhancement is to evaluate the first-order doubles calculation for only the matrix elements in the row corresponding to the $[i_u j_v]_{mb}$ pair. The discovery of $[i_u j_v]_{mb}$ is an $n^2$ calculation (n=the number of rotamers per position), and the application of Equation 19 to the single row of the matrix corresponding to this rotamer pair is another $n^2$ calculation, so the calculation time is small in comparison to a full first-order doubles calculation. In practice, this calculation produces a large number of dead-ending pairs, often enough to proceed to the next iteration of singles elimination without any further searching of the doubles matrix.

The magic bullet first-order calculation will also discover all dead-ending pairs that would be discovered by the Equation 18 or 19, thereby making it unnecessary. This stems from the fact that $\in_{max}([i_u j_v]_{mb})$ must be less than or equal to any $\in_{max}([i_u j_v])$ that would successfully eliminate a pair by he Equation 18 or 19.

Since the minima and maxima of any given pair has been precalculated as outlined herein, a second speed-enhancement precalculation may be done. By comparing extrema, pairs that will not dead end can be identified and thus skipped, reducing the time of the DEE calculation. Thus, pairs that satisfy either one of the following criteria are skipped:

$$\in_{min}([i_r j_s]) < \in_{min}([i_u j_v]) \quad \text{Equation 20}$$

$$\in_{max}([i_r j_s]) < \in_{min}([i_u j_v]) \quad \text{Equation 21}$$

Because the matrix containing these calculations is symmetrical, half of its elements will satisfy the first inequality Equation 20, and half of those remaining will satisfy the other inequality Equation 21. These three quarters of the matrix need not be subjected to the evaluation of Equation 18 or 19, resulting in a theoretical speed enhancement of a factor of four.

The last DEE speed enhancement refines the search of the remaining quarter of the matrix. This is done by constructing a metric from the precomputed extrema to detect those matrix elements likely to result in a dead-ending pair.

A metric was found through analysis of matrices from different sample optimizations. We searched for combinations of the extrema that predicted the likelihood that a matrix element would produce a dead-ending pair. Interval sizes (see FIG. 12) for each pair were computed from differences of the extrema. The size of the overlap of the $i_r j_s$ and $i_u j_v$ intervals were also computed, as well as the difference between the minima and the difference between the maxima. Combinations of these quantities, as well as the lone extrema, were tested for their ability to predict the occurrence of dead-ending pairs. Because some of the maxima were very large, the quantities were also compared logarithmically.

Most of the combinations were able to predict dead-ending matrix elements to varying degrees. The best metrics were the fractional interval overlap with respect to each pair, referred to herein as $q_{rs}$ and $q_{uv}$.

$$q_{rs} = \frac{\text{interval overlap}}{\text{interval }([i_r j_s])} = \frac{\in_{max}([i_u j_v]) - \in_{min}([i_r j_s])}{\in_{max}([i_r j_s]) - \in_{min}([i_r j_s])} \quad \text{Equation 22}$$

$$q_{uv} = \frac{\text{interval overlap}}{\text{interval }([i_u j_v])} = \frac{\in_{max}([i_u j_v]) - \in_{min}([i_r j_s])}{\in_{max}([i_u j_v]) - \in_{min}([i_u j_v])} \quad \text{Equation 23}$$

These values are calculated using the minima and maxima equations 24, 25, 26 and 27 (see FIG. 14):

$$\in_{max}([i_r j_s]) = \in([i_r j_s]) + \sum_{k \neq i \neq j} \max_t \in([i_r j_s], k) \quad \text{Equation 24}$$

$$\in_{min}([i_r j_s]) = \in([i_r j_s]) + \sum_{k \neq i \neq j} \min_t \in([i_r j_s], k_1) \quad \text{Equation 25}$$

$$\in_{max}([i_u j_v]) = \in([i_u j_v]) + \sum_{k \neq i \neq j} \max_t \in([i_u j_v], k_t) \quad \text{Equation 26}$$

$$\in_{min}([i_u j_v]) = \in([i_u j_v]) + \sum_{k \neq i \neq j} \min_t \in([i_u j_v], k_1) \quad \text{Equation 27}$$

These metrics were selected because they yield ratios of the occurrence of dead-ending matrix elements to the total occurrence of elements that are higher than any of the other metrics tested.

For example, there are very few matrix elements (~2%) for which $q_{rs} > 0.98$, yet these elements produce 30–40% of all of the dead-ending pairs.

Accordingly, the first-order doubles criterion is applied only to those doubles for which $q_{rs} > 0.98$ and $q_{uv} > 0.99$. The sample data analyses predict that by using these two metrics, as many as half of the dead-ending elements may be found by evaluating only two to five percent of the reduced matrix.

Generally, as is more fully described below, single and double DEE, using either or both of original DEE and Goldstein DEE, is run until no further elimination is possible. Usually, convergence is not complete, and further elimination must occur to achieve convergence. This is generally done using "super residue" DEE.

In a preferred embodiment, additional DEE computation is done by the creation of "super residues" or "unification", as is generally described in Desmet, *Nature* 356:539–542 (1992); Desmet, et al., *The Protein Folding Problem and Tertiary Structure Prediction*, Ch. 10:1–49 (1994); Goldstein, et al., supra. A super residue is a combination of two or more variable residue positions which is then treated as a single residue position. The super residue is then evaluated in singles DEE, and doubles DEE, with either other residue positions or super residues. The disadvantage of super residues is that there are many more rotameric states which must be evaluated; that is, if a first variable residue position has 5 possible rotamers, and a second variable residue position has 4 possible rotamers, there are 20 possible super residue rotamers which must be evaluated. However, these super residues may be eliminated similar to singles, rather than being flagged like pairs.

The selection of which positions to combine into super residues may be done in a variety of ways. In general, random selection of positions for super residues results in inefficient elimination, but it can be done, although this is not preferred. In a preferred embodiment, the first evaluation is the selection of positions for a super residue is the number of rotamers at the position. If the position has too many rotamers, it is never unified into a super residue, as the computation becomes too unwieldy. Thus, only positions with fewer than about 100,000 rotamers are chosen, with less than about 50,000 being preferred and less than about 10,000 being especially preferred.

In a preferred embodiment, the evaluation of whether to form a super residue is done as follows. All possible rotamer pairs are ranked using Equation 28, and the rotamer pair with the highest number is chosen for unification:

$$\frac{\text{fraction of flagged pairs}}{\log^{(\text{number of super rotamers from the potential unification})}} \qquad \text{Equation 28}$$

Equation 28 is looking for the pair of positions that has the highest fraction or percentage of flagged pairs but the fewest number of super rotamers. That is, the pair that gives the highest value for Equation 28 is preferably chosen. Thus, if the pair of positions that has the highest number of flagged pairs but also a very large number of super rotamers (that is, the number of rotamers at position i times the number of rotamers at position j), this pair may not be chosen (although it could) over a lower percentage of flagged pairs but fewer super rotamers.

In an alternate preferred embodiment, positions are chosen for super residues that have the highest average energy; that is, for positions i and j, the average energy of all rotamers for i and all rotamers for j is calculated, and the pair with the highest average energy is chosen as a super residue.

Super residues are made one at a time, preferably. After a super residue is chosen, the singles and doubles DEE computations are repeated where the super residue is treated as if it were a regular residue. As for singles and doubles DEE, the elimination of rotamers in the super residue DEE will alter the minimum energy calculations of DEE. Thus, repeating singles and/or doubles DEE can result in further elimination of rotamers.

FIG. 3 is a detailed illustration of the processing operations associated with a ranking module 34 of the invention. The calculation and storage of the singles and doubles energies 70 is the first step, although these may be recalculated every time. Step 72 is the optional application of a cutoff, where singles or doubles energies that are too high are eliminated prior to further processing. Either or both of original singles DEE 74 or Goldstein singles DEE 76 may be done, with the elimination of original singles DEE 74 being generally preferred. Once the singles DEE is run, original doubles (78) and/or Goldstein doubles (80) DEE is run. Super residue DEE is then generally run, either original (82) or Goldstein (84) super residue DEE. This preferably results in convergence at a global optimum sequence. As is depicted in FIG. 3, after any step any or all of the previous steps can be rerun, in any order.

The addition of super residue DEE to the computational processing, with repetition of the previous DEE steps, generally results in convergence at the global optimum. Convergence to the global optimum is guaranteed if no cutoff applications are made, although generally a global optimum is achieved even with these steps. In a preferred embodiment, DEE is run until the global optimum sequence is found. That is, the set of optimized protein sequences contains a single member, the global optimum.

In a preferred embodiment, the various DEE steps are run until a managable number of sequences is found, i.e. no further processing is required. These sequences represent a set of optimized protein sequences, and they can be evaluated as is more fully described below. Generally, for computational purposes, a manageable number of sequences depends on the length of the sequence, but generally ranges from about 1 to about $10^{15}$ possible rotamer sequences.

Alternatively, DEE is run to a point, resulting in a set of optimized sequences (in this context, a set of remainder sequences) and then further compututational processing of a different type may be run. For example, in one embodiment, direct calculation of sequence energy as outlined above is done on the remainder possible sequences. Alternatively, a Monte Carlo search can be run.

In a preferred embodiment, the computation processing need not comprise a DEE computational step. In this embodiment, a Monte Carlo search is undertaken, as is known in the art. See Metropolis et al., J. Chem. Phys. 21:1087 (1953), hereby incorporated by reference. In this embodiment, a random sequence comprising random rotamers is chosen as a start point. In one embodiment, the variable residue positions are classified as core, boundary or surface residues and the set of available residues at each position is thus defined. Then a random sequence is generated, and a random rotamer for each amino acid is chosen. This serves as the starting sequence of the Monte Carlo search. A Monte Carlo search then makes a random jump at one position, either to a different rotamer of the same amino acid or a rotamer of a different amino acid, and then a new sequence energy ($E_{total\ sequence}$) is calculated, and if the new sequence energy meets the Boltzmann criteria for acceptance, it is used as the starting point for another jump. If the Boltzmann test fails, another random jump is attempted from the previous sequence. In this way, sequences with lower and lower energies are found, to generate a set of low energy sequences.

If computational processing results in a single global optimum sequence, it is frequently preferred to generate additional sequences in the energy neighborhood of the global solution, which may be ranked. These additional sequences are also optimized protein sequences. The generation of additional optimized sequences is generally preferred so as to evaluate the differences between the theoretical and actual energies of a sequence. Generally, in a preferred embodiment, the set of sequences is at least about 75% homologous to each other, with at least about 80% homologous being preferred, at least about 85% homologous being particularly preferred, and at least about 90% being especially preferred. In some cases, homology as high as 95% to 98% is desirable. Homology in this context means sequence similarity or identity, with identity being preferred. Identical in this context means identical amino acids at corresponding positions in the two sequences which are being compared. Homology in this context includes amino acids which are identical and those which are similar (functionally equivalent). This homology will be determined using standard techniques known in the art, such as the Best Fit sequence program described by Devereux, et al., *Nucl. Acid Res.*, 12:387–395 (1984), or the BLASTX program (Altschul, et al., *J. Mol. Biol.*, 215:403–410 (1990)) preferably using the default settings for either.

The alignment may include the introduction of gaps in the sequences to be aligned. In addition, for sequences which contain either more or fewer amino acids than an optimum sequence, it is understood that the percentage of homology will be determined based on the number of homologous amino acids in relation to the total number of amino acids. Thus, for example, homology of sequences shorter than an optimum will be determined using the number of amino acids in the shorter sequence.

Once optimized protein sequences are identified, the processing of FIG. 2 optionally proceeds to step 56 which entails searching the protein sequences. This processing may be implemented with the search module 36. The search module 36 is a set of computer code that executes a search strategy. For example, the search module 36 may be written to execute a Monte Carlo search as described above. Starting with the global solution, random positions are changed to other rotamers allowed at the particular position, both rotamers from the same amino acid and rotamers from different amino acids. A new sequence energy ($E_{total\ sequence}$) is calculated, and if the new sequence energy meets the Boltzmann criteria for acceptance, it is used as the starting point for another jump. See Metropolis et al., 1953, supra, hereby incorporated by reference. If the Boltzmann test fails, another random jump is attempted from the previous sequence. A list of the sequences and their energies is maintained during the search. After a predetermined number of jumps, the best scoring sequences may be output as a rank-ordered list. Preferably, at least about $10^6$ jumps are made, with at least about $10^7$ jumps being preferred and at least about $10^8$ jumps being particularly preferred. Preferably, at least about 100 to 1000 sequences are saved, with at least about 10,000 sequences being preferred and at least about 100,000 to 1,000,000 sequences being especially preferred. During the search, the temperature is preferably set to 1000 K.

Once the Monte Carlo search is over, all of the saved sequences are quenched by changing the temperature to 0 K, and fixing the amino acid identity at each position. Preferably, every possible rotamer jump for that particular amino acid at every position is then tried.

The computational processing results in a set of optimized protein sequences. These optimized protein sequences are generally, but not always, significantly different from the wild-type sequence from which the backbone was taken. That is, each optimized protein sequence preferably comprises at least about 5–10% variant amino acids from the starting or wild-type sequence, with at least about 15–20% changes being preferred and at least about 30% changes being particularly preferred.

These sequences can be used in a number of ways. In a preferred embodiment, one, some or all of the optimized protein sequences are constructed into designed proteins, as show with step 58 of FIG. 2. Thereafter, the protein sequences can be tested, as shown with step 60 of the FIG. 2. Generally, this can be done in one of two ways.

In a preferred embodiment, the designed proteins are chemically synthesized as is known in the art. This is particularly useful when the designed proteins are short, preferably less than 150 amino acids in length, with less than 100 amino acids being preferred, and less than 50 amino acids being particularly preferred, although as is known in the art, longer proteins can be made chemically or enzymatically.

In a preferred embodiment, particularly for longer proteins or proteins for which large samples are desired, the optimized sequence is used to create a nucleic acid such as DNA which encodes the optimized sequence and which can then be cloned into a host cell and expressed. Thus, nucleic acids, and particularly DNA, can be made which encodes each optimized protein sequence. This is done using well known procedures. The choice of codons, suitable expression vectors and suitable host cells will vary depending on a number of factors, and can be easily optimized as needed.

Once made, the designed proteins are experimentally evaluated and tested for structure, function and stability, as required. This will be done as is known in the art, and will depend in part on the original protein from which the protein backbone structure was taken. Preferably, the designed proteins are more stable than the known protein that was used as the starting point, although in some cases, if some constraints are placed on the methods, the designed protein may be less stable. Thus, for example, it is possible to fix certain residues for altered biological activity and find the most stable sequence, but it may still be less stable than the wild type protein. Stable in this context means that the new protein retains either biological activity or conformation past the point at which the parent molecule did. Stability includes, but is not limited to, thermal stability, i.e. an increase in the temperature at which reversible or irreversible denaturing starts to occur; proteolytic stability, i.e. a decrease in the amount of protein which is irreversibly cleaved in the presence of a particular protease (including autolysis); stability to alterations in pH or oxidative conditions; chelator stability; stability to met al ions; stability to solvents such as organic solvents, surfactants, formulation chemicals; etc.

In a preferred embodiment, the modelled proteins are at least about 5% more stable than the original protein, with at least about 10% being preferred and at least about 20–50% being especially preferred.

The results of the testing operations may be computationally assessed, as shown with step 62 of FIG. 2. An assessment module 38 may be used in this operation. That is, computer code may be prepared to analyze the test data with respect to any number of metrices.

At this processing juncture, if the protein is selected (the yes branch at block 64) then the protein is utilized (step 66), as discussed below. If a protein is not selected, the accumulated information may be used to alter the ranking module 34, and/or step 56 is repeated and more sequences are searched.

In a preferred embodiment, the experimental results are used for design feedback and design optimization.

Once made, the proteins of the invention find use in a wide variety of applications, as will be appreciated by those in the art, ranging from industrial to pharmacological uses, depending on the protein. Thus, for example, proteins and enzymes exhibiting increased thermal stability may be used in industrial processes that are frequently run at elevated temperatures, for example carbohydrate processing (including saccharification and liquifaction of starch to produce high fructose corn syrup and other sweetners), protein processing (for example the use of proteases in laundry detergents, food processing, feed stock processing, baking, etc.), etc. Similarly, the methods of the present invention allow the generation of useful pharmaceutical proteins, such as analogs of known proteinaceous drugs which are more thermostable, less proteolytically sensitive, or contain other desirable changes.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are explicitly incorporated by reference.

EXAMPLES

Example 1

Protein Design Using van der Waals and Atomic Solvation Scoring Functions with DEE A cyclical design strategy was developed that couples theory, computation and experimental testing in order to address the problems of specificity and learning (FIG. 4). Our protein design automation (PDA) cycle is comprised of four components: a design paradigm, a simulation module, experimental testing and data analysis. The design paradigm is based on the concept of inverse folding (Pabo, *Nature* 301:200 (1983); Bowie, et al., *Science* 253:164–170 (1991)) and consists of the use of a fixed backbone onto which a sequence of side-chain rotamers can be placed, where rotamers are the allowed conformations of amino acid side chains (Ponder, et al., (1987) (supra)). Specific tertiary interactions based on the three dimensional juxtaposition of atoms are used to determine the sequences that will potentially best adopt the target fold. Given a backbone geometry and the possible rotamers allowed for each residue position as input, the simulation must generate as output a rank ordered list of solutions based on a cost function that explicitly considers the atom positions in the various rotamers. The principle obstacle is that a fixed backbone comprised of n residues and m possible rotamers per residue (all rotamers of all allowed amino acids) results in $m^n$ possible arrangements of the system, an immense number for even small design problems. For example, to consider 50 rotamers at 15 positions results in over $10^{25}$ sequences, which at an evaluation rate of $10^9$ sequences per second (far beyond current capabilities) would take $10^9$ years to exhaustively search for the global minimum. The synthesis and characterization of a subset of amino acid sequences presented by the simulation module generates experimental data for the analysis module. The analysis section discovers correlations between calculable properties of the simulated structures and the experimental observables. The goal of the analysis is to suggest quantitative modifications to the simulation and in some cases to the guiding design paradigm. In other words, the cost function used in the simulation module describes a theoretical potential energy surface whose horizontal axis comprises all possible solutions to the problem at hand. This potential energy surface is not guaranteed to match the actual potential energy surface which is determined from the experimental data. In this light, the goal of the analysis becomes the correction of the simulation cost function in order to create better agreement between the theoretical and actual potential energy surfaces. If such corrections can be found, then the output of subsequent simulations will be amino acid sequences that better achieve the target properties. This design cycle is generally applicable to any protein system and, by removing the subjective human component, allows a largely unbiased approach to protein design, i.e. protein design automation.

The PDA side-chain selection algorithm requires as input a backbone structure defining the desired fold. The task of designing a sequence that takes this fold can be viewed as finding an optimal arrangement of amino acid side chains relative to the given backbone. It is not sufficient to consider only the identity of an amino acid when evaluating sequences. In order to correctly account for the geometric specificity of side-chain placement, all possible conformations of each side chain must also be examined. Statistical surveys of the protein structure database (Ponder, et al., supra) have defined a discrete set of allowed conformations, called rotamers, for each amino acid side chain. We use a rotamer library based on the Ponder and Richards library to define allowed conformations for the side chains in PDA.

Using a rotamer description of side chains, an optimal sequence for a backbone can be found by screening all possible sequences of rotamers, where each backbone position can be occupied by each amino acid in all its possible rotameric states. The discrete nature of rotamer sets allows a simple calculation of the number of rotamer sequences to be tested. A backbone of length n with m possible rotamers per position will have $m^n$ possible rotamer sequences. The size of the search space grows exponentially with sequence length which for typical values of n and m render intractable an exhaustive search. This combinatorial "explosion" is the primary obstacle to be overcome in the simulation phase of PDA.

Simulation Algorithm:

An extension of the Dead End Elimination (DEE) theorem was developed (Desmet, et al., (1992( (supra); Desmet, et al., (1994) (supra); Goldstein, (1994) (supra) to solve the combinatorial search problem. The DEE theorem is the basis for a very fast discrete search algorithm that was designed to pack protein side chains on a fixed backbone with a known sequence. Side chains are described by rotamers and an atomistic forcefield is used to score rotamer arrangements. The DEE theorem guarantees that if the algorithm converges, the global optimum packing is found. The DEE method is readily extended to our inverse folding design paradigm by releasing the constraint that a position is limited to the rotamers of a single amino acid. This extension of DEE greatly increases the number of rotamers at each position and requires a significantly modified implementation to ensure convergence, described more fully herein. The guarantee that only the global optimum will be found is still valid, and in our extension means that the globally optimal sequence is found in its optimal conformation.

DEE was implemented with a novel addition to the improvements suggested by Goldstein (Goldstein, (1994) (supra)). As has been noted, exhaustive application of the R=1 rotamer elimination and R=0 rotamer-pair flagging equations and limited application of the R=1 rotamer-pair flagging equation routinely fails to find the global solution. This problem can be overcome by unifying residues into "super residues" (Desmet, et al., (1 992( (supra); Desmet, et al., (1994) (supra); Goldstein, (1994) (supra). However, unification can cause an unmanageable increase in the number of super rotamers per super residue position and can lead to intractably slow performance since the computation time for applying the R=1 rotamer-pair flagging equation increases as the fourth power of the number of rotamers. These problems are of particular importance for protein design applications given the requirement for large numbers of rotamers per residue position. In order to limit memory size and to increase performance, we developed a heuristic that governs which residues (or super residues) get unified and the number of rotamer (or super rotamer) pairs that are included in the R=1 rotamer-pair flagging equation. A program called PDA_DEE was written that takes a list of rotamer energies from PDA_SETUP and outputs the global minimum sequence in its optimal conformation with its energy.

Scoring Functions:

The rotamer library used was similar to that used by Desmet and coworkers (Desmet, et al., (1992) (supra)). $X_1$ and $X_2$ angle values of rotamers for all amino acids except Met, Arg and Lys were expanded plus and minus one standard deviation about the mean value from the Ponder and Richards library (supra) in order to minimize possible errors that might arise from the discreteness of the library. $c_3$ and $c_4$ angles that were undetermined from the database statistics were assigned values of 0° and 180° for Gln and 60°, −60° and 180° for Met, Lys and Arg. The number of rotamers per amino acid is: Gly, 1; Ala, 1; Val, 9; Ser, 9; Cys, 9; Thr, 9; Leu, 36; Ile, 45; Phe, 36; Tyr, 36; Trp, 54; His, 54; Asp, 27; Asn, 54; Glu, 69; Gln, 90; Met, 21; Lys, 57; Arg, 55. The cyclic amino acid Pro was not included in the library. Further, all rotamers in the library contained explicit hydrogen atoms. Rotamers were built with bond lengths and angles from the Dreiding forcefield (Mayo, et al., J. Phys. Chem. 94:8897 (1990)).

The initial scoring function for sequence arrangements used in the search was an atomic van der Waals potential. The van der Waals potential reflects excluded volume and steric packing interactions which are important determinants of the specific three dimensional arrangement of protein side chains. A Lennard-Jones 12-6 potential with radii and well depth parameters from the Dreiding forcefield was used for van der Waals interactions. Non-bonded interactions for atoms connected by one or two bonds were not considered. van der Waals radii for atoms connected by three bonds were scaled by 0.5. Rotamer/rotamer pair energies and rotamer/template energies were calculated in a manner consistent with the published DEE algorithm (Desmet, et al., (1992) (supra)). The template consisted of the protein backbone and the side chains of residue positions not to be optimized. No intra-side-chain potentials were calculated. This scheme scored the packing geometry and eliminated bias from rotamer internal energies. Prior to DEE, all rotamers with template interaction energies greater than 25 kcal/mol were eliminated. Also, any rotamer whose interaction was greater than 25 kcal/mol with all other rotamers at another residue position was eliminated. A program called PDA_SETUP was written that takes as input backbone coordinates, including side chains for positions not optimized, a rotamer library, a list of positions to be optimized and a list of the amino acids to be considered at each position. PDA_SETUP outputs a list of rotamer/template and rotamer/rotamer energies.

The pairwise solvation potential was implemented in two components to remain consistent with the DEE methodology: rotamer/template and rotamer/rotamer burial. For the rotamer/template buried area, the reference state was defined as the rotamer in question at residue i with the backbone atoms only of residues i−1, i and i+1. The area of the side chain was calculated with the backbone atoms excluding solvent but not counted in the area. The folded state was defined as the area of the rotamer in question at residue i, but now in the context of the entire template structure including non-optimized side chains. The rotamer/template buried area is the difference between the reference and the folded states. The rotamer/rotamer reference area is simply the sum of the areas of the isolated rotamers. The folded state is the area of the two rotamers placed in their relative positions on the protein scaffold but with no template atoms present. The Richards definition of solvent accessible surface area (Lee & Richards, 1971, supra) was used, with a probe radius of 1.4 Å and Drieding van der Waals radii. Carbon and sulfur, and all attached hydrogens, were considered nonpolar. Nitrogen and oxygen, and all attached hydrogens, were considered polar. Surface areas were calculated with the Connolly algorithm using a dot density of 10 $Å^{-2}$ (Connolly, (1983) (supra)). In more recent implementations of PDA_SETUP, the MSEED algorithm of Scheraga has been used in conjunction with the Connolly algorithm to speed up the calculation (Perrot, et al., J. Comput. Chem. 13:1–11 (1992).

Monte Carlo Search:

Following DEE optimization, a rank ordered list of sequences was generated by a Monte Carlo search in the neighborhood of the DEE solution. This list of sequences was necessary because of possible differences between the theoretical and actual potential surfaces. The Monte Carlo search starts at the global minimum sequence found by DEE. A residue was picked randomly and changed to a random rotamer selected from those allowed at that site. A new sequence energy was calculated and, if it met the Boltzman criteria for acceptance, the new sequence was used as the starting point for another jump. If the Boltzman test failed, then another random jump was attempted from the previous sequence. A list of the best sequences found and their energies was maintained throughout the search. Typically $10^6$ jumps were made, 100 sequences saved and the temperature was set to 1000 K. After the search was over, all of the saved sequences were quenched by changing the temperature to 0 K, fixing the amino acid identity and trying every possible rotamer jump at every position. The search was implemented in a program called PDA_MONTE whose input was a global optimum solution from PDA_DEE and a list of rotamer energies from PDA_SETUP. The output was a list of the best sequences rank ordered by their score. PDA_SETUP, PDA_DEE and PDA_MONTE were implemented in the CERIUS2 software development environment (Biosym/Molecular Simulations, San Diego, Calif.).

PDA_SETUP, PDA_DEE, and PDA_MONTE were implemented in the CERIUS2 software development environment (Biosym/Molecular Simulations, San Diego, Calif.).

Model System and Experimental Testing:

The homodimeric coiled coil of α helices was selected as the initial design target. Coiled coils are readily synthesized by solid phase techniques and their helical secondary structure and dimeric tertiary organization ease characterization. Their sequences display a seven residue periodic HP pattern called a heptad repeat, (a·b·c·d·e·f·g) (Cohen & Parry, Proteins Struc. Func. Genet. 7:1–15 (1990)). The a and d positions are usually hydrophobic and buried at the dimer interface while the other positions are usually polar and solvent exposed (FIG. 5). The backbone needed for input to the simulation module was taken from the crystal structure of GCN4-p1 (O'Shea, et al., Science 254:539 (1991)). The 16 hydrophobic a and d positions were optimized in the crystallographically determined fixed field of the rest of the protein. Homodimer sequence symmetry was enforced, only rotamers from hydrophobic amino acids (A, V, L, I, M, F, Y and W) were considered and the asparagine at an a position, Asn 16, was not optimized.

Homodimeric coiled coils were modeled on the backbone coordinates of GCN4-p1, PDB ascension code 2ZTA (Bernstein, et al., J. Mol. Biol. 112:535 (1977); O'Shea, et al., supra). Atoms of all side chains not optimized were left in their crystallographically determined positions. The program BIOGRAF (Biosym/Molecular Simulations, San Diego, Calif.) was used to generate explicit hydrogens on the structure which was then conjugate gradient minimized for 50 steps using the Dreiding forcefield. The HP pattern was enforced by only allowing hydrophobic amino acids into the rotamer groups for the optimized a and d positions. The hydrophobic group consisted of Ala, Val, Leu, Ile, Met, Phe, Tyr and Trp for a total of 238 rotamers per position. Homodimer symmetry was enforced by penalizing by 100 kcal/mol rotamer pairs that violate sequence symmetry. Different rotamers of the same amino acid were allowed at symmetry related positions. The asparagine that occupies the a position at residue 16 was left in the template and not optimized. A $10^6$ step Monte Carlo search run at a temperature of 1000 K generated the list of candidate sequences rank ordered by their score. To test reproducibility, the search was repeated three times with different random number seeds and all trials provided essentially identical results. The Monte Carlo searches took about 90 minutes. All calculations in this work were performed on a Silicon Graphics 200 MHz R4400 processor.

Optimizing the 16 a and d positions each with 238 possible hydrophobic rotamers results in $238^{16}$ or $10^{38}$ rotamer sequences. The DEE algorithm finds the global optimum in three minutes, including rotamer energy calculation time. The DEE solution matches the naturally occurring GCN4-p1 sequence of a and d residues for all of the 16 positions. A one million step Monte Carlo search run at a temperature of 1000 K generated the list of sequences rank ordered by their score. To test reproducibility, the search was repeated three times with different random number seeds and all trials provided essentially identical results. The second best sequence is a Val 30 to Ala mutation and lies three kcal/mol above the ground state sequence. Within the top 15 sequences up to six mutations from the ground state sequence are tolerated, indicating that a variety of packing arrangements are available even for a small coiled coil. Eight sequences with a range of stabilities were selected for experimental testing, including six from the top 15 and two more about 15 kcal/mol higher in energy, the 56th and 70th in the list (Table 1) (SEQ ID NOS:23 to 30).

TABLE 1

| Name | Sequence | Rank | Energy |
|---|---|---|---|
| PDA-3H[b] | RMKQLEDKVEELLSKNYHLENEVARLKKLVGER (SEQ ID NO:23) | 1 | -118.1 |
| PDA-3A | RMKQLEDKVEELLSKNYHLENEVARLKKLAGER (SEQ ID NO:24) | 2 | -115.3 |
| PDA-3G | RMKQLEDKVEELLSKNYHLENEMARLKKLVGER (SEQ ID NO:25) | 5 | -112.8 |
| PDA-3B | RLKQMEDKVEELLSKNYHLENEVARLKKLVGER (SEQ ID NO:26) | 6 | -112.6 |
| PDA-3D | RLKQMEDKVEELLSKNYHLENEVARLKKLAGER (SEQ ID NO:27) | 13 | -109.7 |
| PDA-3C | RMKQWEDKAEELLSKNYHLENEVARLKKLVGER (SEQ ID NO:28) | 14 | -109.6 |
| PDA-3F | RMKQFEDKVEELLSKNYHLENEVARLKKLVGER (SEQ ID NO:29) | 56 | -103.9 |
| PDA-3E | RMKQLEDKVEELLSKNYHAENEVARLKKLVGER (SEQ ID NO:30) | 70 | -103.1 |

Thirty-three residue peptides were synthesized on an Applied Biosystems Model 433 Å peptide synthesizer using Fmoc chemistry, HBTU activation and a modified Rink amide resin from Novabiochem. Standard 0.1 mmol coupling cycles were used and amino termini were acetylated. Peptides were cleaved from the resin by treating approximately 200 mg of resin with 2 mL trifluoroacetic acid (TFA) and 100 $\mu$L water, 100 $\mu$L thioanisole, 50 $\mu$L ethanedithiol and 150 mg phenol as scavengers. The peptides were isolated and purified by precipitation and repeated washing with cold methyl tert-butyl ether followed by reverse phase HPLC on a Vydac c8 column (25 cm by 22 mm) with a linear acetonitrile-water gradient containing 0.1% TFA. Peptides were then lyophilized and stored at −20° C. until use. Plasma desorption mass spectrometry found all molecular weights to be within one unit of the expected masses.

Circular Dichroism

CD spectra were measured on an Aviv 62DS spectrometer at pH 7.0 in 50 mM phosphate, 150 mM NaCl and 40 $\mu$M peptide. A 1 mm pathlength cell was used and the temperature was controlled by a thermoelectric unit. Thermal melts were performed in the same buffer using two degree temperature increments with an averaging time of 10 s and an equilibration time of 90 s. $T_m$ values were derived from the ellipticity at 222 nm ($[\theta]_{222}$) by evaluating the minimum of the $d[\theta]_{222}/dT^{-1}$ versus T plot (Cantor & Schimmel, Biophysical Chemistry. New York: W. H. Freemant and Company, 1980). The $T_m$'s were reproducible to within one degree. Peptide concentrations were determined from the tyrosine absorbance at 275 nm (Huyghues-Despointes, et al., supra).

Size Exclusion Chromatography:

Size exclusion chromatography was performed with a Synchropak GPC 100 column (25 cm by 4.6 mm) at pH 7.0 in 50 mM phosphate and 150 mM NaCl at 0° C. GCN4-p1 and p-LI (Harbury, et al., Science 262:1401 (1993)) were used as size standards. 10 $\mu$l injections of 1 mM peptide solution were chromatographed at 0.20 ml/min and monitored at 275 nm. Peptide concentrations were approximately 60 $\mu$M as estimated from peak heights. Samples were run in triplicate.

The designed a and d sequences were synthesized as above using the GCN4-p1 sequence for the b·c and e·f·g positions. Standard solid phase techniques were used and following HPLC purification, the identities of the peptides were confirmed by mass spectrometry. Circular dichroism spectroscopy (CD) was used to assay the secondary structure and thermal stability of the designed peptides. The CD spectra of all the peptides at 1° C. and a concentration of 40 mM exhibit minima at 208 and 222 nm and a maximum at 195 nm, which are diagnostic for α helices (data not shown). The ellipticity values at 222 nm indicate that all of the peptides are >85% helical (approximately −28000 deg cm$^2$/dmol), with the exception of PDA-3C (SEQ ID NO:28) which is 75% helical at 40 mM but increases to 90% helical at 170 mM (Table 2).

TABLE 2

CD data and calculated structural properties of the PDA peptides.

| Name | $-[\theta]_{222}$ (deg cm²/dmol) | $T_m$ (° C.) | $E_{MC}$ (kcal/ mol) | $\Delta A_{np}$ (Å²) | $\Delta A_p$ (Å²) | Vol (Å³) | Rot bonds | $E_{CQ}$ (kcal/ mol) | $E_{CG}$ (kcal/ mol) | $E_{vdW}$ (kcal/ mol) | Npb | Pb |
|---|---|---|---|---|---|---|---|---|---|---|---|---|
| PDA-3H (SEQ ID NO:23) | 33000 | 57 | −118.1 | 2967 | 2341 | 1830 | 28 | −234 | −308 | 409 | 207 | 128 |
| PDA-3A (SEQ ID NO:24) | 30300 | 48 | −115.3 | 2910 | 2361 | 1725 | 26 | −232 | −312 | 400 | 203 | 128 |
| PDA-3B (SEQ ID NO:26) | 28200 | 47 | −112.6 | 2977 | 2372 | 1830 | 28 | −242 | −306 | 379 | 210 | 127 |
| PDA-3G (SEQ ID NO:25) | 30700 | 47 | −112.8 | 3003 | 2383 | 1878 | 32 | −240 | −309 | 439 | 212 | 128 |
| PDA-3F (SEQ ID NO:29) | 28800 | 39 | −103.9 | 3000 | 2336 | 1872 | 28 | −188 | −302 | 420 | 212 | 128 |
| PDA-3D (SEQ ID NO:27) | 27800 | 39 | −109.7 | 2920 | 2392 | 1725 | 26 | −240 | −310 | 370 | 206 | 127 |
| PDA-3C (SEQ ID NO:28) | 24100 | 26 | −109.6 | 2878 | 2400 | 1843 | 26 | −149 | −304 | 398 | 215 | 129 |
| PDA-3E (SEQ ID NO:30) | 27500 | 24 | −103.1 | 2882 | 2361 | 1674 | 24 | −179 | −309 | 411 | 203 | 127 |

*$E_{MC}$ is the Monte Carlo energy; $\Delta A_{np}$ and $\Delta A_p$ are the changes in solvent accessible non-polar and polar surface areas upon folding, respectively; $E_{CQ}$ is the electrostatic energy using equilibrated charges; $E_{CG}$ is the electrostatic energy using Gasteiger charges; $E_{vdW}$ is the van der Waals energy; Vol is the side chain van der Waals volume; Rot bonds is the number of side chain rotatable bonds (excluding methyl rotors); Npb and Pb are the number of buried non-polar atoms, respectively.

The melting temperatures ($T_m$'s) show a broad range of values (data not shown), with 6 of the 8 peptides melting at greater than physiological temperature. Also, the $T_m$'s were not correlated to the number of sequence differences from GCN4-p1. Single amino acid changes resulted in some of the most and least stable peptides, demonstrating the importance of specificity in sequence selection.

Size exclusion chromatography confirmed the dimeric nature of these designed peptides. Using coiled coil peptides of known oligomerization state as standards, the PDA peptides (SEQ ID NOS:23 to 30) migrated as dimers. This result is consistent with the appearance of β-branched residues at a positions and leucines at d positions, which have been shown previously to favor dimerization over other possible oligomerization states (Harbury, et al., supra).

The characterization of the PDA peptides (SEQ ID NOS:23 to 30) demonstrates the successful design of several stable dimeric helical coiled coils. The sequences were automatically generated in the context of the design paradigm by the simulation module using well-defined inputs that explicitly consider the HP patterning and steric specificity of protein structure. Two dimensional nuclear magnetic resonance experiments aimed at probing the specificity of the tertiary packing are the focus of further studies on these peptides. Initial experiments show significant protection of amide protons from chemical exchange and chemical shift dispersion comparable to GCN4-p1 (unpublished results) (Oas, et al., Biochemistry 29:2891 (1990)); Goodman & Kim, Biochem. 30:11615 (1991)).

Data Analysis and Design Feedback

A detailed analysis of the correspondence between the theoretical and experimental potential surfaces, and hence an estimate of the accuracy of the simulation cost function, was enabled by the collection of experimental data. Using thermal stability as a measure of design performance, melting temperatures of the PDA peptides (SEQ ID NOS:23 to 30) were plotted against the sequence scores found in the Monte Carlo search (FIG. 6). The modest correlation, 0.67, in the plot shows that while an exclusively van der Waals scoring function can screen for stable sequences, it does not accurately predict relative stabilities. In order to address this issue, correlations between calculated structural properties and $T_m$'s were systematically examined using quantitative structure activity relationships (QSAR), which is a statistical technique commonly used in structure based drug design (Hopfinger, J. Med. Chem. 28:1133 (1985)).

Table 2 lists various molecular properties of the PDA peptides (SEQ ID NOS:23 to 30) in addition to the van der Waals based Monte Carlo scores and the experimentally determined $T_m$'s. A wide range of properties was examined, including molecular mechanics components, such as electrostatic energies, and geometric measures, such as volume. The goal of QSAR is the generation of equations that closely approximate the experimental quantity, in this case Tm, as a function of the calculated properties. Such equations suggest which properties can be used in an improved cost function. The PDA analysis module employs genetic function approximation (GFA) (Rogers & Hopfinger, J. Chem. Inf. Comput. Scie. 34:854 (1994)), a novel method to optimize QSAR equations that selects which properties are to be included and the relative weightings of the properties using a genetic algorithm. GFA accomplishes an efficient search of the space of possible equations and robustly generates a list of equations ranked by their correlation to the data.

Equations are scored by lack of fit (LOF), a weighted least square error measure that resists overfitting by penalizing equations with more terms (Rogers & Hopfinger, supra). GFA optimizes both the length and the composition of the equations and, by generating a set of QSAR equations, clarifies combinations of properties that fit well and properties that recur in many equations. All of the top five equations that correct the simulation energy ($E_{MC}$) contain burial of nonpolar surface area, $\Delta A_{np}$ (Table 3).

TABLE 3

Top five QSAR equations generated by GFA with LOF, correlation coefficient and cross validation scores.

| QSAR equation | LOF | $r^2$ | $CVr^2$ |
|---|---|---|---|
| $-1.44*E_{MC} + 0.14*\Delta A_{np} - 0.73*Npb$ | 16.23 | .98 | .78 |
| $-1.78*E_{MC} + 0.20*\Delta A_{np} - 2.43*Rot$ | 23.13 | .97 | .75 |
| $-1.59*E_{MC} + 0.17*\Delta A_{np} - 0.05*Vol$ | 24.57 | .97 | .36 |
| $-1.54*E_{MC} + 0.11*\Delta A_{np}$ | 25.45 | .91 | .80 |
| $-1.60*E_{MC} + 0.09*\Delta A_{np} - 0.12*\Delta A_p$ | 33.88 | .96 | .90 |

$\Delta A_{np}$ and $\Delta A_p$ are nonpolar and polar surface buried upon folding, respectively. Vol is side chain volume, Npb is the number of buried nonpolar atoms and Rot is the number of buried rotatable bonds.

The presence of $\Delta A_{np}$ in all of the top equations, in addition to the low LOF of the QSAR containing only $E_{MC}$ and $\Delta A_{np}$, strongly implicates nonpolar surface burial as a critical property for predicting peptide stability. This conclusion is not surprising given the role of the hydrophobic effect in protein energetics (Dill, Biochem. 29:7133 (1990)).

Properties were calculated using BIOGRAF and the Dreiding forcefield. Solvent accessible surface areas were calculated with the Connolly algorithm (Connolly, (1983) (supra)) using a probe radius of 1.4 Å and a dot density of 10 Å$^{-2}$. Volumes were calculated as the sum of the van der Waals volumes of the side chains that were optimized. The number of buried polar and nonpolar heavy atoms were defined as atoms, with their attached hydrogens, that expose less than 5 Å$^2$ in the surface area calculation. Electrostatic energies were calculated using a dielectric of one and no cutoff was set for calculation of non-bonded energies. Charge equilibration charges (Rappe & Goddard III, J. Phys. Chem. 95:3358 (1991) and Gasteiger (Gasteiger & Marsili, Tetrahedron 36:3219 (1980) charges were used to generate electrostatic energies. Charge equilibration charges were manually adjusted to provide neutral backbones and neutral side chains in order to prevent spurious monopole effects. The selection of properties was limited by the requirement that properties could not be highly correlated. Correlated properties cannot be differentiated by QSAR techniques and only create redundancy in the derived relations.

Genetic function approximation (GFA) was performed in the CERIUS2 simulation package version 1.6 (Biosym/ Molecular Simulations, San Diego, Calif.). An initial population of 300 equations was generated consisting of random combinations of three properties. Only linear terms were used and initial coefficients were determined by least squares regression for each set of properties. Redundant equations were eliminated and 10000 generations of random crossover mutations were performed. If a child had a better score than the worst equation in the population, the child replaced the worst equation. Also, mutation operators that add or remove terms had a 50% probability of being applied each generation, but these mutations were only accepted if the score was improved. No equation with greater than three terms was allowed. Equations were scored during evolution using the lack of fit (LOF) parameter, a scaled least square error (LSE) measure that penalizes equations with more terms and hence resists overfitting. LOF is defined as:

$$LOF = \frac{LSE}{\left(1 - \frac{2C}{M}\right)^{2'}}$$

where c is the number of terms in the equation and M is the number of data points. Five different randomized runs were done and the final equation populations were pooled. Only equations containing the simulation energy, $E_{MC}$, were considered which resulted in 108 equations ranked by their LOF.

To assess the predictive power of these QSAR equations, as well as their robustness, cross validation analysis was carried out. Each peptide was sequentially removed from the data set and the coefficients of the equation in question were refit. This new equation was then used to predict the withheld data point. When all of the data points had been predicted in this manner, their correlation to the measured $T_m$'s was computed (Table 3). Only the $E_{MC}/\Delta A_{np}$ QSAR and the $E_{MC}/\Delta A_{np}/\Delta A_p$ QSAR performed well in cross validation. The $E_{MC}/\Delta A_{np}$ equation could not be expected to fit the data as smoothly as QSAR's with three terms and hence had a lower cross validated $r^2$. However, all other two term QSAR's had LOF scores greater than 48 and cross validation correlations less than 0.55 (data not shown). The QSAR analysis independently predicted with no subjective bias that consideration of nonpolar and polar surface area burial is necessary to improve the simulation. This result is consistent with previous studies on atomic salvation potentials (Eisenberg, et al., (1986) (supra); Wesson, et al., Protein Sci. 1:227 (1992)). Further, simpler structural measures, such as number of buried atoms, that reflect underlying principles such as hydrophobic salvation (Chan, et al., Science 267:1463 (1995)) were not deemed as significant by the QSAR analysis. These results justify the cost of calculating actual surface areas, though in some studies simpler potentials have been shown to perform well (van Gunsteren, et al. J. Mol. Biol 227:389 (1992)).

$\Delta a_{np}$ and $\Delta A_p$ were introduced into the simulation module to correct the cost function. Contributions to surface burial from rotamer/template and rotamer/rotamer contacts were calculated and used in the interaction potential. Independently counting buried surface from different rotamer pairs, which is necessary in DEE, leads to overestimation of burial because the radii of solvent accessible surfaces are much larger than the van der Waals contact radii and hence can overlap greatly in a close packed protein core. To account for this discrepancy, the areas used in the QSAR were recalculated using the pairwise area method and a new $E_{MC}/\Delta A_{np}/\Delta A_p$ QSAR equation was generated. The ratios of the $E_{MC}$ coefficient to the $\Delta A_{np}$ and $\Delta A_p$ coefficients are scale factors that are used in the simulation module to convert buried surface area into energy, i.e. atomic solvation parameters. Thermal stabilities are predicted well by this cost function (FIG. 6B). In addition, the improved cost function still predicts the naturally occurring GCN4-p1 sequence as the ground state. The surface area to energy scale factors, 16 cal/mol/Å$^2$ favoring nonpolar area burial and 86 cal/mol/Å$^2$ opposing polar area burial, are similar in sign, scale and relative magnitude to solvation potential parameters derived from small molecule transfer data (Wesson & Eisenberg, supra).

λ Repressor Mutants:

To demonstrate the generality of the cost function, other proteins were examined using the simulation module. A library of core mutants of the DNA binding protein λ repressor has been extensively characterized by Sauer and coworkers (Lim & Sauer, J. Mol. Biol. 219:359 (1991)). Template coordinates were taken from PDB file 1 LMB (Beamer & Pabo, J. Mol. Biol. 227:177 (1992)). The subunit designated chain 4 in the PDB file was removed from the context of the rest of the structure (accompanying subunit and DNA) and using BIOGRAF explicit hydrogens were added. The hydrophobic residues with side chains within 5 Å of the three mutation sites (V36 M40 V47) are Y22, L31, A37, M42, L50, F51, L64, L65, I68 and L69. All of these residues are greater than 80% buried except for M42 which is 65% buried and L64 which is 45% buried. A37 only has one possible rotamer and hence was not optimized. The other nine residues in the 5 Å sphere were allowed to take any rotamer conformation of their amino acid ("floated").

The mutation sites were allowed any rotamer of the amino acid sequence in question. Depending on the mutant sequence, $5 \times 10^{16}$ to $7 \times 10^{18}$ conformations were possible. Rotamer energy and DEE calculation times were 2 to 4 minutes. The combined activity score is that of Hellinga and Richards (Hellinga, et al., (1994) (supra)). Seventy-eight of the 125 possible combinations were generated. Also, this dataset has been used to test several computational schemes and can serve as a basis for comparing different forcefields (Lee & Levitt, Nature 352:448 (1991); van Gunsteren & Mark, supra; Hellinga, et al., (1994) (supra)). The simulation module, using the cost function found by QSAR, was used to find the optimal conformation and energy for each mutant sequence. All hydrophobic residues within 5 Å of the three mutation sites were also left free to be relaxed by the algorithm. This 5 Å sphere contained 12 residues, a significantly larger problem than previous efforts (Lee & Levitt, supra; Hellinga, (1994) (supra)), that were rapidly optimized by the DEE component of the simulation module. The rank correlation of the predicted energy to the combined activity score proposed by Hellinga and Richards is shown in FIG. 7. The wildtype has the lowest energy of the 125 possible sequences and the correlation is essentially equivalent to previously published results which demonstrates that the QSAR corrected cost function is not specific for coiled coils and can model other proteins adequately.

Example 2

Automated Design of the Surface Positions of Protein Helices

GCN4-p1, a homodimeric coiled coil, was again selected as the model system because it can be readily synthesized by solid phase techniques and its helical secondary structure and dimeric tertiary organization ease characterization. The sequences of homodimeric coiled coils display a seven residue periodic hydrophobic and polar pattern called a heptad repeat, (a·b·c·d·e·f·g) (Cohen & Parry, supra). The a and d positions are buried at the dimer interface and are usually hydrophobic, whereas the b, c, e, f, and g positions are solvent exposed and usually polar (FIG. 5). Examination of the crystal structure of GCN4-p1 (O'Shea, et al., supra) shows that the b, c, and f side chains extend into solvent and expose at least 55% of their surface area. In contrast, the e and g residues bury from 50 to 90% of their surface area by packing against the a and d residues of the opposing helix. We selected the 12 b, c, and f residue positions for surface sequence design: positions 3, 4, 7, 10, 11, 14, 17, 18, 21, 24, 25, and 28 using the numbering from PDB entry 2zta (Bernstein, et al., J. Mol. Biol. 112:535 (1977)). The remainder of the protein structure, including all other side chains and the backbone, was used as the template for sequence selection calculations. The symmetry of the dimer and lack of interactions of surface residues between the subunits allowed independent design of each subunit, thereby significantly reducing the size of the sequence optimization problem.

All possible sequences of hydrophilic amino acids (D, E, N, Q, K, R, S, T, A, and H) for the 12 surface positions were screened by our design algorithm. The torsional flexibility of the amino acid side chains was accounted for by considering a discrete set of all allowed conformers of each side chain, called rotamers (Ponder, et al., (1987( (supra); Dunbrack, et al., Struc. Biol. Vol. 1(5):334–340 (1994)). Optimizing the 12 b, c, and f positions each with 10 possible amino acids results in $10^{12}$ possible sequences which corresponds to $\sim 10^{28}$ rotamer sequences when using the Dunbrack and Karplus backbone-dependent rotamer library. The immense search problem presented by rotamer sequence optimization is overcome by application of the Dead-End Elimination (DEE) theorem (Desmet, et al., (1992( (supra); Desmet, et al., (1994) (supra); Goldstein, (1994) (supra)). Our implementation of the DEE theorem extends its utility to sequence design and rapidly finds the globally optimal sequence in its optimal conformation.

We examined three potential-energy functions for their effectiveness in scoring surface sequences. Each candidate scoring function was used to design the b, c, and f positions of the model coiled coil and the resulting peptide was synthesized and characterized to assess design performance. A hydrogen-bond potential was used to check if predicted hydrogen bonds can contribute to designed protein stability, as expected from studies of hydrogen bonding in proteins and peptides (Stickle, et al., supra; Huyghues-Despointes, et al., supra). Optimizing sequences for hydrogen bonding, however, often buries polar protons that are not involved in hydrogen bonds. This uncompensated loss of potential hydrogen-bond donors to water prompted examination of a second scoring scheme consisting of a hydrogen-bond potential in conjunction with a penalty for burial of polar protons (Eisenberg, (1986) (supra)). We tested a third scoring scheme which augments the hydrogen bond potential with the empirically derived helix propensities of Baldwin and coworkers (Chakrabartty, et al., supra). Although the physical basis of helix propensities is unclear, they can have a significant effect on protein stability and can potentially be used to improve protein designs (O'Neil & DeGrado, 1990; Zhang, et al., Biochem. 30:2012 (1991); Blaber, et al., Science 260:1637 (1993); O'shea, et al., 1993; Villegas, et al., Folding and Design 1:29 (1996)). A van der Waals potential was used in all cases to account for packing interactions and excluded volume.

Several other sequences for the b, c and f positions were also synthesized and characterized to help discern the relative importance of the hydrogen-bonding and helix-propensity potentials. The sequence designed with the hydrogen-bond potential was randomly scrambled, thereby disrupting the designed interactions but not changing the helix propensity of the sequence. Also, the sequence with the maximum possible helix propensity, all positions set to alanine, was made. Finally, to serve as undesigned controls, the naturally occurring GCN4-p1 sequence and a sequence randomly selected from the hydrophilic amino acid set were synthesized and studied.

Sequence Design: Scoring Functions and DEE:

The protein structure was modeled on the backbone coordinates of GCN4-p1, PDB record 2zta (Bernstein, et al., supra; O'Shea, et al., supra). Atoms of all side chains not optimized were left in their crystallographically determined positions. The program BIOGRAF (Molecular Simulations Incorporated, San Diego, Calif.) was used to generate explicit hydrogens on the structure which was then conjugate gradient minimized for 50 steps using the DREIDING forcefield (Mayo, et al., 1990, supra). The symmetry of the dimer and lack of interactions of surface residues between the subunits allowed independent design of each subunit. All computations were done using the first monomer to appear in 2zta (chain A). A backbone-dependent rotamer library was used (Dunbrack, et al. (1993) (supra)). $c_3$ angles that were undetermined from the database statistics were assigned the following values: Arg, −60°, 60°, and 180°; Gln, −120°, −60°, 0°, 60°, 120°, and 180°; Glu, 0°, 60°, and 120°; Lys, −60°, 60°, and 180°. $c_4$ angles that were undetermined from the database statistics were assigned the following values: Arg, −120°, −60°, 60°, 120°, and 180°; Lys, −60°, 60°, and 180°. Rotamers with combinations of $c_3$ and $c_4$ that resulted in sequential $g^+/g^-$ or $g^-/g^+$ angles were eliminated. Uncharged His rotamers were used. A Lennard-Jones 12-6 potential with van der Waals radii scaled by 0.9 (Dahiyat, et al., First fully automatic design of a protein achieved by Caltech scientists, new press release (1997) was used for van der Waals interactions. The hydrogen bond potential consisted of a distance-dependent term and an angle-dependent term, as depicted in Equation 9, above. This hydrogen bond potential is based on the potential used in DREIDING, with more restrictive angle-dependent terms to limit the occurrence of unfavorable hydrogen bond geometries. The angle term varies depending on the hybridization state of the donor and acceptor, as shown in Equations 10 to 13, above.

In Equations 10–13, $\theta$ is the donor-hydrogen-acceptor angle, $\phi$ is the hydrogen-acceptor-base angle (the base is the atom attached to the acceptor, for example the carbonyl carbon is the base for a carbonyl oxygen acceptor), and $\phi$ is the angle between the normals of the planes defined by the six atoms attached to the $sp^2$ centers (the supplement of $\phi$ is used when $\phi$ is less than 90°). The hydrogen-bond function is only evaluated when 2.6 Å<R<3.2Å, $\phi$>90°, f−109.50°<90° for the $sp^3$ donor −$sp^3$ acceptor case, and, $\phi$<90° for the $sp^3$ donor −$sp^2$ acceptor case; no switching functions were used. Template donors and acceptors that were involved in template-template hydrogen bonds were not included in the donor and acceptor lists. For the purpose of exclusion, a template-template hydrogen bond was considered to exist when 2.5 Å≧R≧3.3 Å and $\theta$≧135°. A penalty of 2 kcal/mol for polar hydrogen burial, when used, was only applied to buried polar hydrogens not involved in hydrogen bonds, where a hydrogen bond was considered to exist when $E_{HB}$ was less than −2 kcal/mol. This penalty was not applied to template hydrogens. The hydrogen-bond potential was also supplemented with a weak coulombic term that included a distance-dependent dielectric constant of 40R, where R is the interatomic distance. Partial atomic charges were only applied to polar functional groups. A net formal charge of +1 was used for Arg and Lys and a net formal charge of −1 was used for Asp and Glu. Energies associated with α-helical propensities were calculated using equation 14, above. In Equation 14, $E_\alpha$ is the energy of α-helical propensity, $\Delta G°_{aa}$ is the standard free energy of helix propagation of the amino acid, and $\Delta G°_{ala}$ is the standard free energy of helix propagation of alanine used as a standard, and $N_{ss}$ is the propensity scale factor which was set to 3.0. This potential was selected in order to scale the propensity energies to a similar range as the other terms in the scoring function. The DEE optimization followed the methods of our previous work (Dahiyat, et al., (1996) (supra)).

Calculations were performed on either a 12 processor, R10000-based Silicon Graphics Power Challenge or a 512 node Intel Delta.

Peptide synthesis and purification and CD analysis was as in Example 1. NMR samples were prepared in 90/10 $H_2O$/$D_2O$ and 50 mM sodium phosphate buffer at pH 7.0. Spectra were acquired on a Varian Unityplus 600 MHz spectrometer at 25° C. 32 transients were acquired with 1.5 seconds of solvent presaturation used for water suppression. Samples were ~1 mM. Size exclusion chromatography was performed with a PolyLC hydroxyethyl A column (20 cm×9 mm) at pH 7.0 in 50 mM phosphate and 150 mM NaCl at 0° C. GCN4-p1 and p-LI (Harbury, et al., supra) were used as size standards for dimer and tetramer, respectively. 5 µl injections of ~1 mM peptide solution were chromatographed at 0.50 ml/min and monitored at 214 nm. Samples were run in triplicate.

The surface sequences of all of the peptides examined in this study are shown in Table 4.

TABLE 4

Sequences and properties of the synthesized peptides

| Peptide | Design method | Surface Sequence bcf bcf bcf bcf | $T_m$ | $\Sigma\Delta G°$ (° C.) | N (kcal/mol) |
|---|---|---|---|---|---|
| GCN4-p1 | none | KQD EES YHN ARK (SEQ ID NO:31) | 57 | 3.831 | 2 |
| 6A | HB | EKD RER RRE RRE (SEQ ID NO:32) | 71 | 2.193 | 2 |
| 6B | HB + PB | EKQ KER ERE ERQ (SEQ ID NO:33) | 72 | 2.868 | 2 |
| 6C | HB + HP | ARA AAA RRR ARA (SEQ ID NO:34) | 69 | −2.041 | 2 |
| 6D | scrambled HB | REE RRR EDR KRE (SEQ ID NO:35) | 71 | 2.193 | 2 |
| 6E | random polar | NTR AKS ANH NTQ (SEQ ID NO:36) | 15 | 4.954 | 2 |

TABLE 4-continued

Sequences and properties of the synthesized peptides

| Peptide | Design method | Surface Sequence bcf bcf bcf bcf | $T_m$ | $\Sigma\Delta G°$ (° C.) | N (kcal/mol) |
|---|---|---|---|---|---|
| 6F | poly(Ala) | AAA AAA AAA AAA (SEQ ID NO:37) | 73 | −3.096 | 4 |

For clarity only the designed surface residues are shown and they are grouped by position (b, c, and f). The sequence numbers of the designed positions are: 3, 4, 7, 10, 11, 14, 17, 18, 21, 24, 25, and 28. Melting temperatures ($T_m$'s) were determined by circular dichroism and oligomerization states (N) were determined by size exclusion chromatography. $\Sigma\Delta G°$ is the sum of the standard free energy of helix propagation of the 12 b, c, and f positions (Chakrabartty, et al., 1994). Abbreviations for design methods are: hydrogen bonds (HB), polar hydrogen burial penalty (PB), and helix propensity (HP).

Sequence 6A (SEQ ID NO:32), designed with a hydrogen-bond potential, has a preponderance of Arg and Glu residues that are predicted to form numerous hydrogen bonds to each other. These long chain amino acids are favored because they can extend across turns of the helix to interact with each other and with the backbone. When the optimal geometry of the scrambled 6A sequence, 6D (SEQ ID NO:35), was found with DEE, far fewer hydrogen bonding interactions were present and its score was much worse than 6A's (SEQ ID NO:32). 6B (SEQ ID NO:33), designed with a polar hydrogen burial penalty in addition to a hydrogen-bond potential, is still dominated by long residues such as Lys, Glu and Gln but has fewer Arg. Because Arg has more polar hydrogens than the other amino acids, it more often buries nonhydrogen-bonded protons and therefore is disfavored when using this potential function. 6C (SEQ ID NO:34) was designed with a hydrogen-bond potential and helix propensity in the scoring function and consists entirely of Ala and Arg residues, the amino acids with the highest helix propensities (Chakrabartty, et al., supra). The Arg residues form hydrogen bonds with Glu residues at nearby e and g positions. The random hydrophilic sequence, 6E (SEQ ID NO:36), possesses no hydrogen bonds and scores very poorly with all of the potential functions used.

The secondary structures and thermal stabilities of the peptides were assessed by circular dichroism (CD) spectroscopy. The CD spectra of the peptides at 1° C. and 40 μM are characteristic of α helices, with minima at 208 and 222 nm, except for the random surface sequence peptide 6E (SEQ ID NO:36). 6E has a spectrum suggestive of a mixture of a helix and random coil with a $[\theta]_{222}$ of −12000 deg cm²/dmol, while all the other peptides are greater than 90% helical with $[\theta]_{222}$ of less than −30000 deg cm²/dmol. The melting temperatures ($T_m$'s) of the designed peptides are 12–16° C. higher than the $T_m$ of GCN4-p1 (SEQ ID NO:31), with the exception of 6E (SEQ ID NO:36) which has a $T_m$ of 15° C. CD spectra taken before and after melts were identical indicating reversible thermal denaturation. The redesign of surface positions of this coiled coil produces structures that are much more stable than wildtype GCN4-p1 (SEQ ID NO:31), while a random hydrophilic sequence largely disrupts the peptide's stability.

Size exclusion chromatography (SEC) showed that all the peptides were dimers except for 6F (SEQ ID NO:37), the all Ala surface sequence, which migrated as a tetramer. These data show that surface redesign did not change the tertiary structure of these peptides, in contrast to some core redesigns (Harbury, et al., supra). In addition, nuclear magnetic resonance (NMR) spectra of the peptides at ~1 mM showed chemical shift dispersion similar to GCN4-p1 (SEQ ID NO:31) (data not shown).

Peptide 6A (SEQ ID NO:32), designed with a hydrogen-bond potential, melts at 71° C. versus 57° C. for GCN4-p1 (SEQ ID NO:31), demonstrating that rational design of surface residues can produce structures that are markedly more stable than naturally occurring coiled coils. This gain in stability is probably not due to improved hydrogen bonding since 6D (SEQ ID NO:35), which has the same surface amino acid composition as 6A (SEQ ID NO:32) but a scrambled sequence and no predicted hydrogen bonds, also melts at 71° C. Further, 6B (SEQ ID NO:33) was designed with a different scoring function and has a different sequence and set of predicted hydrogen bonds but a very similar $T_m$ of 72° C.

An alternative explanation for the increased stability of these sequences relative to GCN4-p1 (SEQ ID NO:31) is their higher helix propensity. The long polar residues selected by the hydrogen bond potential, Lys, Glu, Arg and Gln, are also among the best helix formers (Chakrabartty, et al., supra). Since the effect of helix propensity is not as dependent on sequence position as that of hydrogen bonding, especially far from the helix ends, little effect would be expected from scrambling the sequence of 6A (SEQ ID NO:32). A rough measure of the helix propensity of the surface sequences, the sum of the standard free energies of helix propagation ($\Sigma\Delta G°$) (Chakrabartty, et al., supra), corresponds to the peptides' thermal stabilities (Table 4). Though $\Sigma\Delta G°$ matches the trend in peptide stability, it is not quantitatively correlated to the increased stability of these coiled coils.

Peptide 6C (SEQ ID NO:34) was designed with helix propensity as part of the scoring function and it has a $\Sigma\Delta G°$ of −2.041 kcal/mol. Though 6C (SEQ ID NO:34) is more stable than GCN4-p1 (SEQ ID NO:31), its $T_m$ of 69° C. is slightly lower than 6A (SEQ ID NO:32) and 6B (SEQ ID NO:33), in spite of 6C's (SEQ ID NO: 34) higher helix propensity. Similarly, 6F (SEQ ID NO:37) has the highest helix propensity possible with an all Ala sequence and a $\Sigma\Delta G°$ of −3.096 kcal/mol, but its $T_m$ of 73° C. is only marginally higher than that of 6A (SEQ ID NO:32) or 6B (SEQ ID NO:33). 6F (SEQ ID NO:37) also migrates as a tetramer during SEC, not a dimer, likely because its poly (Ala) surface exposes a large hydrophobic patch that could mediate association. Though the results for 6C (SEQ ID NO:34) and 6F (SEQ ID NO:37) support the conclusion that helix propensity is important for surface design, they point out possible limitations in using propensity exclusively. Increasing propensity does not necessarily confer the greatest stability on a structure, perhaps because other factors are being effected unfavorably. Also, as is evident from 6F (SEQ ID NO:37), changes in the tertiary structure of the protein can occur.

The characterization of these peptides clearly shows that surface residues have a dramatic impact on the stability of α-helical coiled coils. The wide range of stabilities displayed by the different surface designs is notable, with greater than a 50° C. spread between the random hydrophilic sequence ($T_m$ 15° C.) and the designed sequences ($T_m$ 69–72° C.). This result is consistent with studies on other proteins that demonstrated the importance of solvent exposed residues (O'Neil & DeGrado, 1990; Zhang, et al., 1991; Minor, et al., (1994) (supra); Smith, et al., *Science* 270:980–982 (1995)). Further, these designs have significantly higher $T_m$'s than the wildtype GCN4-p1 (SEQ ID NO:31) sequence, demonstrating that surface residues can be used to improve stability in protein design (O'shea, et al., supra). Though helix propensity appears to be more important than hydrogen bonding in stabilizing the designed coiled coils, hydrogen bonding could be important in the design and stabilization of other types of secondary structure.

Example 3

Design of a Protein Containing Core, Surface and Boundary Residues using van der Waals, H-bonding, Secondary Structure and Solvation Scoring Functions In this example, core, boundary and surface residue work was combined. In selecting a motif to test the integration of our design methodologies, we sought a protein fold that would be small enough to be both computationally and experimentally tractable, yet large enough to form an independently folded structure in the absence of disulfide bonds or met al binding sites. We chose the ββα motif typified by the zinc finger DNA binding module (Pavletich, et al. (1991) (supra)). Though it consists of less than 30 residues, this motif contains sheet, helix, and turn structures. Further, recent work by Imperiali and coworkers who designed a 23 residue peptide, containing an unusual amino acid (D-proline) and a non-natural amino acid (3-(1,10-phenanthrol-2-yl)-L-alanine), that takes this structure has demonstrated the ability of this fold to form in the absence of met al ions (Struthers, et al., 1996a). The Brookhaven Protein Data Bank (PDB) (Bernstein, et al., 1977) was examined for high resolution structures of the ββα motif, and the second zinc finger module of the DNA binding protein Zif268 (SEQ ID NO:1) (PDB code 1zaa) was selected as our design template (Pavletich, et al. (1991) (supra)). The backbone of the second module aligns very closely with the other two zinc fingers in Zif268 (SEQ ID NO:1) and with zinc fingers in other proteins and is therefore representative of this fold class. 28 residues were taken from the crystal structure starting at lysine 33 in the numbering of PDB entry 1zaa which corresponds to our position 1. The first 12 residues comprise the β sheet with a tight turn at the $6^{th}$ and $7^{th}$ positions. Two residues connect the sheet to the helix, which extends through position 26 and is capped by the last two residues.

In order to assign the residue positions in the template structure into core, surface or boundary classes, the extent of side-chain burial in Zif268 (SEQ ID NO:1) and the direction of the Cα–Cβ vectors were examined. The small size of this motif limits to one (position 5) the number of residues that can be assigned unambiguously to the core while six residues (positions 3, 12, 18, 21, 22, and 25) were classified as boundary. Three of these residues are from the sheet (positions 3, 5, and 12) and four are from the helix (positions 18, 21, 22, and 25). One of the zinc binding residues of Zif268 (SEQ ID NO:1) is in the core and two are in the boundary, but the fourth, position 8, has a Cα–Cβ vector directed away from the protein's geometric center and is therefore classified as a surface position. The other surface positions considered by the design algorithm are 4, 9, and 11 from the sheet, 15, 16, 17, 19, 20, and 23 from the helix and 14, 27, and 28 which cap the helix ends. The remaining exposed positions, which either were in turns, had irregular backbone dihedrals or were partially buried, were not included in the sequence selection for this initial study. As in our previous studies, the amino acids considered at the core positions during sequence selection were A, V, L, l, F, Y, and W; the amino acids considered at the surface positions were A, S, T, H, D, N, E, Q, K, and R; and the combined core and surface amino acid sets (16 amino acids) were considered at the boundary positions.

In total, 20 out of 28 positions of the template were optimized during sequence selection. The algorithm first selects Gly for all positions with φ angles greater than 0° in order to minimize backbone strain (residues 9 and 27). The 18 remaining residues were split into two sets and optimized separately to speed the calculation. One set contained the 1 core, the 6 boundary positions and position 8 which resulted in $1.2 \times 10^9$ possible amino acid sequences corresponding to $4.3 \times 10^{19}$ rotamer sequences. The other set contained the remaining 10 surface residues which had $10^{10}$ possible amino acid sequences and $4.1 \times 10^{23}$ rotamer sequences. The two groups do not interact strongly with each other making their sequence optimizations mutually independent, though there are strong interactions within each group. Each optimization was carried out with the non-optimized positions in the template set to the crystallographic coordinates.

The optimal sequences found from the two calculations were combined and are shown in FIG. 8 (SEQ ID NOS:1 and 2) aligned with the sequence from the second zinc finger of Zif268 (SEQ ID NO:1). Even though all of the hydrophilic amino acids were considered at each of the boundary positions, only nonpolar amino acids were selected. The calculated seven core and boundary positions form a well-packed buried cluster. The Phe side chains selected by the algorithm at the zinc binding His positions, 21 and 25, are 80% buried and the Ala at 5 is 100% buried while the Lys at 8 is greater than 60% exposed to solvent. The other boundary positions demonstrate the strong steric constraints on buried residues by packing similar side chains in an arrangement similar to Zif268. The calculated optimal configuration buried ~830 Å$^2$ of nonpolar surface area, with Phe 12 (96% buried) and Leu 18 (88% buried) anchoring the cluster. On the helix surface, the algorithm positions Asn 14 as a helix N-cap with a hydrogen bond between its side-chain carbonyl oxygen and the backbone amide proton of residue 16. The six charged residues on the helix form three pairs of hydrogen bonds, though in our coiled coil designs helical surface hydrogen bonds appeared to be less important than the overall helix propensity of the sequence. Positions 4 and 11 on the exposed sheet surface were selected to be Thr, one of the best β-sheet forming residues (Kim & Berg, 1993; Minor, et al., (1994) (supra); Smith, et al., (1995) (supra)).

Combining the 20 designed positions with the Zif268 (SEQ ID NO:1) amino acids at the remaining 8 sites results in a peptide with overall 39% (11/28) homology to Zif268 (SEQ ID NO:1), which reduces to 15% (3/20) homology when only the designed positions are considered. A BLAST (Altschul, et al., 1990) search of the non-redundant protein sequence database of the National Center for Biotechnology Information finds weak homology, less than 40%, to several zinc finger proteins and fragments of other unrelated proteins. None of the alignments had significance values less than 0.26. By objectively selecting 20 out of 28 residues on the Zif268 (SEQ ID NO:1) template, a peptide with little homology to known proteins and no zinc binding site was designed.

Experimental Characterization:

The far UV circular dichroism (CD) spectrum of the designed molecule, pda8d (SEQ ID NO:2), shows a maximum at 195 nm and minima at 218 nm and 208 nm, which is indicative of a folded structure. The thermal melt is weakly cooperative, with an inflection point at 39° C., and is completely reversible. The broad melt is consistent with a low enthalpy of folding which is expected for a motif with a small hydrophobic core. This behavior contrasts the uncooperative transitions observed for other short peptides (Weiss & Keutmann, 1990; Scholtz, et al., PNAS USA 88:2854 (1991); Struthers, et al., J. Am. Chem. Soc. 118:3073 (1996b)).

Sedimentation equilibrium studies at 100 $\mu$M and both 7° C. and 25° C. give a molecular mass of 3490, in good agreement with the calculated mass of 3362, indicating the peptide is monomeric. At concentrations greater than 500 $\mu$M, however, the data do not fit well to an ideal single species model. When the data were fit to a monomer-dimer-tetramer model, dissociation constants of 0.5–1.5 mM for monomer-to-dimer and greater than 4 mM for dimer-to-tetramer were found, though the interaction was too weak to accurately measure these values. Diffusion coefficient measurements using the water-sLED pulse sequence (Altieri, et al., 1995) agreed with the sedimentation results: at 100 $\mu$M pda8d has a diffusion coefficient close to that of a monomeric zinc finger control, while at 1.5 mM the diffusion coefficient is similar to that of protein G $\beta$1, a 56 residue protein. The CD spectrum of pda8d (SEQ ID NO:2) is concentration independent from 10 $\mu$M to 2.6 mM. NMR COSY spectra taken at 2.1 mM and 100 $\mu$M were almost identical with 5 of the H$\alpha$-HN crosspeaks shifted no more than 0.1 ppm and the rest of the crosspeaks remaining unchanged. These data indicate that pda8d undergoes a weak association at high concentration, but this association has essentially no effect on the peptide's structure.

The NMR chemical shifts of pda8d are well dispersed, suggesting that the protein is folded and well-ordered. The H$\alpha$-HN fingerprint region of the TOCSY spectrum is well-resolved with no overlapping resonances (FIG. (9A) and all of the H$\alpha$ and HN resonances have been assigned. NMR data were collected on a Varian Unityplus 600 MHz spectrometer equipped with a Nalorac inverse probe with a self-shielded z-gradient. NMR samples were prepared in 90/10 H$_2$O/D$_2$O or 99.9% D$_2$O with 50 mM sodium phosphate at pH 5.0. Sample pH was adjusted using a glass electrode with no correction for the effect of D$_2$O on measured pH. All spectra for assignments were collected at 7° C. Sample concentration was approximately 2 mM. NMR assignments were based on standard homonuclear methods using DQF-COSY, NOESY and TOCSY spectra (Wuthrich, NMR of Proteins and Nucleic Acids (John Wiley & Sons, New York, 1986). NOESY and TOCSY spectra were acquired with 2K points in F2 and 512 increments in F1 and DQF-COSY spectra were acquired with 4K points in F2 and 1024 increments in F1. All spectra were acquired with a spectral width of 7500 Hz and 32 transients. NOESY spectra were recorded with mixing times of 100 and 200 ms and TOCSY spectra were recorded with an isotropic mixing time of 80 ms. In TOCSY and DQF-COSY spectra water suppression was achieved by presaturation during a relaxation delay of 1.5 and 2.0 s, respectively. Water suppression in the NOESY spectra was accomplished with the WATERGATE pulse sequence (Piotto, et al., 1992). Chemical shifts were referenced to the HOD resonance. Spectra were zero-filled in both F2 and F1 and apodized with a shifted gaussian in F2 and a cosine bell in F1 (NOESY and TOCSY) or a 30° shifted sine bell in F2 and a shifted gaussian in F1 (DQF-COSY).

Water-sLED experiments (Altieri, et al., 1995) were run at 25° C. at 1.5 mM, 400 $\mu$M and 100 $\mu$M in 99.9% D$_2$O with 50 mM sodium phosphate at pH 5.0. Axial gradient field strength was varied from 3.26 to 53.1 G/cm and a diffusion time of 50 ms was used. Spectra were processed with 2 Hz line broadening and integrals of the aromatic and high field aliphatic protons were calculated and fit to an equation relating resonance amplitude to gradient strength in order to extract diffusion coefficients (Altieri, et al., 1995). Diffusion coefficients were $1.48 \times 10^{-7}$, $1.62 \times 10^{-7}$ and $1.73 \times 10^{-7}$ cm$^2$/s at 1.5 mM, 400 $\mu$M and 100 $\mu$M, respectively. The diffusion coefficient for the zinc finger monomer control was $1.72 \times 10^{-7}$ cm$^2$/s and for protein G b1 was $1.49 \times 10^{-7}$ cm$^2$/s.

All unambiguous sequential and medium-range NOEs are shown in FIG. 9A. H$\alpha$-HN and/or HN-HN NOEs were found for all pairs of residues except R6–17 and K16-E17, both of which have degenerate HN chemical shifts, and P2-Y3 which have degenerate H$\alpha$ chemical shifts. An NOE is present, however, from a P2 H$\delta$ to the Y3 HN analogous to sequential HN-HN connections. Also, strong K1 H$\alpha$ to P2 H$\delta$ NOEs are present and allowed completion of the resonance assignments.

The structure of pda8d (SEQ ID NO:2) as determined using 354 NOE restraints (12.6 restraints per residue) that were non-redundant with covalent structure. An ensemble of 32 structures (data not shown) was obtained using X-PLOR (Brunger, 1992) with standard protocols for hybrid distance geometry-simulated annealing. The structures in the ensemble had good covalent geometry and no NOE restraint violations greater than 0.3 Å. As shown in Table 5, the backbone was well defined with a root-mean-square (rms) deviation from the mean of 0.55 Å when the disordered termini (residues 1, 2, 27, and 28) were excluded. The rms deviation for the backbone (3–26) plus the buried side chains (residues 3, 5, 7, 12, 18, 21, 22, and 25) was 1.05 Å.

TABLE 5

NMR structure determination of pda8d (SEQ ID NO:2): distance restraints, structural statistics, atomic root-mean-square (rms) deviations, and comparison to the design target. <SA> are the 32 simulated annealing structures, SA is the average structure and SD is the standard deviation. The design target is the backbone of Zif268 (SEQ ID NO:1)

| Distance restraints | |
|---|---|
| Intraresidue | 148 |
| Sequential | 94 |
| Short range ($|i-j| = 2-5$ residues) | 78 |
| Long range ($|i-j| > 5$ residues) | 34 |
| Total | 354 |
| Structural statistics | |
| | <SA> ± SD |
| Rms deviation from distance restraints (Å) | 0.049 ± .004 |

TABLE 5-continued

NMR structure determination of pda8d (SEQ ID NO:2):
distance restraints, structural statistics, atomic root-
mean-square (rms) deviations, and comparison to the design
target. <SA> are the 32 simulated annealing structures,
SA is the average structure and SD is the standard deviation.
The design target is the backbone of Zif268 (SEQ ID NO:1)

Rms deviation from idealized geometry (Å)

| | |
|---|---|
| Bonds (Å) | 0.0051 ± 0.0004 |
| Angles (degrees) | 0.76 ± 0.04 |
| Impropers (degrees) | 0.56 ± 0.04 |

Atomic rms deviations (Å)*

| | <SA> vs. SA ± SD |
|---|---|
| Backbone | 0.55 ± 0.03 |
| Backbone + nonpolar side chains | 1.05 ± 0.06 |
| Heavy atoms | 1.25 ± 0.04 |

Atomic rms deviations between pda8d and the design target (Å)*

| | SA vs. target |
|---|---|
| Backbone | 1.04 |
| Heavy atoms | 2.15 |

*Atomic rms deviations are for residues 3 to 26, inclusive. The termini, residues 1, 2, 27, and 28, were highly disordered and had very few non-sequential or non-intraresidue contacts.

The NMR solution structure of pda8d (SEQ ID NO:2) shows that it folds into a bba motif with well-defined secondary structure elements and tertiary organization which match the design target. A direct comparison of the design template, the backbone of the second zinc finger of Zif268 (SEQ ID NO:1), to the pda8d solution structure highlights their similarity (data not shown). Alignment of the pda8d (SEQ ID NO:2) backbone to the design target is excellent, with an atomic rms deviation of 1.04 Å (Table 5). Pda8d (SEQ ID NO:2) and the design target correspond throughout their entire structures, including the turns connecting the secondary structure elements.

In conclusion, the experimental characterization of pda8d (SEQ ID NO:2) shows that it is folded and well-ordered with a weakly cooperative thermal transition, and that its structure is an excellent match to the design target. To our knowledge, pda8d (SEQ ID NO:2) is the shortest sequence of naturally occurring amino acids that folds to a unique structure without met al binding, oligomerization or disulfide bond formation (McKnight, et al., Nature Struc. Biol. 4:180 (1996)).

The successful design of pda8d (SEQ ID NO:2) supports the use of objective, quantitative sequence selection algorithms for protein design. This robustness suggests that the program can be used to design sequences for de novo backbones.

Example 4

Protein Design using a Scaled van der Waals Scoring Function in the Core Region An ideal model system to study core packing is the β1 immunoglobulin-binding domain of streptococcal protein G (Gβ1) (SEQ ID NO:38) (Gronenborn, et al., Science 253:657 (1991); Alexander, et al., Biochem. 31:3597 (1992); Barchi, et al., Protein Sci. 3:15 (1994); Gallagher, et al., 1994; Kuszewski, et al., 1994; Orban, et al., 1995). Its small size, 56 residues, renders computations and experiments tractable. Perhaps most critical for a core packing study, Gβ1 (SEQ ID NO:38) contains no disulfide bonds and does not require a cofactor or met al ion to fold. Further, Gβ1 (SEQ ID NO:38) contains sheet, helix and turn structures and is without the repetitive side-chain packing patterns found in coiled coils or some helical bundles. This lack of periodicity reduces the bias from a particular secondary or tertiary structure and necessitates the use of an objective side-chain selection program to examine packing effects.

Sequence positions that constitute the core were chosen by examining the side-chain solvent accessible surface area of Gβ1 (SEQ ID NO:38). Any side chain exposing less than 10% of its surface was considered buried. Eleven residues meet this criteria, with seven from the β sheet (positions 3, 5, 7, 20, 43, 52 and 54), three from the helix (positions 26, 30, and 34) and one in an irregular secondary structure (position 39). These positions form a contiguous core. The remainder of the protein structure, including all other side chains and the backbone, was used as the template for sequence selection calculations at the eleven core positions.

All possible core sequences consisting of alanine, valine, leucine, isoleucine, phenylalanine, tyrosine or tryptophan (A, V, L, I, F, Y or W) were considered. Our rotamer library was similar to that used by Desmet and coworkers (Desmet, et al., (1992) (supra)). Optimizing the sequence of the core of Gβ1 (SEQ ID NO:38) with 217 possible hydrophobic rotamers at all 11 positions results in $217^{11}$, or $5 \times 10^{25}$, rotamer sequences. Our scoring function consisted of two components: a van der Waals energy term and an atomic solvation term favoring burial of hydrophobic surface area. The van der Waals radii of all atoms in the simulation were scaled by a factor a (Eqn. 3) to change the importance of packing effects. Radii were not scaled for the buried surface area calculations. By predicting core sequences with various radii scalings and then experimentally characterizing the resulting proteins, a rigorous study of the importance of packing effects on protein design is possible.

The protein structure was modeled on the backbone coordinates of Gβ1 (SEQ ID NO:38), PDB record 1 pga (Bernstein, et al., supra; Gallagher, et al., 1994). Atoms of all side chains not optimized were left in their crystallographically determined positions. The program BIOGRAF (Molecular Simulations Incorporated, San Diego, Calif.) was used to generate explicit hydrogens on the structure which was then conjugate gradient minimized for 50 steps using the Dreiding forcefield (Mayo, et al., 1990, supra). The rotamer library, DEE optimization and Monte Carlo search was as outlined above. A Lennard-Jones 12–6 potential was used for van der Waals interactions, with atomic radii scaled for the various cases as discussed herein. The Richards definition of solvent-accessible surface area (Lee & Richards, supra) was used and areas were calculated with the Connolly algorithm (Connolly, (1983) (supra)). An atomic solvation parameter, derived from our previous work, of 23 cal/mol/Å² was used to favor hydrophobic burial and to penalize solvent exposure. To calculate side-chain nonpolar exposure in our optimization framework, we first consider the total hydrophobic area exposed by a rotamer in isolation. This exposure is decreased by the area buried in rotamer/template contacts, and the sum of the areas buried in pairwise rotamer/rotamer contacts.

Global optimum sequences for various values of the radius scaling factor a were found using the Dead-End Elimination theorem (Table 6) (SEQ ID NOS:38 to 49). Optimal sequences, and their corresponding proteins, are named by the radius scale factor used in their design. For example, the sequence designed with a radius scale factor of α=0.90 is called α90 (SEQ ID NO:43).

TABLE 6

| | | Gβ1 sequence | | | | | | | | | | |
|---|---|---|---|---|---|---|---|---|---|---|---|---|
| α | vol | TYR | LEU | LEU | ALA | ALA | PHE | ALA | VAL | TRP | PHE | VAL |
| | | 3 | 5 | 7 | 20 | 26 | 30 | 34 | 39 | 43 | 52 | 54 |
| 0.70 (SEQ ID NO: 39) | 1.28 | TRP | TYR | ILE | ILE | PHE | TRP | LEU | ILE | PHE | LEU | ILE |
| 0.75 (SEQ ID NO. 40) | 1.23 | PHE | ILE | PHE | ILE | VAL | TRP | VAL | LEU | \| | \| | ILE |
| 0.80 (SEQ ID NO: 41) | 1.13 | PHE | \| | ILE | \| | \| | \| | ILE | ILE | \| | TRP | ILE |
| 0.85 (SEQ ID NO: 42) | 1.15 | PHE | \| | ILE | \| | \| | \| | LEU | ILE | \| | TRP | PHE |
| 0.90 (SEQ ID NO: 43) | 1.01 | PHE | \| | ILE | \| | \| | \| | \| | ILE | \| | \| | \| |
| 0.95 (SEQ ID NO: 44) | 1.01 | PHE | \| | ILE | \| | \| | \| | \| | ILE | \| | \| | \| |
| 1.0 (SEQ ID NO: 45) | 0.99 | PHE | \| | VAL | \| | \| | \| | \| | ILE | \| | \| | \| |
| 1.05 (SEQ ID NO: 46) | 0.93 | PHE | \| | ALA | \| | \| | \| | \| | \| | \| | \| | \| |
| 1.075 (SEQ ID NO: 47) | 0.83 | ALA | ALA | ILE | \| | \| | ILE | \| | \| | \| | ILE | ILE |
| 1.10 (SEQ ID NO: 48) | 0.77 | ALA | \| | ALA | \| | \| | ALA | \| | \| | \| | ILE | ILE |
| 1.15 (SEQ ID NO: 49) | 0.68 | ALA | ALA | ALA | \| | \| | ALA | \| | \| | \| | LEU | \| |

In Table 6 (SEQ ID NOS: 38 to 49), the Gβ1 (SEQ ID NO:38) sequence and position numbers are shown at the top. vol is the fracton of core side-chain volume relative to the Gβ1 (SEQ ID NO:38) sequence. A vertical bar indicates identity with the Gβ1 (SEQ ID NO:38) sequence.

α100 (SEQ ID NO:45) was designed with α=1.0 and hence serves as a baseline for full incorporation of steric effects. The α100 (SEQ ID NO:45) sequence is very similar to the core sequence of Gβ1 (SEQ ID NO:38) (Table 6) even though no information about the naturally occurring sequence was used in the side-chain selection algorithm. Variation of α from 0.90 to 1.05 caused little change in the optimal sequence, demonstrating the algorithm's robustness to minor parameter perturbations. Further, the packing arrangements predicted with α=0.90–1.05 closely match Gβ1 (SEQ ID NO:38) with average X angle differences of only 4° from the crystal structure. The high identity and conformational similarity to Gβ1 (SEQ ID NO:38) imply that, when packing constraints are used, backbone conformation strongly determines a single family of well packed core designs. Nevertheless, the constraints on core packing were being modulated by α as demonstrated by Monte Carlo searches for other low energy sequences. Several alternate sequences and packing arrangements are in the twenty best sequences found by the Monte Carlo procedure when α=0.90. These alternate sequences score much worse when α=0.95, and when α=1.0 or 1.05 only strictly conservative packing geometries have low energies. Therefore, α=1.05 and α=0.90 define the high and low ends, respectively, of a range where packing specificity dominates sequence design.

For α<0.90, the role of packing is reduced enough to let the hydrophobic surface potential begin to dominate, thereby increasing the size of the residues selected for the core (Table 6) (SEQ ID NOS:38 to 49). A significant change in the optimal sequence appears between α=0.90 and 0.85 with both α85 (SEQ ID NO:42) and α80 (SEQ ID NO:41) containing three additional mutations relative to α90 (SEQ ID NO:43). Also, α85 (SEQ ID NO:42) and α80 (SEQ ID NO:41) have a 15% increase in total side-chain volume relative to Gβ1 (SEQ ID NO:38). As a drops below 0.80 an additional 10% increase in side-chain volume and numerous mutations occur, showing that packing constraints have been overwhelmed by the drive to bury nonpolar surface. Though the jumps in volume and shifts in packing arrangement appear to occur suddenly for the optimal sequences, examination of the suboptimal low energy sequences by Monte Carlo sampling demonstrates that the changes are not abrupt. For example, the α85 optimal sequence (SEQ ID NO:42) is the $11^{th}$ best sequence when α=0.90, and similarly, the α90 optimal sequence (SEQ ID NO:43) is the $9^{th}$ best sequence when α=0.85.

For α>1.05 atomic van der Waals repulsions are so severe that most amino acids cannot find any allowed packing arrangements, resulting in the selection of alanine for many positions. This stringency is likely an artifact of the large atomic radii and does not reflect increased packing specificity accurately. Rather, α=1.05 is the upper limit for the usable range of van der Waals scales within our modeling framework.

Experimental Characterization of Core Designs.

Variation of the van der Waals scale factor a results in four regimes of packing specificity: regime 1 where $0.9 \leq \alpha \leq 1.05$ and packing constraints dominate the sequence selection; regime 2 where $0.8 \leq \alpha < 0.9$ and the hydrophobic solvation potential begins to compete with packing forces; regime 3 where α<0.8 and hydrophobic solvation dominates the design; and, regime 4 where α>1.05 and van der Waals repulsions appear to be too severe to allow meaningful sequence selection. Sequences that are optimal designs were selected from each of the regimes for synthesis and characterization. They are α90 (SEQ ID NO:43) from regime 1, α85 (SEQ ID NO: 42) from regime 2, α70 (SEQ ID NO:39) from regime 3 and α107 (SEQ ID NO:47) from regime 4. For each of these sequences, the calculated amino acid identities of the eleven core positions are shown in Table 6; the remainder of the protein sequence matches Gβ1 (SEQ ID NO:38). The goal was to study the relation between the degree of packing specificity used in the core design and the extent of native-like character in the resulting proteins.

Peptide Synthesis and Purification.

With the exception of the eleven core positions designed by the sequence selection algorithm, the sequences synthesized match Protein Data Bank entry 1 pga. Peptides were synthesized using standard Fmoc chemistry, and were purified by reverse-phase HPLC. Matrix assisted laser desorption mass spectrometry found all molecular weights to be within one unit of the expected masses.

CD and Fluorescence Spectroscopy and Size Exclusion Chromatography.

The solution conditions for all experiments were 50 mM sodium phosphate buffer at pH 5.5 and 25° C. unless noted. Circular dichroism spectra were acquired on an Aviv 62DS spectrometer equipped with a thermoelectric unit. Peptide concentration was approximately 20 μM. Thermal melts were monitored at 218 nm using 2° increments with an equilibration time of 120 s. $T_m$'s were defined as the maxima of the derivative of the melting curve. Reversibility for each of the proteins was confirmed by comparing room temperature CD spectra from before and after heating. Guanidinium chloride denaturation measurements followed published methods (Pace, Methods. Enzymol. 131:266 (1986)). Protein concentrations were determined by UV spectrophotometry. Fluorescence experiments were performed on a Hitachi F-4500 in a 1 cm pathlength cell. Both peptide and ANS concentrations were 50 μM. The excitation wavelength was 370 nm and emission was monitored from 400 to 600 nm. Size exclusion chromatography was performed with a PolyLC hydroxyethyl A column at pH 5.5 in 50 mM sodium phosphate at 0° C. Ribonuclease A, carbonic anhydrase and Gβ1 (SEQ ID NO:38) were used as molecular weight standards. Peptide concentrations during the separation were ~15 μM as estimated from peak heights monitored at 275 nm.

Nuclear Magnetic Resonance Spectroscopy.

Samples were prepared in 90/10 $H_2O/D_2O$ and 50 mM sodium phosphate buffer at pH 5.5. Spectra were acquired on a Varian Unityplus 600 MHz spectrometer at 25° C. Samples were approximately 1 mM, except for α70 (SEQ ID NO:39) which had limited solubility (100 μM). For hydrogen exchange studies, an NMR sample was prepared, the pH was adjusted to 5.5 and a spectrum was acquired to serve as an unexchanged reference. This sample was lyophilized, reconstituted in $D_2O$ and repetitive acquisition of spectra was begun immediately at a rate of 75 s per spectrum. Data acquisition continued for ~20 hours, then the sample was heated to 99° C. for three minutes to fully exchange all protons. After cooling to 25° C., a final spectrum was acquired to serve as the fully exchanged reference. The areas of all exchangeable amide peaks were normalized by a set of non-exchanging aliphatic peaks. pH values, uncorrected for isotope effects, were measured for all the samples after data acquisition and the time axis was normalized to correct for minor differences in pH (Rohl, et al., Biochem. 31:1263 (1992)).

α90 (SEQ ID NO:43) and α85 (SEQ ID NO:42) have ellipticities and spectra very similar to Gβ1 (SEQ ID NO:38) (not shown), suggesting that their secondary structure content is comparable to that of Gβ1 (SEQ ID NO:38) (FIG. 10). Conversely, α70 (SEQ ID NO:39) has much weaker ellipticity and a perturbed spectrum, implying a loss of secondary structure relative to Gβ1 (SEQ ID NO:38). α107 (SEQ ID NO:47) has a spectrum characteristic of a random coil. Thermal melts monitored by CD are shown in FIG. 10B. α85 (SEQ ID NO:42) and α90 (SEQ ID NO:43) both have cooperative transitions with melting temperatures ($T_m$'s) of 83° C. and 92° C., respectively. α107 (SEQ ID NO:47) shows no thermal transition, behavior expected from a fully unfolded polypeptide, and α70 (SEQ ID NO: 39) has a broad, shallow transition, centered at ~40° C., characteristic of partially folded structures. Relative to Gβ1 (SEQ ID NO:38), which has a $T_m$ of 87° C. (Alexander, et al., supra), α85 (SEQ ID NO:42) is slightly less thermostable and α90 (SEQ ID NO:43) is more stable. Chemical denaturation measurements of the free energy of unfolding ($\Delta G_u$) at 25° C. match the trend in $T_m$'s.

α90 (SEQ ID NO:43) has a larger $\Delta G_u$ than that reported for Gβ1 (SEQ ID NO:38) (Alexander, et al., supra) while α85 (SEQ ID NO:42) is slightly less stable. It was not possible to measure $\Delta G_u$ for α70 (SEQ ID NO:39) or α107 (SEQ ID NO:47) because they lack discernible transitions.

The extent of chemical shift dispersion in the proton NMR spectrum of each protein was assessed to gauge each protein's degree of native-like character (data not shown). α90 (SEQ ID NO:43) possesses a highly dispersed spectrum, the hallmark of a well-ordered native protein. α85 (SEQ ID NO:42) has diminished chemical shift dispersion and peaks that are somewhat broadened relative to α90 (SEQ ID NO:43), suggesting a moderately mobile structure that nevertheless maintains a distinct fold. α70's (SEQ ID NO:39) NMR spectrum has almost no dispersion. The broad peaks are indicative of a collapsed but disordered and fluctuating structure. α107 (SEQ ID NO:47) has a spectrum with sharp lines and no dispersion, which is indicative of an unfolded protein.

Amide hydrogen exchange kinetics are consistent with the conclusions reached from examination of the proton NMR spectra. Measuring the average number of unexchanged amide protons as a function of time for each of the designed proteins results as follows (data not shown): α90 (SEQ ID NO:43) protects ~13 protons for over 20 hours of exchange at pH 5.5 and 25° C. The α90 (SEQ ID NO: 43) exchange curve is indistinguishable from Gβ1's (SEQ ID NO:38) (not shown). α85 (SEQ ID NO:42) also maintains a well-protected set of amide protons, a distinctive feature of ordered native-like proteins. The number of protected protons, however, is only about half that of α90 (SEQ ID NO:43). The difference is likely due to higher flexibility in some parts of the α85 (SEQ ID NO:42) structure. In contrast, α70 (SEQ ID NO:39) and α107 (SEQ ID NO:47) were fully exchanged within the three minute dead time of the experiment, indicating highly dynamic structures.

Near UV CD spectra and the extent of 8-anilino-1-naphthalene sulfonic acid (ANS) binding were used to assess the structural ordering of the proteins. The near UV Cβ spectra of α85 (SEQ ID NO:42) and α90 (SEQ ID NO:43) have strong peaks as expected for proteins with aromatic residues fixed in a unique tertiary structure while α70 (SEQ ID NO:39) and α107 (SEQ ID NO:47) have featureless spectra indicative of proteins with mobile aromatic residues, such as non-native collapsed states or unfolded proteins. α70 (SEQ ID NO:39) also binds ANS well, as indicated by a three-fold intensity increase and blue shift of the ANS emission spectrum. This strong binding suggests that α70 (SEQ ID NO:39) possesses a loosely packed or partially exposured cluster of hydrophobic residues accessible to ANS. ANS binds α85 (SEQ ID NO:42) weakly, with only a 25% increase in emission intensity, similar to the association seen for some native proteins (Semisotnov, et al., Biopolymers 31:119(1991)). α90 (SEQ ID NO:43) and α107 (SEQ ID NO:47) cause no change in ANS fluorescence. All of the proteins migrated as monomers during size exclusion chromatography.

In summary, α90 (SEQ ID NO:43) is a well-packed native-like protein by all criteria, and it is more stable than the naturally occurring Gβ1 (SEQ ID NO:38) sequence, possibly because of increased hydrophobic surface burial. α85 (SEQ ID NO:42) is also a stable, ordered protein, albeit with greater motional flexibility than α90 (SEQ ID NO:43), as evidenced by its NMR spectrum and hydrogen exchange behavior. α70 (SEQ ID NO:39) has all the features of a disordered collapsed globule: a non-cooperative thermal transition, no NMR spectral dispersion or amide proton protection, reduced secondary structure content and strong ANS binding. α107 (SEQ ID NO:47) is a completely unfolded chain, likely due to its lack of large hydrophobic residues to hold the core together. The clear trend is a loss of protein ordering as α decreases below 0.90.

The different packing regimes for protein design can be evaluated in light of the experimental data. In regime 1, with $0.9 \leq \alpha \leq 1.05$, the design is dominated by packing specificity resulting in well-ordered proteins. In regime 2, with $0.8 \leq \alpha < 0.9$, packing forces are weakened enough to let the hydrophobic force drive larger residues into the core which produces a stable well-packed protein with somewhat increased structural motion. In regime 3, α<0.8, packing forces are reduced to such an extent that the hydrophobic force dominates, resulting in a fluctuating, partially folded structure with no stable core packing. In regime 4, α>1.05, the steric forces used to implement packing specificity are scaled too high to allow reasonable sequence selection and hence produce an unfolded protein. These results indicate that effective protein design requires a consideration of packing effects. Within the context of a protein design algorithm, we have quantitatively defined the range of packing forces necessary for successful designs. Also, we have demonstrated that reduced specificity can be used to design protein cores with alternative packings.

To take advantage of the benefits of reduced packing constraints, protein cores should be designed with the smallest α that still results in structurally ordered proteins. The optimal protein sequence from regime 2, α85 (SEQ ID NO:42), is stable and well packed, suggesting $0.8 \leq \alpha < 0.9$ as a good range. NMR spectra and hydrogen exchange kinetics, however, clearly show that α85 (SEQ ID NO:42) is not as structurally ordered as α90 (SEQ ID NO:43). The packing arrangements predicted by our program for W43 in α85 (SEQ ID NO:42) and α90 (SEQ ID NO:43) present a possible explanation. For α90 (SEQ ID NO:43), W43 is predicted to pack in the core with the same conformation as in the crystal structure of Gβ1 (SEQ ID NO:38). In α85 (SEQ ID NO:42), the larger side chains at positions 34 and 54, leucine and phenylalanine respectively, compared to alanine and valine in α90 (SEQ ID NO:43), force W43 to expose 91 $Å^2$ of nonpolar surface compared to 19 $Å^2$ in α90 (SEQ ID NO:43). The hydrophobic driving force this exposure represents seems likely to stabilize alternate conformations that bury W43 and thereby could contribute to α85's (SEQ ID NO:42) conformational flexibility (Dill, 1985; Onuchic, et al., 1996). In contrast to the other core positions, a residue at position 43 can be mostly exposed or mostly buried depending on its side-chain conformation. We designate positions with this characteristic as boundary positions, which pose a difficult problem for protein design because of their potential to either strongly interact with the protein's core or with solvent.

A scoring function that penalizes the exposure of hydrophobic surface area might assist in the design of boundary residues. Dill and coworkers used an exposure penalty to improve protein designs in a theoretical study (Sun, et al., Protein Eng. 8(12)1205–1213 (1995)).

A nonpolar exposure penalty would favor packing arrangements that either bury large side chains in the core or replace the exposed amino acid with a smaller or more polar one. We implemented a side-chain nonpolar exposure penalty in our optimization framework and used a penalizing solvation parameter with the same magnitude as the hydrophobic burial parameter.

The results of adding a hydrophobic surface exposure penalty to our scoring function are shown in Table 7 (SEQ ID NOS:50 to 64).

TABLE 7

| | | | | | | | α = 0.85 | | | | | |
|---|---|---|---|---|---|---|---|---|---|---|---|---|
| # | $A_{np}$ | TYR | LEU | LEU | ALA | ALA | PHE | ALA | VAL | TRP | PHE | VAL |
| | | 3 | 5 | 7 | 20 | 26 | 30 | 34 | 39 | 43 | 52 | 54 |
| 1 (SEQ ID NO: 50) | 109 | PHE | \| | ILE | \| | \| | \| | LEU | ILE | \| | TRP | PHE |
| 2 (SEQ ID NO: 51) | 109 | \| | \| | ILE | \| | \| | \| | LEU | ILE | \| | TRP | PHE |
| 3 (SEQ ID NO: 62) | 104 | PHE | \| | ILE | \| | \| | \| | LEU | ILE | \| | \| | PHE |
| 4 (SEQ ID NO: 53) | 104 | \| | \| | ILE | \| | \| | \| | LEU | ILE | \| | \| | PHE |
| 5 (SEQ ID NO: 54) | 108 | PHE | \| | ILE | \| | \| | \| | LEU | \| | \| | TRP | PHE |
| 6 (SEQ ID NO: 55) | 62 | PHE | \| | ILE | \| | \| | \| | LEU | ILE | VAL | TRP | PHE |
| 7 (SEQ ID NO: 56) | 103 | PHE | \| | ILE | \| | \| | \| | LEU | ILE | \| | TYR | PHE |
| 8 (SEQ ID NO: 57) | 109 | PHE | \| | VAL | \| | \| | \| | LEU | ILE | \| | TRP | PHE |
| 9 (SEQ ID NO: 58) | 30 | PHE | \| | ILE | \| | \| | \| | \| | ILE | \| | \| | \| |
| 10 (SEQ ID NO: 59) | 38 | PHE | \| | ILE | \| | \| | \| | \| | ILE | \| | TRP | \| |
| 11 (SEQ ID NO: 60) | 108 | \| | \| | ILE | \| | \| | \| | LEU | \| | \| | TRP | PHE |
| 12 (SEQ ID NO 61) | 62 | \| | \| | ILE | \| | \| | \| | LEU | ILE | VAL | TRP | PHE |
| 13 (SEQ ID NO: 62) | 109 | PHE | \| | ILE | \| | \| | TYR | LEU | ILE | \| | TRP | PHE |
| 14 (SEQ ID NO. 63) | 103 | \| | \| | ILE | \| | \| | \| | LEU | ILE | \| | TYR | PHE |

TABLE 7-continued

| | | | | | α = 0.85 | | | | | | |
|---|---|---|---|---|---|---|---|---|---|---|---|
| # | $A_{np}$ | TYR | LEU | LEU | ALA | ALA | PHE | ALA | VAL | TRP | PHE | VAL |
| 15 (SEQ ID NO: 64) | 109 | | | VAL | | | | LEU | ILE | | TRP | PHE |

Table 7 (SEQ ID NOS:50 to 64) depicts the 15 best sequences for the core positions of Gβ1 (SEQ ID NO:38) using α=0.85 without an exposure penalty. Anp is the exposed nonpolar surface area in Å².

When α=0.85 the nonpolar exposure penalty dramatically alters the ordering of low energy sequences. The α85 (SEQ ID NO:42) sequence, the former ground state, drops to 7$^{th}$ and the rest of the 15 best sequences expose far less hydrophobic area because they bury W43 in a conformation similar to α90 (SEQ ID NO:43) (model not shown). The exceptions are the 8$^{th}$ (SEQ ID NO:57) and 14$^{th}$ (SEQ ID NO:63) sequences, which reduce the size of the exposed boundary residue by replacing W43 with an isoleucine, and the 13$^{th}$ best sequence (SEQ ID NO:62) which replaces W43 with a valine. The new ground state sequence is very similar to α90 (SEQ ID NO:43), with a single valine to isoleucine mutation, and should share α90's (SEQ ID NO:43) stability and structural order. In contrast, when α=0.90, the optimal sequence does not change and the next 14 best sequences (SEQ ID NO:63), found by Monte Carlo sampling, change very little. This minor effect is not surprising, since steric forces still dominate for α=0.90 and most of these sequences expose very little surface area. Burying W43 restricts sequence selection in the core somewhat, but the reduced packing forces for α=0.85 still produce more sequence variety than α=0.90. The exposure penalty complements the use of reduced packing specificity by limiting the gross overpacking and solvent exposure that occurs when the core's boundary is disrupted. Adding this constraint should allow lower packing forces to be used in protein design, resulting in a broader range of high-scoring sequences and reduced bias from fixed backbone and discrete rotamers.

To examine the effect of substituting a smaller residue at a boundary position, we synthesized and characterized the 13$^{th}$ best sequence of the α=0.85 optimization with exposure penalty (Table 8) (SEQ ID NOS:65 to 79).

TABLE 8

| | | | | | α = 0.85 exposure penalty | | | | | | |
|---|---|---|---|---|---|---|---|---|---|---|---|
| # | $A_{np}$ | TYR | LEU | LEU | ALA | ALA | PHE | ALA | VAL | TRP | PHE | VAL |
| | | 3 | 5 | 7 | 20 | 2B | 30 | 34 | 39 | 43 | 52 | 54 |
| 1 (SEQ ID NO: 65) | 30 | PHE | | ILE | | | | | ILE | | | ILE |
| 2 (SEQ ID NO: 66) | 29 | PHE | | ILE | | | | ILE | ILE | | | |
| 3 (SEQ Io NO: 67) | 29 | PHE | ILE | PHE | | | | | ILE | | | |
| 4 (SEQ ID NO: 68) | 30 | | | ILE | | | | | ILE | | | ILE |
| 5 (SEQ ID 69) | 29 | | | ILE | | | | ILE | ILE | | | |
| 6 (SEQ ID NO. 70) | 29 | | ILE | PHE | | | | | ILE | | | |
| 7 (SEQ ID NO: 71) | 109 | PHE | | ILE | | | | LEU | ILE | | TRP | PHE |

TABLE 8-continued

α = 0.85 exposure penalty

| # | $A_{np}$ | TYR | LEU | LEU | ALA | ALA | PHE | ALA | VAL | TRP | PHE | VAL |
|---|---|---|---|---|---|---|---|---|---|---|---|---|
| 8 (SEQ ID NO: 72) | 52 | PHE | \| | ILE | \| | \| | \| | LEU | ILE | ILE | \| | PHE |
| 9 (SEQ ID NO: 73) | 29 | \| | \| | ILE | \| | \| | \| | \| | ILE | \| | \| | \| |
| 10 (SEQ ID NO: 74) | 29 | PHE | \| | ILE | \| | \| | \| | \| | ILE | \| | \| | \| |
| 11 (SEQ ID NO: 75) | 109 | \| | \| | ILE | \| | \| | \| | LEU | ILE | \| | TRP | PHE |
| 12 (SEQ ID NO: 76) | 38 | PHE | \| | ILE | \| | \| | \| | \| | ILE | \| | TRP | ILE |
| 13 (SEQ ID NO. 77) | 62 | PHE | \| | ILE | \| | \| | \| | LEU | ILE | VAL | TRP | PHE |
| 14 (SEQ ID NO: 78) | 52 | \| | \| | ILE | \| | \| | \| | LEU | ILE | ILE | \| | PHE |
| 15 (SEQ ID NO: 79) | 30 | PHE | \| | ILE | \| | \| | \| | \| | ILE | \| | TYR | ILE |

Table 8 (SEQ ID NOS:65 to 79) depicts the 15 best sequences of the core positions of Gβ1 (SEQ ID NO:38) using α=0.85 with an exposure penalty. $A_{np}$ is the exposed nonpolar surface area in Å².

This sequence, α85W43V, replaces W43 with a valine but is otherwise identical to α85 (SEQ ID NO: 42). Though the 8$^{th}$ (SEQ ID NO:72) and 14$^{th}$ (SEQ ID NO:78) sequences also have a smaller side chain at position 43, additional changes in their sequences relative to α85 (SEQ ID NO:42) would complicate interpretation of the effect of the boundary position change. Also, α85W43V has a significantly different packing arrangement compared to Gβ1 (SEQ ID NO:38), with 7 out of 11 positions altered, but only an 8% increase in side-chain volume. Hence, α85W43V is a test of the tolerance of this fold to a different, but nearly volume conserving, core. The far UV CD spectrum of α85W43V is very similar to that of Gβ1 (SEQ ID NO:38) with an ellipticity at 218 nm of −14000 deg cm²/dmol. While the secondary structure content of α85W43V is native-like, its $T_m$ is 65° C., nearly 20° C. lower than α85 (SEQ ID NO:42). In contrast to α85W43V's decreased stability, its NMR spectrum has greater chemical shift dispersion than α85 (SEQ ID NO:42) (data not shown). The amide hydrogen exchange kinetics show a well protected set of about four protons after 20 hours (data not shown). This faster exchange relative to α85 (SEQ ID NO:42) is explained by α85W43V's significantly lower stability (Mayo & Baldwin, 1993). α85W43V appears to have improved structural specificity at the expense of stability, a phenomenon observed previously in coiled coils (Harbury, et al., 1993). By using an exposure penalty, the design algorithm produced a protein with greater native-like character.

We have quantitatively defined the role of packing specificity in protein design and have provided practical bounds for the role of steric forces in our protein design program. This study differs from previous work because of the use of an objective, quantitative program to vary packing forces during design, which allows us to readily apply our conclusions to different protein systems. Further, by using the minimum effective level of steric forces, we were able to design a wider variety of packing arrangements that were compatible with the given fold. Finally, we have identified a difficulty in the design of side chains that lie at the boundary between the core and the surface of a protein, and we have implemented a nonpolar surface exposure penalty in our sequence design scoring function that addresses this problem.

Example 5

Design of a Full Protein

The entire amino acid sequence of a protein motif has been computed. As in Example 4, the second zinc finger module of the DNA binding protein Zif268 (SEQ ID NO:1)

was selected as the design template. In order to assign the residue positions in the template structure into core, surface or boundary classes, the orientation of the Cα–Cβ vectors was assessed relative to a solvent accessible surface computed using only the template Cα atoms. A solvent accessible surface for only the Cα atoms of the target fold was generated using the Connolly algorithm with a probe radius of 8.0 Å, a dot density of 10 Å$^2$, and a Cα radius of 1.95 Å. A residue was classified as a core position if the distance from its Cα, along its Cα–Cβ vector, to the solvent accessible surface was greater than 5 Å, and if the distance from its Cβ to the nearest surface point was greater than 2.0 Å. The remaining residues were classified as surface positions if the sum of the distances from their Cα, along their Cα–Cβ vector, to the solvent accessible surface plus the distance from their Cβ to the nearest surface point was less than 2.7 Å. All remaining residues were classified as boundary positions. The classifications for Zif268 (SEQ ID NO:1) were used as computed except that positions 1, 17 and 23 were converted from the boundary to the surface class to account for end effects from the proximity of chain termini to these residues in the teriary structure and inaccuracies in the assignment.

The small size of this motif limits to one (position 5) the number of residues that can be assigned unambiguously to the core while seven residues (positions 3, 7, 12, 18, 21, 22, and 25) were classified as boundary and the remaining 20 residues were assigned to the surface. Interestingly, while three of the zinc binding positions of Zif268 (SEQ ID NO:1) are in the boundary or core, one residue, position 8, has a Cα–Cβ vector directed away from the protein's geometric center and is classified as a surface position. As in our previous studies, the amino acids considered at the core positions during sequence selection were A, V, L, I, F, Y, and W; the amino acids considered at the surface positions were A, S, T, H, D, N, E, Q, K, and R; and the combined core and surface amino acid sets (16 amino acids) were considered at the boundary positions. Two of the residue positions (9 and 27) have φ angles greater than 0° and are set to Gly by the sequence selection algorithm to minimize backbone strain.

The total number of amino acid sequences that must be considered by the design algorithm is the product of the number of possible amino acid types at each residue position. The ββα motif residue classification described above results in a virtual combinatorial library of $1.9 \times 10^{27}$ possible amino acid sequences (one core position with 7 possible amino acids, 7 boundary positions with 16 possible amino acids, 18 surface positions with 10 possible amino acids and 2 positions with φ angles greater than 0° each with 1 possible amino acid). A corresponding peptide library consisting of only a single molecule for each 28 residue sequence would have a mass of 11.6 metric tons. In order to accurately model the geometric specificity of side-chain placement, we explicitly consider the torsional flexibility of amino acid side chains in our sequence scoring by representing each amino acid with a discrete set of allowed conformations, called rotamers. As above, a backbone dependent rotamer library was used (Dunbrack and Karplus, supra), with adjustments in the $X_1$ and $X_2$ angles of hydrophobic residues. As a result, the design algorithm must consider all rotamers for each possible amino acid at each residue position. The total size of the search space for the ββα motif is therefore $1.1 \times 10^{62}$ possible rotamer sequences. The rotamer optimization problem for the ββα motif required 90 CPU hours to find the optimal sequence.

The optimal sequence, shown in FIG. 11, is called Full Sequence Design-1 (FSD-1) (SEQ ID NO:3). Even though all of the hydrophilic amino acids were considered at each of the boundary positions, the algorithm selected only nonpolar amino acids. The eight core and boundary positions are predicted to form a well-packed buried cluster. The Phe side chains selected by the algorithm at the zinc binding His positions of Zif268 (SEQ ID NO:1), positions 21 and 25, are over 80% buried and the Ala at position 5 is 100% buried while the Lys at position 8 is greater than 60% exposed to solvent. The other boundary positions demonstrate the strong steric constraints on buried residues by packing similar side chains in an arrangement similar to that of Zif268 (SEQ ID NO:1). The calculated optimal configuration for core and boundary residues buries ~1150 Å$^2$ of nonpolar surface area. On the helix surface, the program positions Asn 14 as a helix N-cap with a hydrogen bond between its side-chain carbonyl oxygen and the backbone amide proton of residue 16. The eight charged residues on the helix form three pairs of hydrogen bonds, though in our coiled coil designs helical surface hydrogen bonds appeared to be less important than the overall helix propensity of the sequence (Dahiyat, et al., Science (1997)). Positions 4 and 11 on the exposed sheet surface were selected to be Thr, one of the best β-sheet forming residues (Kim, et al., 1993).

FIG. 11 (SEQ ID NOS:3 to 22) shows the alignment of the sequences for FSD-1 (SEQ ID NO:3) and Zif268 (SEQ ID NO:1). Only 6 of the 28 residues (21%) are identical and only 11 (39%) are similar. Four of the identities are in the buried cluster, which is consistent with the expectation that buried residues are more conserved than solvent exposed residues for a given motif (Bowie, et al., Science 247:1306–1310 (1990)). A BLAST (Altschul, et al., supra) search of the FSD-1 sequence (SEQ ID NO:3) against the non-redundant protein sequence database of the National Center for Biotechnology Information did not find any zinc finger protein sequences. Further, the BLAST search found only low identity matches of weak statistical significance to fragments of various unrelated proteins. The highest identity matches were 10 residues (36%) with p values ranging from 0.63–1.0. Random 28 residue sequences that consist of amino acids allowed in the ββα position classification described above produced similar BLAST search results, with 10 or 11 residue identities (36–39%) and p values ranging from 0.35–1.0, further suggesting that the matches found for FSD-1 are statistically insignificant. The very low identity to any known protein sequence demonstrates the novelty of the FSD-1 sequence (SEQ ID NO:3) and underscores that no sequence information from any protein motif was used in our sequence scoring function.

In order to examine the robustness of the computed sequence, the sequence of FSD-1 (SEQ ID NO:3) was used as the starting point of a Monte Carlo simulated annealing run. The Monte Carlo search finds high scoring, suboptimal sequences in the neighborhood of the optimal solution (Dahiyat, et al., (1996) (supra)). The energy spread from the ground-state solution to the 1000$^{th}$ most stable sequence is about 5 kcal/mol indicating that the density of states is high. The amino acids comprising the core of the molecule, with the exception of position 7, are essentially invariant (FIG. 11) (SEQ ID NOS:4 to 22). Almost all of the sequence variation occurs at surface positions, and typically involves conservative changes. Asn 14, which is predicted to form a helix N-cap, is among the most conserved surface positions. The strong sequence conservation observed for critical areas of the molecule suggests that if a representative sequence folds into the design target structure, then perhaps thousands of sequences whose variations do not disrupt the critical interactions may be equally competent. Even if billions of sequences would successfully achieve the target fold, they would represent only a vanishingly small proportion of the $10^{27}$ possible sequences.

Experimental Validation.

FSD-1 (SEQ ID NO:3) was synthesized in order to characterize its structure and assess the performance of the design algorithm. The far UV circular dichroism (CD) spectrum of FSD-1 (SEQ ID NO:3) shows minima at 220 nm and 207 nm, which is indicative of a folded structure (data not shown). The thermal melt is weakly cooperative, with an inflection point at 39° C., and is completely reversible (data not shown). The broad melt is consistent with a low enthalpy of folding which is expected for a motif with a small hydrophobic core. This behavior contrasts the uncooperative thermal unfolding transitions observed for other folded short peptides (Scholtz, et al., 1991). FSD-1 (SEQ ID NO:3) is highly soluble (greater than 3 mM) and equilibrium sedimentation studies at 100 μM, 500 μM and 1 mM show the protein to be monomeric. The sedimentation data fit well to a single species, monomer model with a molecular mass of 3630 at 1 mM, in good agreement with the calculated monomer mass of 3488. Also, far UV CD spectra showed no concentration dependence from 50 μM to 2 mM, and nuclear magnetic resonance (NMR) COSY spectra taken at 100 μM and 2 mM were essentially identical.

The solution structure of FSD-1 (SEQ ID NO:3) was solved using homonuclear 2D $^1$H NMR spectroscopy (Piantini, et al., 1982). NMR spectra were well dispersed indicating an ordered protein structure and easing resonance assignments. Proton chemical shift assignments were determined with standard homonuclear methods (Wuthrich, 1986). Unambiguous sequential and short-range NOEs indicate helical secondary structure from residues 15 to 26 in agreement with the design target.

The structure of FSD-1 (SEQ ID NO:3) was determined using 284 experimental restraints (10.1 restraints per residue) that were non-redundant with covalent structure including 274 NOE distance restraints and 10 hydrogen bond restraints involving slowly exchanging amide protons. Structure calculations were performed using X-PLOR (Brunger, 1992) with standard protocols for hybrid distance geometry-simulated annealing (Nilges, et al., FEBS Lett. 229:317 (1988)). An ensemble of 41 structures converged with good covalent geometry and no distance restraint violations greater than 0.3 Å (Table 9).

TABLE 9

NMR structure determination: distance restraints, structural statistics and atomic root-mean-square (rms) deviations. <SA> are the 41 simulated annealing structures, SA is the average structure before energy minimization, $(SA)_r$ is the restrained energy minimized average structure, and SD is the standard deviation.

| Distance restraints | |
|---|---|
| Intraresidue | 97 |
| Sequential | 83 |
| Short range (\|i–j\| = 2–5 residues) | 59 |
| Long range (\|i–j\| > 5 residues) | 35 |
| Hydrogen bond | 10 |
| Total | 284 |

| Structural statistics | | |
|---|---|---|
| | <SA> ± SD | $(SA)_r$ |
| Rms deviation from | 0.043 ± 0.003 | 0.038 |

TABLE 9-continued

NMR structure determination: distance restraints, structural statistics and atomic root-mean-square (rms) deviations. <SA> are the 41 simulated annealing structures, SA is the average structure before energy minimization, $(SA)_r$ is the restrained energy minimized average structure, and SD is the standard deviation.

| distance restraints (Å) | | |
|---|---|---|
| Rms deviation from idealized geometry | | |
| Bonds (Å) | 0.0041 ± 0.0002 | 0.0037 |
| Angles (degrees) | 0.67 ± 0.02 | 0.65 |
| Impropers (degrees) | 0.53 ± 0.05 | 0.51 |

| Atomic rms deviations (Å)* | | |
|---|---|---|
| | <SA> vs. SA ± SD | <SA> vs. $(SA)_r$ ± SD |
| Backbone | 0.54 ± 0.15 | 0.69 ± 0.16 |
| Backbone + nonpolar side chains† | 0.99 ± 0.17 | 1.16 ± 0.18 |
| Heavy atoms | 1.43 ± 0.20 | 1.90 ± 0.29 |

*Atomic rms deviations are for residues 3 to 26, inclusive. Residues 1, 2, 27 and 28 were disordered (φ, ψ angular order parameters (34) < 0.78) and had only sequential and |i–j| = 2 NOEs. †Nonpolar side chains are from residues 3, 5, 7, 12, 18, 21, 22, and 25 which consitute the core of the protein.

The backbone of FSD-1 (SEQ ID NO:3) is well defined with a root-mean-square (rms) deviation from the mean of 0.54 Å (residues 3–26). Considering the buried side chains (residues 3, 5, 7, 12, 18, 21, 22, and 25) in addition to the backbone gives an rms deviation of 0.99 Å, indicating that the core of the molecule is well ordered. The stereochemical quality of the ensemble of structures was examined using PROCHECK (Laskowski, et al., J. Appl. Crystallogr. 26:283 (1993)). Not including the disordered termini and the glycine residues, 87% of the residues fall in the most favored region and the remainder in the allowed region of φ, ψ space. Modest heterogeneity is present in the first strand (residues 3–6) which has an average backbone angular order parameter (Hyberts, et al., 1992) of <S>=0.96±0.04 compared to the second strand (residues 9–12) with an <S>=0.98±0.02 and the helix (residues 15–26) with an <S>=0.99±0.01. Overall, FSD-1 is notably well ordered and, to our knowledge, is the shortest sequence consisting entirely of naturally occurring amino acids that folds to a unique structure without met al binding, oligomerization or disulfide bond formation (McKnight, et al., 1997).

The packing pattern of the hydrophobic core of the NMR structure ensemble of FSD-1 (SEQ ID NO:3) (Tyr 3, Iie 7, Phe 12, Leu 18, Phe 21, Ile 22, and Phe 25) is similar to the computed packing arrangement. Five of the seven residues have $X_1$ angles in the same gauche$^+$, gauche$^-$ or trans category as the design target, and three residues match both $X_1$ and $X_2$ angles. The two residues that do not match their computed $X_1$ angles are Ile 7 and Phe 25, which is consistent with their location at the less constrained, open end of the molecule. Ala 5 is not involved in its expected extensive packing interactions and instead exposes about 45% of its surface area because of the displacement of the strand 1 backbone relative to the design template. Conversely, Lys 8 behaves as predicted by the algorithm with its solvent exposure (60%) and $X_1$ and $X_2$ angles matching the computed structure. Most of the solvent exposed residues are disordered which precludes examination of the predicted surface residue hydrogen bonds. Asn 14, however, forms a helix N-cap from its sidechain carbonyl oxygen as predicted, but to the amide of Glu 17, not Lys 16 as expected from the design. This hydrogen bond is present in 95% of the structure ensemble and has a donor-acceptor distance of 2.6±0.06 Å. In general, the side chains of FSD-1 (SEQ ID NO:3) correspond well with the design program predictions.

A comparison of the average restrained minimized structure of FSD-1 (SEQ ID NO:3) and the design target was done (data not shown). The overall backbone rms deviation of FSD-1 (SEQ ID NO:3) from the design target is 1.98 Å for residues 3–26 and only 0.98 Å for residues 8–26 (Table 10).

TABLE 10

Comparison of the FSD-1 (SEQ ID NO:3) experimentally determined structure and the design target structure. The FSD-1 (SEQ ID NO:3) structure is the restrained energy minimized average from the NMR structure determination. The design target structure is the second DNA binding module of the zinc finger Zif268 (9) (SEQ ID NO:1).

Atomic rms deviations (Å)

| | |
|---|---|
| Backbone, residues 3–26 | 1.98 |
| Backbone, residues 8–26 | 0.98 |

Super-secondary structure parameters*

| | FSD-1 | Design Target |
|---|---|---|
| h(Å) | 9.9 | 8.9 |
| θ(degrees) | 14.2 | 16.5 |
| Ω(degrees) | 13.1 | 13.5 |

*h, θ, Ω are calculated as previously described (36, 37). h is the distance between the centroid of the helix Cα coordinates (residues 15–26) and the least-square plane fit to the Cα coordinates of the sheet (residues 3–12. θ is the angle of inclination of the principal moment of the helix Cα atoms with the plane of the sheet. Ω is the angle between the projection of the principal moment of the helix onto the sheet and the projection of the average least-square fit line to the strand Cα coordinates (residues 3–6 and 9–12) onto the sheet.

The largest difference between FSD-1 (SEQ ID NO:3) and the target structure occurs from residues 4–7, with a displacement of 3.0–3.5 Å of the backbone atom positions of strand 1. The agreement for strand 2, the strand to helix turn, and the helix is remarkable, with the differences nearly within the accuracy of the structure determination. For this region of the structure, the rms difference of $\phi$, $\psi$ angles between FSD-1 (SEQ ID NO:3) and the design target is only 14±9°. In order to quantitatively assess the similarity of FSD-1 (SEQ ID NO:3) to the global fold of the target, we calculated their supersecondary structure parameters (Table 9) (Janin & Chothia, J. Mol. Biol. 143:95 (1980); Su & Mayo, Protein Sci. in press, 1997), which describe the relative orientations of secondary structure units in proteins. The values of θ, the inclination of the helix relative to the sheet, and Ω, the dihedral angle between the helix axis and the strand axes, are nearly identical. The height of the helix above the sheet, h, is only 1 Å greater in FSD-1 (SEQ ID NO:3). A study of protein core design as a function of helix height for Gb1 variants demonstrated that up to 1.5 Å variation in helix height has little effect on sequence selection (Su & Mayo, supra, 1997). The comparison of secondary structure parameter values and backbone coordinates highlights the excellent agreement between the experimentally determined structure of FSD-1 (SEQ ID NO:3) and the design target, and demonstrates the success of our algorithm at computing a sequence for this ββα motif.

The quality of the match between FSD-1 (SEQ ID NO:3) and the design target demonstrates the ability of our program to design a sequence for a fold that contains the three major secondary structure elements of proteins: sheet, helix, and turn. Since the ββα fold is different from those used to develop the sequence selection methodology, the design of FSD-1 (SEQ ID NO:3) represents a successful transfer of our program to a new motif.

Example 6

Calculation of Solvent Accessible Surface area Scaling Factors

In contrast to the previous work, backbone atoms are included in the calculation of surface areas. Thus, the calculation of the scaling factors proceeds as follows.

The program BIOGRAF (Molecular Simulations Incorporated, San Diego, Calif.) was used to generate explicit hydrogens on the structures which were then conjugate gradient minimized for 50 steps using the DREIDING force field. Surface areas were calculated using the Connolly algorithm with a dot density of 10 Å-2, using a probe radius of zero and an add-on radius of 1.4 Å and atomic radii from the DREIDING force-field. Atoms that contribute to the hydrophobic surface area are carbon, sulfur and hydrogen atoms attached to carbon and sulfur.

For each side-chain rotamer rat residue position i with a local tri-peptide backbone t3, we calculated $A^O_{i,t3}$ the exposed area of the rotamer and its backbone in the presence of the local tri-peptide backbone, and $A_{i,t}$ the exposed area of the rotamer and its backbone in the presence of the entire template t which includes the protein backbone and any side-chains not involved in the calculation (FIG. 13). The difference between $A^O_{i,t3}$ and $A_{i,t}$ is the total area buried by the template for a rotamer r at residue position i. For each pair of residue positions i and j and rotamers r and s on i and j, respectively, $A_{i,j,t}$ the exposed area of the rotamer pair in the presence of the entire template, is calculated. The difference between $A_{i,j,t}$ and the sum of $A_{i,t}$ and $A_{j,t}$ is the area buried between residues i and j, excluding that area by the template.

The pairwise approximation to the total buried surface area is:

$$A^{pairwise}_{buried} = \sum_i (A^0_{i_r t3} - A_{i_r t}) + f \sum_{i<j} (A_{i_r t} + A_{j_s t} - A_{i_r j_s t})$$ Equation 29

As shown in FIG. 13, the second sum in Equation 29 over-counts the buried area. We have therefore multiplied the second sum by a scale factor f whose value is to be determined empirically. Expected values of f are discussed below.

Noting that the buried and exposed areas should add to the total area, $\Sigma_i A^O_{i,t3}$, the solvent-exposed surface area is:

$$A^{pairwise}_{exposed} = \sum_i A_{i_r t} - f \sum_{i<j} (A_{i_r t} + A_{j_s t} - A_{i_r j_s t})$$ Equation 30

The first sum of Equation 30 represents the total exposed area of each rotamer in the context of the protein template ignoring interactions with other rotamers. The second sum of Equation 30 subtracts the buried areas between rotamers and is scaled by the same parameter f as in Equation 29.

Some insight into the expected value of f can be gained from consideration of a close-packed face centered cubic lattice of spheres or radius r. When the radii are increased from r to R, the surface area on one sphere buried by a neighboring sphere is $2\pi R(R-r)$. We take r to be a carbon radius (1.95 Å), and R is 1.4 Å larger. Then, using:

$$f = \frac{\text{true buried area}}{\text{pairwise buried area}}$$

and noting that each sphere has 12 neighbors, results in:

$$f = \frac{4\pi R_2}{12 \times 2\pi R(R-r)}$$

This yields f=0.40. A close-packed face centered cubic lattice has a packing fraction of 74%. Protein interiors have a similar packing fraction, although because many atoms are covalently bonded the close packing is exaggerated. Therefore this value of f should be a lower bound for real protein cores. For non-core residues, where the packing fraction is lower, a somewhat larger value of f is expected.

We classified residues from ten proteins ranging in size from 54 to 289 residues into core or non-core as follows. We classified resides as core or non-core using an algorithm that considered the direction of each side-chain's Cα–Cβ vector relative to the surface computed using only the template Cα atoms with a carbon radius of 1.95 Å, a probe radius of 8 Å and no add-on radius. A residue was classified as a core position if both the distance from its Cα atom (along its Cα–Cβ vector) to the surface was greater than 5.0 Å and the distance from its Cβ atom to the nearest point on the surface was greater than 2.0 Å. The advantage of such an algorithm is that a knowledge of the amino acid type actually present at each residue position is not necessary. The proteins were as shown in Table I, showing selected proteins, total number of residues and the number of residues in the core and non-core of each protein (Gly and pro were not considered).

| Brookhaven Identifier | Total Size | Core Size | Non-Core Size |
|---|---|---|---|
| 1enh | 54 | 10 | 40 |
| 1pga | 56 | 10 | 40 |
| 1ubi | 76 | 16 | 50 |
| 1mol | 94 | 19 | 61 |
| 1kpt | 105 | 27 | 60 |
| 4azu-A | 128 | 39 | 71 |
| 1gpr | 158 | 39 | 89 |
| 1gcs | 174 | 53 | 98 |
| 1edt | 266 | 95 | 133 |
| 1pbn | 289 | 96 | 143 |

The classification into core and non-core was made because core residues interact more strongly with one another than do non-core residues. This leads to greater over-counting of the buried surface area for core residues.

Considering the core and non-core cases separately, the value of f which most closely reproduced the true Lee and Richards surface areas was calculated for the ten proteins. The pairwise approximation very closely matches the true buried surface area (data not shown). It also performs very well for the exposed hydrophobic surface area of non-core residues (data not shown). The calculation of the exposed surface area of the entire core of a protein involves the difference of two large and nearly equal areas and is less accurate; as will be shown, however, when there is a mixture of core and non-core residues, a high accuracy can still be achieved. These calculations indicate that for core residues f is 0.42 and for non-core residues f is 0.79.

To test whether the classification of residues into core and non-core was sufficient, we examined subsets of interacting residues in the core and non-core positions, and compared the true buried area of each subset with that calculated (using the above values of f). For both subsets of the core and the non-core, the correlation remained high ($R^2$=1.00) indicating that no further classification is necessary (data not shown). (Subsets were generated as follows: given a seed residue, a subset of size two was generated by adding the closest residue: the next closest residue was added for a subset of size three, and this was repeated up to the size of the protein. Additional subsets were generated by selecting different seed residues.)

It remains to apply this approach to calculating the buried or exposed surface areas of an arbitrary selection of interacting core and non-core residues in a protein. When a core residue and a non-core residue interact, we replace Equation 29 with:

$$A_{buried}^{pairwise} = \sum_i (A_{i_r t3}^0 - A_{i_r t}) + \sum_{i<j} (f_i A_{i_r t} + f_j A_{j_f t} - f_{ij} A_{i_r j_f t}) \qquad \text{Equation 31}$$

and Equation 30 with Equation 32:

$$A_{exposed}^{pairwise} = \sum_i A_{i_r t} - \sum_{i<j} (f_i A_{i_r t} + f_j A_{j_f t} - f_{ij} A_{i_r j_f t})$$

where $f_i$ and $f_j$ are the values of f appropriate for residues i and j, respectively, and $f_{\{ij\}}$ takes on an intermediate value. Using subsets from the whole of 1 pga, the optimal value of $f_{ij}$ was found to be 0.74. This value was then shown to be appropriate for other test proteins (data not shown).

We claim:

1. A method executed by a computer under the control of a program, said computer including a memory for storing said program, said method comprising the steps of:

(A) receiving a protein backbone structure with variable residue positions;

(B) establishing a group of potential rotamers for each of said variable residue positions, wherein the group of potential rotamers for at least one of said variable residue position has a rotamer selected from each of at least two different amino acid side chains; and (C) analyzing the interaction of each of said rotamers with all or part of the remainder of said protein to generate a set of protein sequences optimized for at least one scoring function, wherein said analyzing step includes a Dead-End Elimination (DEE) computation.

2. A method executed by a computer the control of a program, said computer including a memory for storing said program said method comprising the steps of:

(A) receiving a protein backbone structure with variable residue positions;

(B) classifying each variable residue position as either a core, surface or boundary residue;

(C) establishing a group of potential rotamers for each of said variable residue positions, wherein the group of potential rotamers for at least one of sad variable residue positions has A rotamer selected from each of at least two different amino acid side chains; and (D) analyzing the interaction of each of said rotamers with all or part of the remainder of said protein to generate a set of protein sequences optimized for at least one scoring function.

3. A method according to claim 2 wherein said analyzing step comprises a DEE computation.

4. A method according to claim 1 or 2 wherein said set of protein sequences optimized for at least one scoring function comprises the globally optimal protein sequence.

5. A method according to claim 1 or 3 wherein said DEE computation is selected from the group consisting of original DEE and Goldstein DEE.

6. A method according to claim 1 or 2 wherein said scoring function is selected from the group consisting of a Van der Waals potential scoring function, a hydrogen bond potential scoring function, an atomic salvation scoring function, an electrostatic scoring function and a secondary structure propensity scoring function.

7. A method according to claim 1 or 2 wherein said analyzing step includes the use of at least two scoring functions.

8. A method according to claim 1 or 2 wherein said analyzing step includes the use of at least three scoring functions.

9. A method according to claim 1 or 2 wherein said analyzing step includes the use of at least four scoring functions.

10. A method according to claim 1 or 2 further comprising experimentally testing at least one member of said set.

11. A method according to claim 4 further comprising the step of:
   generating a rank ordered list of additional sequences from said globally optimal protein sequence, wherein said additional sequences are optimized for at least one scoring function.

12. A method according to claim 11 wherein said generating includes the use of a Monte Carlo search.

13. A method according to claim 2 wherein said analyzing step comprises a Monte Carlo computation.

14. A method according to claim 11 further comprising the step of:
   testing some or all of said protein sequences from said ordered list to produce potential energy test results.

15. A method according to claim 14 further comprising the step of:
   analyzing the correspondence between said potential energy test results and theoretical potential energy data.

16. A method according to claim 11, wherein said experimentally testing comprises testing for stability or function of said at least one member of said set.

* * * * *